(12) United States Patent
Barnes et al.

(10) Patent No.: US 12,073,342 B2
(45) Date of Patent: *Aug. 27, 2024

(54) INFORMATICS PLATFORM FOR INTEGRATED CLINICAL CARE

(71) Applicant: Roche Molecular Systems, Inc., Pleasanton, CA (US)

(72) Inventors: Michael Barnes, San Francisco, CA (US); Stephen Burnell, Santa Cruz, CA (US); William Evans, Mountain View, CA (US); Weng Chi Lou, Lisbon (PT); Mark M. Morita, Morgan Hill, CA (US); Oluwatosin Oyeniran, San Jose, CA (US); Joseph Perez-Rogers, Brighton, MA (US); Joachim Schmid, Santa Barbara, CA (US)

(73) Assignee: Roche Molecular Systems, Inc., Pleasanton, CA (US)

( * ) Notice: Subject to any disclaimer, the term of this patent is extended or adjusted under 35 U.S.C. 154(b) by 266 days.

This patent is subject to a terminal disclaimer.

(21) Appl. No.: 17/203,190

(22) Filed: Mar. 16, 2021

(65) Prior Publication Data

US 2021/0343429 A1 Nov. 4, 2021
US 2022/0189644 A9 Jun. 16, 2022

Related U.S. Application Data

(63) Continuation of application No. 15/263,236, filed on Sep. 12, 2016, now Pat. No. 10,963,821.
(Continued)

(51) Int. Cl.
*G16H 80/00* (2018.01)
*G06F 3/04817* (2022.01)
(Continued)

(52) U.S. Cl.
CPC ......... *G06Q 10/06* (2013.01); *G06F 3/04817* (2013.01); *G06F 16/951* (2019.01);
(Continued)

(58) Field of Classification Search
CPC ... G06Q 10/06; G06F 3/04817; G06F 16/951; G06F 40/40; G06F 3/0482; G06T 11/206;
(Continued)

(56) References Cited

U.S. PATENT DOCUMENTS 9,654,739 B1 * 5/2017 Mitchell ............... H04N 5/2228
2006/0236247 A1 10/2006 Morita et al.
(Continued)

FOREIGN PATENT DOCUMENTS

CN 1983258 A 6/2007
CN 101034410 A 9/2007
(Continued)

OTHER PUBLICATIONS

Zhang, A mobile network-based multimedia teleconference system for homecare services, Mar. 2008, Telemedicine and e-Health, vol. 14, Iss. 2, pp. 147-155. (Year: 2008).*
(Continued)

*Primary Examiner* — Christopher L Gilligan
(74) *Attorney, Agent, or Firm* — Kilpatrick Townsend and Stockton LLP

(57) ABSTRACT

An informatics platform provides an architecture to integrate information from relevant patient information systems. The informatics platform may include: a workflow tool that can be used to prepare and review information at multi-disciplinary board meetings; a visual timeline of patient events; a search engine to search for patients with specific attributes; a graphing tool that can display disparate clinical variables in a single chart; a virtual PinBoard for users to identify relevant patient information for board meetings; an image
(Continued)

viewing application that can provide for comparison of images from different information systems; structured reporting functionality that incorporates system aggregated patient information and board recommendations; an application interface that integrates clinically relevant tools to provide patient specific references; a collaboration interface that facilitates communication of patient specific information and documents the discussion threads as independent reference points; and a default display of relevant patient information customized for each clinical specialty.

19 Claims, 64 Drawing Sheets

Related U.S. Application Data

(60) Provisional application No. 62/270,927, filed on Dec. 22, 2015, provisional application No. 62/270,866, filed on Dec. 22, 2015, provisional application No. 62/235,923, filed on Oct. 1, 2015, provisional application No. 62/235,396, filed on Sep. 30, 2015, provisional application No. 62/235,397, filed on Sep. 30, 2015, provisional application No. 62/235,392, filed on Sep. 30, 2015, provisional application No. 62/235,378, filed on Sep. 30, 2015, provisional application No. 62/235,387, filed on Sep. 30, 2015, provisional application No. 62/235,399, filed on Sep. 30, 2015, provisional application No. 62/235,381, filed on Sep. 30, 2015, provisional application No. 62/235,388, filed on Sep. 30, 2015, provisional application No. 62/216,688, filed on Sep. 10, 2015.

(51) Int. Cl.
  *G06F 16/951* (2019.01)
  *G06F 40/40* (2020.01)
  *G06Q 10/06* (2023.01)
  *G06T 11/20* (2006.01)
  *G16H 10/60* (2018.01)
  *G16H 30/20* (2018.01)
  *G16H 40/20* (2018.01)
  *G06F 3/0482* (2013.01)

(52) U.S. Cl.
  CPC ............ *G06F 40/40* (2020.01); *G06T 11/206* (2013.01); *G16H 10/60* (2018.01); *G16H 30/20* (2018.01); *G16H 40/20* (2018.01); *G16H 80/00* (2018.01); *G06F 3/0482* (2013.01)

(58) Field of Classification Search
  CPC ........ G16H 10/60; G16H 30/20; G16H 40/20; G16H 80/00
  See application file for complete search history.

(56) References Cited

U.S. PATENT DOCUMENTS

| | | |
|---|---|---|
| 2007/0106536 A1 | 5/2007 | Moore |
| 2008/0026181 A1 | 10/2008 | Morita et al. |
| 2011/0046983 A1 | 2/2011 | Soble et al. |
| 2012/0010896 A1 | 1/2012 | Yeluri et al. |
| 2012/0060216 A1 | 3/2012 | Chaudhri et al. |
| 2012/0066001 A1 | 3/2012 | Sanborn et al. |
| 2012/0116800 A1 | 5/2012 | McCallie et al. |
| 2013/0191161 A1* | 7/2013 | Churchwell ........... G16H 10/60 705/3 |
| 2014/0046976 A1 | 2/2014 | Zhang et al. |
| 2014/0244296 A1 | 8/2014 | Linn et al. |
| 2014/0257854 A1* | 9/2014 | Becker .................... G06F 16/50 705/3 |
| 2014/0275807 A1 | 9/2014 | Redei |
| 2015/0100787 A1* | 4/2015 | Westin ................ H04L 63/0414 713/168 |
| 2015/0244687 A1 | 8/2015 | Perez et al. |
| 2015/0331995 A1* | 11/2015 | Zhao ...................... G16H 50/20 705/2 |
| 2015/0356250 A1* | 12/2015 | Polimeni ................ G16H 10/60 705/3 |
| 2016/0019352 A1* | 1/2016 | Cohen ................... G06F 3/0482 705/3 |
| 2016/0110523 A1 | 4/2016 | Francois |
| 2016/0147945 A1 | 5/2016 | MacCarthy et al. |
| 2017/0039320 A1* | 2/2017 | Shimomura ........... G16H 50/70 |

FOREIGN PATENT DOCUMENTS

| | | | |
|---|---|---|---|
| CN | 101315652 A | 12/2008 | |
| CN | 103635907 A | 3/2014 | |
| CN | 104899410 A | 9/2015 | |
| JP | 2005-189915 A | 7/2005 | |
| JP | 2009-522663 A | 6/2009 | |
| JP | 2011/209871 A | 10/2011 | |
| JP | 2013/242745 A | 12/2013 | |
| JP | 2015-89364 A | 5/2015 | |
| JP | 2015/522871 A | 8/2015 | |
| JP | 2017-509946 A | 4/2017 | |
| KR | 20150037169 A | 4/2015 | |
| WO | 2007/079384 A2 | 7/2007 | |
| WO | 2011/066222 A1 | 6/2011 | |
| WO | WO-2013173747 A1 * | 11/2013 | ........... A61B 5/0022 |
| WO | 2014/105752 A1 | 7/2014 | |
| WO | 2014/107548 A1 | 7/2014 | |
| WO | 2014/139021 A1 | 9/2014 | |

OTHER PUBLICATIONS

Chinese Notification to Grant in CN Appln. 201680052845.2 mailed Jan. 5, 2023; 9 pages.
International Preliminary Report on Patentability mailed Mar. 22, 2018 in connection with PCT/EP2016/071476 filed Sep. 12, 2016, pp. 1-15.
International Search Report and Written Opinion mailed Feb. 22, 2017 in connection with PCT/EP2016/071476 filed Sep. 12, 2016, pp. 1-22.
Japanese Office Action and English Translation in JP Application 2018-512873 mailed Apr. 1, 2019; 7 pages.
Japanese Office Action and English Translation in JP Application 2021-203014 mailed Feb. 3, 2023; 7 pages.
Mitsui Knowledge Industry; "MKI starts providing 'OncoPrime', which analyzes cancergenes and provides doctors with information on the most appropriate drug candidates for their patients"; Mar. 9, 2015; published online and retrieved on Jan. 31, 2023 at https://www.mikco.jp/news/solutions/20150309_1.html; 1 page.
Summons to Attend Oral Proceedings in EP Application 16763831.1 mailed Mar. 10, 2023; 11 pages.
Anonymous; "Protected health information"; Retrieved from the Internet at http://en.wikipedia.org/wiki/Protected_health_information on Jun. 12, 2014.
Decision to Refuse in EP Application 16763831.1 mailed Nov. 15, 2023; 20 pages.
Notice of Allowance and English translation in JP Application 2020-022979 mailed Nov. 26, 2021; 5 pages.

* cited by examiner

INFORMATICS PLATFORM FOR INTEGRATED CLINICAL CARE

CROSS REFERENCE TO RELATED APPLICATIONS

This patent application is a continuation of U.S. patent application Ser. No. 15/263,326, filed Sep. 12, 2016, which claims priority to and the benefit of U.S. Provisional Patent Application Ser. No. 62/216,688 filed Sep. 10, 2015, U.S. Provisional Patent Application Ser. No. 62/235,378 filed Sep. 30, 2015, U.S. Provisional Patent Application Ser. No. 62/235,381 filed Sep. 30, 2015, U.S. Provisional Patent Application Ser. No. 62/235,387 filed Sep. 30, 2015, U.S. Provisional Patent Application Ser. No. 62/235,388 filed Sep. 30, 2015, U.S. Provisional Patent Application Ser. No. 62/235,392 filed Sep. 30, 2015, U.S. Provisional Patent Application Ser. No. 62/235,396 filed Sep. 30, 2015, U.S. Provisional Patent Application Ser. No. 62/235,397 filed Sep. 30, 2015, U.S. Provisional Patent Application Ser. No. 62/235,399 filed Sep. 30, 2015, U.S. Provisional Patent Application Ser. No. 62/235,923 filed Oct. 1, 2015, U.S. Provisional Patent Application Ser. No. 62/270,866 filed Dec. 22, 2015, and U.S. Provisional Patent Application Ser. No. 62/270,927 filed Dec. 22, 2015, each of which is incorporated herein by reference in its entirety.

FIELD OF THE DISCLOSURE

The present application generally relates to systems and methods that integrate patient information from disparate information systems for use by medical personnel in the treatment of the patient.

BACKGROUND

Patient information can be stored in numerous individual information systems that can perform analyses and reports on that very specific data. Such systems include, for example an EMR (electronic medical record) system, a PACS (picture archiving and communication system), a Digital Pathology (DP) system, an LIS (laboratory information system), RIS (radiology information system), etc. These individual information systems do not have the ability to leverage data across information systems due to a lack of integration, and do not provide intelligent aggregation and display of the information. Instead, medical personnel is forced to hunt for information kernels in disparate information systems, where the desired information may be nestled many levels beneath the primary screen of interaction of an information system.

The storing of patient information in multiple information systems can cause problems for medical personnel, such as doctors, physicians and/or clinicians, who are attempting to view, at a single time, a complete and comprehensive clinical data set for a patient. For example, medical personnel may be unable to view radiology images alongside pathology images with related diagnostics and biomarkers. Medical personnel traditionally enter each corresponding information system to view the specific patient related information independent of other clinical information for the patient. Since medical personnel cannot see all of the relevant information and data for a patient at a single viewing, medical personnel are often forced to rely on their memory or on handwritten notes with regard to some pertinent patient information when attempting to make meaningful correlations and associations of various data points.

As an example, when preparing for tumor board presentations, medical personnel currently have to access individual information systems to obtain the desired patient information. Additionally, medical personnel are forced to print paper based notes, prepare hand written notes and create digital presentations by copying and pasting images and relevant information. Much time and effort is involved in this very tedious, manual process. Furthermore, medical personnel cannot present information from the disparate information systems in real-time during the tumor board meeting. During the tumor board meeting, hand written notes are often taken to capture the information that was shared with the multi-disciplinary team to provide context to the development of the group-defined treatment plan for the patient and to track which medical personnel participated in the group-defined treatment plan.

Presently, healthcare information systems contain department-specific patient information only. The lack of integration of all relevant healthcare information systems (e.g., EMR, RIS, PACS, DP, LIS, and other relevant systems) can prevent medical personnel from being able to search across the systems with respect to a specific patient to better understand the comprehensive, holistic view of the patient's information. Medical personnel often search each individual system on a patient and manually review, compare and correlate and/or aggregate the information to determine correlations or unique patterns that may exist within multiple clinical values.

Medical personnel are also challenged to document the discussions and treatment plans that take place during the multi-disciplinary tumor board meetings. In many cases, the information is documented by doctors, nurses or other administrative personnel who enter free text into the EMR sometimes days or weeks after the meeting has occurred. The administrative team is then challenged to decipher or interpret handwritten notes of others without the immediate benefit of clinical context or the immediacy of the discussion that would allow to accurately document the group consensus for the treatment plan for the patient. Further, free text documentation presents the challenge of easily mining the data for future analysis or undocumented correlation patterns within the tumor board notes and recommendation.

The charting of relevant clinical values of a patient typically involves entering several information systems (since many of the desired clinical values exist in different information systems), aggregating the relevant clinical results over time, inputting the aggregated data into a visualization application and then finally rendering the information in a visual chart. The resulting chart likely would be static and provide little or no connections back to the source systems. A doctor cannot interact with the chart to add additional data points or explore other relevant, potential clinical values from the chart unless the doctor enters the specific information system originating the clinical value of interest. If the doctor wants to document the charting exercise, the doctor has to either add it to the paper based medical record of the patient or decide which specific information system to add a .PDF report.

Referring back to multi-disciplinary tumor board meetings, such meetings currently require medical personnel to rely on outdated technologies, such as printed notes from disparate information systems, hand written notes and PowerPoint presentations with information copied/pasted from disparate information systems. Each doctor participating in the multi-disciplinary tumor board meeting often reviews relevant information from the unique information systems in their clinical domain without the benefit of clinical context from other disciplines. Because the relevant information is "piecemealed" together, it is difficult to review all of the relevant patient information and attributes and document or flag the specific, relevant data points that were presented as context to understand the patient's current clinical state and the final treatment decision.

Current medical information systems can require medical personnel and other clinical care providers and administrators to write free-form text notes or select a value from drop-down menus to describe a patient's medical status. A patient's overall medical status includes many individual elements, such as a patient's history of smoking, allergies, allergies to medications, current medications, and many other medically relevant characteristics or events. When these pieces of information are retrieved from a medical information system and viewed by medical personnel, the information often appears in the same or similar text-based format that was used to originally enter the information. While the raw information itself is available, the format of the information, i.e., raw text or drop-down menu values, often requires that the viewer visually parse and read text in order to understand the patient's medical status. Reading such a list is time consuming, and it typically requires the user to remember a list of items that can be easily forgotten with no ready mnemonic to assist with memorizing the "overall picture" of the patient.

Past solutions have focused on text-based designs that tend to subdivide visual screen space into discrete forms or "areas" dedicated to a different domain of medical information. Each of these areas is individually filled with text, form fields, or both. Pictorial or visual elements are rarely, if ever, used to provide a summary status of key medical events or health status indicators for a patient.

SUMMARY

The present application is directed, among other things, to an informatics platform for integrated clinical care that provides an architecture to integrate information from relevant patient information systems. The informatics platform may include: a visualization and workflow tool that can be used to prepare and review information at multi-disciplinary board meetings; a visual timeline of patient events; a search engine to search for patients with specific attributes; a graphing tool that can display disparate clinical variables in a single chart; a virtual PinBoard for users to identify relevant patient information for board meetings; an image viewing application that can provide for "side by side" comparison of images from different information systems; structured reporting functionality that incorporates system aggregated patient information and board recommendations; an application interface that enables the integration of clinically relevant tools to provide patient specific references; a collaboration interface that facilitates communication of patient specific information and documents the discussion threads as independent reference points; and a default display of relevant patient information customized for each clinical specialty.

BRIEF DESCRIPTION OF THE DRAWINGS

Color drawings have been submitted in this application. The color drawings are necessary in this case because colored drawings represent the only way currently known that can accurately depict the images. Reducing the colored drawings to black and white drawings could not be done in a way that would preserve the features contained therein.

Wherever possible, the same reference numbers are used throughout the drawings to refer to the same or like parts.

DETAILED DESCRIPTION

Figure 1:
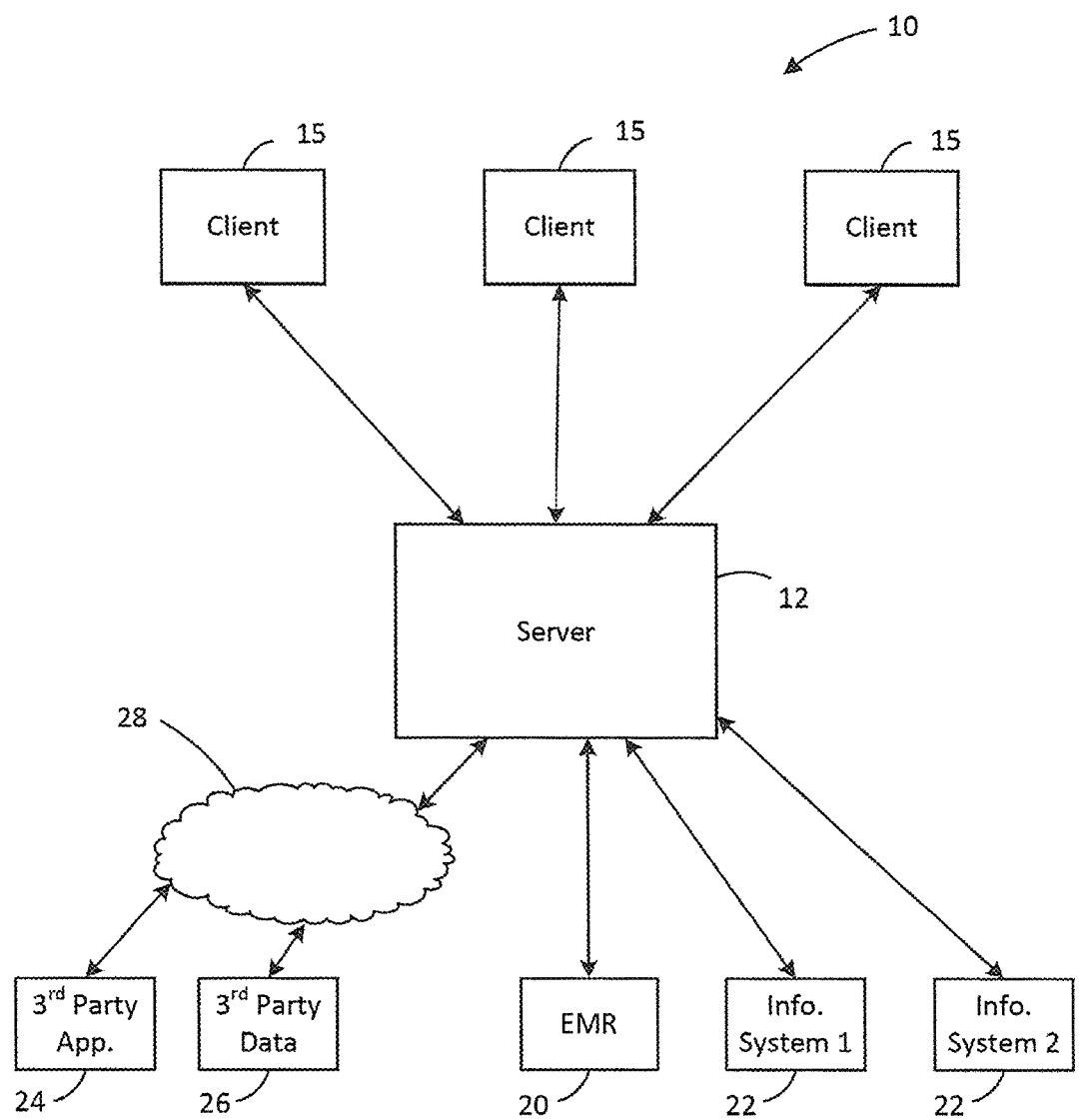
FIG. 1 schematically shows an embodiment of an informatics platform system.

The present application generally pertains to an informatics platform for integrated clinical care that provides an architecture leveraging comprehensive integration of relevant patient information systems. The informatics platform incorporates systems and methods that provide medical personnel with the ability to access features and functions such as: an oncology tumor board visualization and workflow tool that provides medical personnel the ability to prepare for and present at multi-disciplinary tumor board meetings; a visual timeline that allows filtering by department and procedure; automated and manual search queries based on specific, clinical attributes that provide search results of similar populations of patients with matching clinical attributes to easily visualize previous treatments/outcomes for similar patients and the ability to search for "populations" of similar patients that may be eligible for clinical trials or other research purposes; a graphing tool that provides the ability to visualize disparate clinical variables (currently residing in disparate information systems) and provide access to qualitative images and reports that correspond to specific dates and time; tumor board PinBoard and workflow that provides a software toolset to flag relevant, contextual patient information that includes images, reports, lab values, hyperlinks and other accessible information for easy access in preparation, presentation and future reference related to tumor boards; an image viewing application that provides basic image manipulation, direct, SSO (single sign-on) access to source PACS and DP information systems and "side by side" comparison of images; structured reporting functionality that provides system aggregated patient information, clinical trial query results specific to the patient and a mechanism to capture multi-disciplinary tumor board recommendations; an application interface (similar to an "App" store) that enables the integration of clinically relevant tools from third party vendors to provide patient specific references; synchronous and asynchronous collaboration interfaces that facilitate communication of patient specific information, documents the discussion threads as independent reference points, provides an interface for virtual tumor boards and clinical consultations, and documents resolution of discordant clinical information; and a default display of relevant patient information customized for each clinical specialty involved in the treatment of an oncology patient.

The present application also generally pertains to a workflow tool that enables the preparation, presentation and archiving of information associated with cancer patient treatment plans from multi-disciplinary tumor boards. The workflow tool includes systems and methods that permit users to leverage the following features: visualization of contextual patient data chronologically from disparate information systems; a visual timeline that allows filtering by department and procedure; an image viewing application that provides basic image manipulation and direct access to source information systems; a visualization interface that provides relevant clinical information specific to oncology patient attributes enabling doctors to easily visualize current state details with the ability to drill down for full granular details; synchronous and asynchronous collaboration for medical personnel to easily share clinical information and communicate; patient lists that provide graphical indicators to understand current state and readiness for tumor board presentations with an immediate mechanism to understand the point of discussion at the patient's tumor board; and an interface to enable tumor board managers the ability to quickly see patients, understand preparation requirements, participation and allocate meeting rooms and doctor calendars.

The present application further generally pertains to search tools that enable medical personnel to search the database which contains information from information systems such as EMR, radiology RIS (radiology information system)/PACS, digital pathology, and LIS systems. The search tools include the following applications: an automated similar patient search to automate a search query for patients with a specific cancer type based on specific, but editable, clinical characteristics and display patient profiles of patients with similar clinical characteristics, treatments and outcomes; and a manual interactive similar patient search to look for "pools" of similar patients based on very specific clinical attributes to find patients that match the specific characteristics.

The present application additionally pertains to systems and methods to provide a tumor board recommendation form that provides the medical personnel the ability to document patient contextual information, the relevant lab reports and clinical tests results that are presented along with structured tumor board recommendations that can be mined for analyses and future disease patterns. The systems and methods provide users the following features: an interactive ability to include radiology images and reports; an interactive ability to include pathology images and reports; an interactive ability to include genomic sequencing image and reports; an automated ability to include relevant patient information (e.g., age, gender, clinical problems, allergies and current medications), tumor information (e.g., type of cancer, size, location, staging and TNM (T=tumor invasive score, N=nodal involvement score, M=metastasis score)) and other related demographic information with the ability to edit clinical values; an interactive ability to easily select cascading, structured tumor board recommendations; an ability to use relevant patient and clinical attributes as key words to auto-populate clinical trials specific to a patient; an ability to document additional clinical tests that can be performed for the patient; and an ability to capture the medical personnel that attended the tumor board meeting based on their RSVP to participate.

The present application still further generally pertains to systems and methods to enable visualization and manipulation of a variety of clinical variables over time. Such systems and methods permit the graphing of multiple laboratory values over a selected period of time. Additionally, levels of specific patient biomarkers can be graphed. Also, diagnostic images, chemotherapy treatments and other procedures can also be charted in the same context to provide correlation of data points that have not been considered previously.

The present application also generally pertains to a virtual "PinBoard" which enables medical personnel from oncology, radiology, pathology and other contributing departments to designate specific patient data points that includes, for example, radiology images, lab reports, clinical notes and test results. Medical personnel are able to "save to tumor board" information which can be categorized by clinical domain and numbered to provide participants the ability to interactively review the preparation status by clinical specialist. Additionally, the virtual PinBoard is saved and documented as supporting evidence for the treatment decision made by the tumor board. Other users have the ability to reference the detailed clinical information which provided context to a patient's specific tumor board in the future as a reference to that patient and in better understanding how other similar patients may be treated.

The present application also generally pertains to a patient health status tool to manage patient information in two broad domains: (1) General patient health including for example: status of allergies, smoking/non-smoking, current medications, past surgical interventions, and performance status (e.g., Karnofsky, Zubrod, Lansky scoring); and (2) oncology-specific status measures which include "TNM staging" and biomarker status (for hormone, gene and other biological measures such as HER2 status, progesterone receptor (PR) antibody level, estrogen receptor (ER) antibody level, and Ki-67 protein expression level).

One advantage of the present application is to enable visualization, correlation, collaboration and actionable insight on patient information by medical personnel to improve patient care.

Another advantage of the present application is to provide intelligent visualization of relevant patient information in a single, easy-to-use interface.

A further advantage of the present application is the ability to provide workflow and visualization of patient clinical information all originating from disparate information systems.

Still another advantage of the present application is that medical personnel can quickly document the treatment decisions during a tumor board meeting with an interactive recommendation form that can provide the clinical context for the patient and an easy way to document, through structured reporting, the treatment plans for the patient.

Yet another advantage of the present application is the generation of a "hub" of structured, high-resolution, doctor curated, diagnostic and treatment decision data.

An additional advantage of the present application is that it enables multi-disciplinary care teams to integrate clinically relevant patient data with current best evidence to inform clinical decisions and improve the quality of care for patients.

Other features and advantages of the present application will be apparent from the following more detailed description of the identified embodiments, taken in conjunction with the accompanying drawings which show, by way of example, the principles of the application.

Informatics Platform

The present application is generally directed to an informatics platform for integrated clinical care that provides an architecture enabling the integration of relevant information systems storing patent data and information. In one embodiment, the informatics platform can be used to integrate patient data for oncology patients. The informatics platform can enable medical personnel, e.g., doctors, clinicians, administrators, physicians, investigators and specialists, to have more patient information readily available in a single location thereby enabling improved visualization, correlation, collaboration and actionable insight by the medical personnel with regard to the patient information.

The informatics platform can provide medical personnel with a workflow tool for medical board meetings, e.g., an oncology tumor board meeting. The workflow tool provides medical personnel with the ability to prepare for and present information on a patient at a multi-disciplinary board meeting. The workflow tool can chronologically display contextual patient data from disparate information systems for visualization by the medical personnel. In one embodiment, the information systems accessed by the workflow tool can include, but are not limited to, EMR (electronic medical record), PACS (picture archiving and communication system), RIS (radiology information system), Digital Pathology (DP), CL-LIS (clinical laboratory-laboratory information system), AP-LIS (anatomic pathology—laboratory information system), and next generation sequencing (NGS) systems. The workflow tool can be used by medical personnel to summarize relevant information, e.g., tumor information, along with patient demographics from disparate information systems in preparation for a board meeting. The workflow tool can provide an interactive visual timeline of relevant events associated with the patient and permit intelligent filtering of the timeline to obtain only the events of interest to the medical personnel. The workflow tool permits medical personnel to collaborate and exchange ideas and information either in real-time (synchronous) or at different times (asynchronous) either during or before the board meeting. The workflow tool can also incorporate third party online reference tools that can provide automated contextual access via relevant patient clinical values.

The workflow tool permits medical personnel to flag or mark relevant, contextual information, such as images, reports, lab values, hyperlinks and other information accessible through the informatics platform, for easy access in preparation, presentation and future reference related to a board meeting. The workflow tool provides a virtual "Pin-Board" which enables medical personnel from different departments, e.g., oncology, radiology, pathology and other contributing departments, to designate specific patient data points that include, for example, radiology images, lab reports, clinical notes or test results. Medical personnel are able to "save to board meeting" information which the workflow tool can categorize by the clinical domain and number to provide participants of the board meeting the ability to interactively review the preparation status and pertinent information for an individual patient.

The informatics platform can include a visual timeline of patient events that can be filtered by department, procedure or other similar filtering parameter to obtain only the patient events of interest. An image viewing application can be included in the informatics platform to provide basic image manipulation and direct, SSO (single sign-on) access to source PACS and DP information systems. The image viewing application can provide for side by side comparison of images from different specialties and/or information systems. The image viewing application also provides 1 button access to the source information system by passing SSO and context information. The informatics platform can have one or more sets of protocols for the default display of relevant patient information customized for each clinical specialty involved in the treatment of a patient.

The informatics platform can provide a search engine for automated and manual search queries based on specific, clinical attributes that provides search results of similar populations of patients with matching clinical attributes to easily visualize previous treatments/outcomes for similar patients and the ability to search for "populations" of similar patients that may be eligible for clinical trials or other research purposes. The search engine has corresponding searching functionality that enables medical personnel to search the informatics platform database. The informatics platform database can include information from EMR, Radiology RIS/PACS, Digital Pathology, and LIS systems.

The search engine can be used to perform an automated similar patient search. The automated similar patient search is based on search query patterns of medical personnel for a specific diagnosis, e.g., cancer type. The search engine is able to automate a search query for patients with that specific diagnosis (cancer type) based on specific, but editable, clinical characteristics that may include, but are not limited to, age, gender, biomarkers, BIRADS (breast imaging reporting and data system) classification, staging information, previous treatments, outcomes, and family history. From the automated query, the search engine displays patient profiles with similar clinical characteristics, treatments and outcomes. The list of patients with similar clinical characteristics provides a resource for medical personnel to quickly review how other similar patients have responded to prescribed treatments to better understand how a specific patient, with similar clinical attributes, might possibly respond to a particular treatment plan.

The search engine can also be used for an interactive similar patient search. The interactive similar patient search can be used by clinical researchers or clinical trial principal investigators that are looking for "pools" of similar patients based on very specific clinical attributes that reside in the informatics platform database. Medical personnel have the interactive ability to search on very specific clinical attributes for example age, gender, clinical stage, biomarkers, histology, previous treatments, genomic alterations, and outcomes to find patients that match the specified attributes and/or characteristics. Medical personnel would have the ability to interactively modify their search queries to narrow the results by further specifying additional attributes. Additional analysis can be performed on the patients identified in the resulting search queries and the identified patients could potentially be considered or recruited for clinical trials that were not previously available during the patients' initial clinical consultations.

The informatics platform can include a patient data tracker tool that provides the ability to visualize disparate clinical variables from disparate information systems in a graphical form. The graphs not only include the visualization of numerical data, but also provide access to qualitative images and reports that correspond to specific dates and times. The patient data tracker tool can enable the simultaneous visualization and manipulation of a variety of clinical variables over time. The patient data tracker application can permit the graphing of multiple laboratory values over a user-selected period of time. Additionally, levels of specific patient biomarkers can be graphed and diagnostic images, chemotherapy treatments and other procedures can also be charted in the same context to provide for the correlation of data points.

The informatics platform can provide for structured reporting functionality that provides system aggregated patient information, clinical trial query results specific to the patient and the capturing of multi-disciplinary board meeting recommendations. The structured reporting functionality can include a recommendation form that provides medical personnel the ability to document patient contextual information, the relevant lab reports and clinical test results that are presented along with structured board recommendations that can be mined for analysis and future disease patterns. The recommendation form includes the interactive ability to include radiology images and reports, pathology images and reports, genomic sequencing images and reports and the automated ability to include relevant patient information (e.g., age, gender, clinical problems, allergies and current medications), tumor information (e.g., type of cancer, size, location, staging, and TNM), if the patient is an oncology patient, and other related demographic information with the ability to edit clinical values.

The structured reporting functionality provides the interactive ability to easily select cascading, structured board recommendations and the medical personnel that attended the board meeting based on their RSVP to participate. The structured reporting functionality further uses relevant patient and clinical attributes as key words and auto-populates clinical trials specific to a patient, so the medical personnel does not have to exit the current session and provides a structure to document additional clinical tests that can be performed for the patient.

The informatics platform can provide for an application tool that enables the integration of clinically relevant tools and information from third party vendors that can be applied to specific patients. The informatics platform provides an open architecture that enables both internal and external (third party) developers to develop applications that can operate within the informatics platform and that can access the clinical and contextual data in the informatics platform database pertaining to a specific patient such that when utilizing the application, no additional input data has to be provided by the medical personnel.

The applications are able to access specific clinical data points such as gender, age, diagnosis (e.g., type of cancer), staging, and biomarkers. When a user selects an application, the application automatically presents the compiled results that relate to the clinical data for the patient. For example, an application could be developed that would utilize the following data: gender, age, type of cancer, location, biomarker and procedures. From this information, the application could map these variables against NCCN (National Comprehensive Cancer Network) clinical guidelines, display how these variables map out to the most appropriate guideline and also display the next line of recommended treatment for a specific patient. The user would not have to enter any information which would save the user time and provide more time for the user to focus on treating the patient.

Medical personnel have the ability to download the software applications from third party developers thereby enabling the automated passing of relevant clinical information. By selecting one of the software applications, the medical personnel may launch the application, initiate the querying of clinical information from the informatics platform database and execute the application to perform the desired actions with the pre-specified clinical data, so the user would not have to do any additional data entry to obtain the desired output results.

The informatics platform can include a collaboration tool that facilitates synchronous and asynchronous communication of patient specific information and documents the discussion threads as independent reference points. The collaboration tool also provides a platform for virtual board meetings, clinical consultations and documents the resolution of discordant clinical information.

The collaboration tool has a communication interface that enables both synchronous and asynchronous collaboration. The collaboration tool provides for synchronous and asynchronous chat with attached contextual patient attributes and the documentation of the chat is then included in the patient's medical record. The collaboration tool also has the ability to determine the availability of medical personnel and the best method of communication with the medical personnel. The collaboration tool enables asynchronous collaboration streams to document remote board workflow.

FIG. 1 shows an embodiment of a system 10 implementing an informatics platform. The system 10 includes a server 12 with the informatics platform that can be accessed by one or more client devices 15. Each client device 15 is communicatively coupled to the server 12 by a network to exchange, i.e., send and receive, instructions, data and/or information with the server 12. A client device 15 can be a desktop, laptop or tablet computer, a hand-held device, such as a cellular telephone (e.g., smartphone) or portable gaming device, a still and/or video camera or attachable, wearable, implantable or non-invasive computers or devices. The client device 15 can have one or more input devices to permit a user to enter instructions, data and/or information for the server 12 and one or more output devices to permit the user to display instructions, data and/or information received from the server 12. In one embodiment, the network connecting the server 12 and the client devices 15 can be a local area network (LAN) and use an Ethernet protocol to communicate over the network. However, in other embodiments, the network may be the Internet, an Intranet, a wide area network (WAN), or any other type of communication network using one or more communication protocols such as the transmission control protocol/Internet protocol (TCP/IP) when using the Internet.

The server 12 of the system 10 can also access one or more resources to obtain data and information that can be stored in the database of the server 12. The server 12 can be communicatively coupled to an EMR system 20 and one or more information systems 22 (two information systems are shown in FIG. 1) by a network, such as a LAN, to exchange instructions, data and/or information. The server 12 can access the EMR system 20 and the information systems 22 and retrieve information and data from the EMR system 20 and the information systems 22. The server 12 can then index and store the retrieved information from the EMR system 20 and the information systems 22 in a database that can be accessed by the informatics platform. The indexing of the information by the server 12 provides a predetermined structure to the information to enable queries on any single indexed item or multiple items in the database.

In another embodiment, the database and the corresponding data and information can be a "remote" database located on a separate computer from server 12. The remote database can be accessed by the server 12 over a LAN, if the remote database is at the same location as or near the server 12, or the remote database can be accessed by the server 12 over the Internet or other type of WAN, if the remote database is located far from the server 12. If the remote database is at a different location from the server 12, the data and information stored in the remote database may be anonymized to comply with corresponding privacy and security requirements.

The server 12 can also be communicatively coupled to one or more third party applications 24 and one or more third party data sources 26 by a network 28, such as the Internet, to exchange instructions, data and/or information. In one embodiment, the information systems 22 coupled to the server 12 can include, but are not limited to, PACS, RIS, Digital Pathology, CL-LIS, AP-LIS, and NGS systems. In another embodiment, the third party data sources 26 can include PubMed, Up-to-Date and clinicaltrials.gov.

Figure 2:
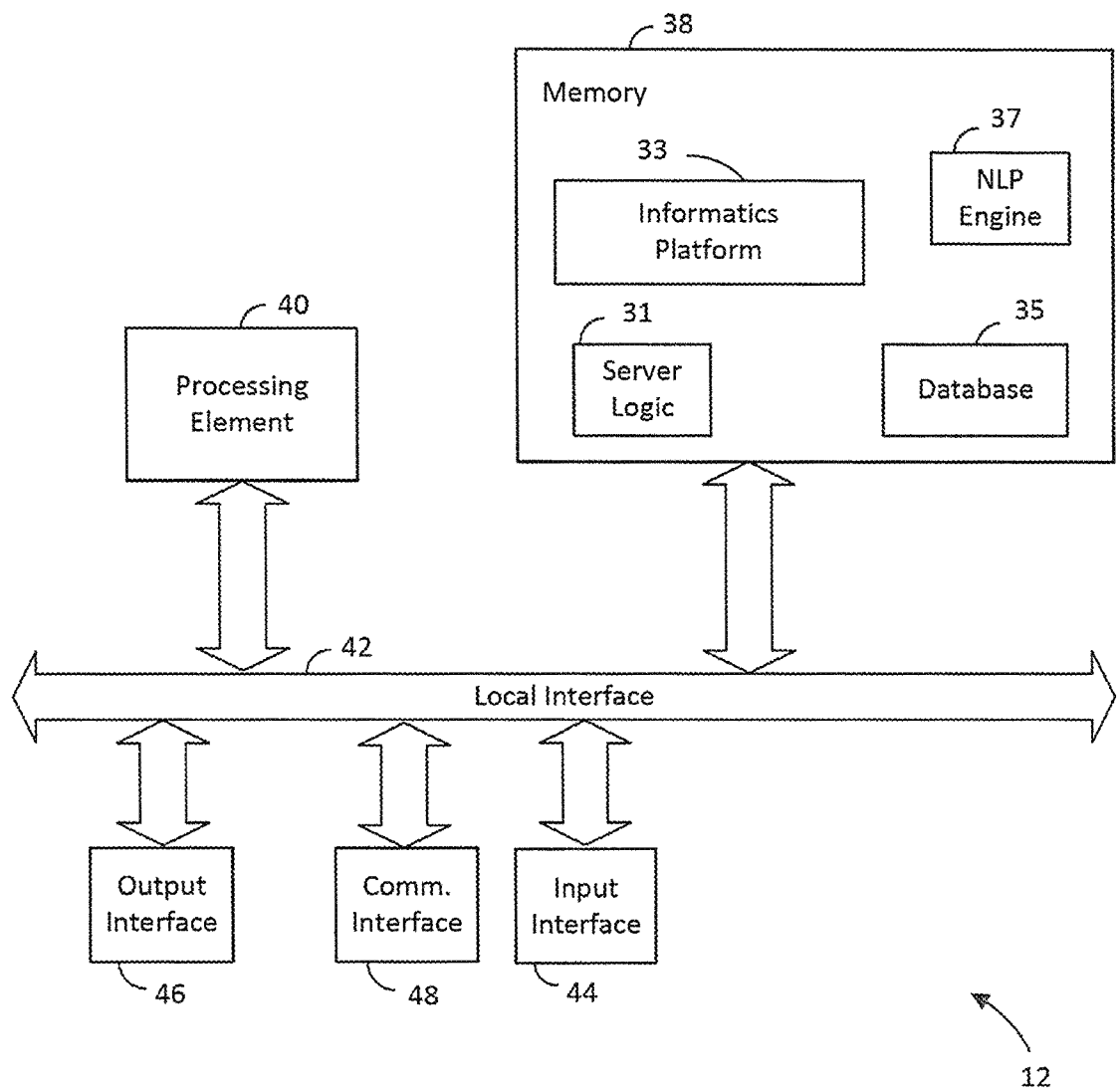
FIG. 2 schematically shows an embodiment of the server of the informatics platform system depicted by FIG. 1.

FIG. 2 shows an embodiment of the server 12. The server 12 can include logic 31, referred to herein as "server logic," for generally controlling the operation of the server 12, including communicating with the client devices 15, the EMR system 20, the information systems 22, the third party applications 24 and the third party data sources 26. The server 12 also includes a natural language processing (NLP) engine 37 to extract data from the EMR 20 and the information systems 22 and provide the data to database 35 and an informatics platform 33 to integrate the extracted data and information from the EMR system 20, the information systems 22, the third party applications 24 and the third party data sources 26 stored in the database 35 and provide the corresponding tools, interfaces and functionality to permit users of the client devices 15 to retrieve and use the information in the database 35. The server logic 31, the informatics platform 33 and the NLP engine 37 can be implemented in software, hardware, firmware or any combination thereof. In the server 12 shown in FIG. 2, the server logic 31, the informatics platform 33 and the NLP engine 37 are implemented in software and stored in memory 38 of the server 12. Note that the server logic 31, the informatics platform 33 and the NLP engine 37, when implemented in software, can be stored and transported on any non-transitory computer-readable medium for use by or in connection with an instruction execution apparatus that can fetch and execute instructions.

The server 12 can include at least one conventional processing element 40, which has processing hardware for executing instructions stored in memory 38. As an example, the processing element 40 may include a central processing unit (CPU) or a digital signal processor (DSP). The processing element 40 communicates to and drives the other elements within the server 12 via a local interface 42, which can include at least one bus. Furthermore, an input interface 44, for example, a keypad, keyboard or a mouse, can be used to input data from a user of the server 12, and an output interface 46, for example, a printer, monitor, liquid crystal display (LCD), or other display apparatus, can be used to output data to the user. Further, a communication interface 48 may be used to exchange data over one or more networks with the client devices 15, the EMR system 20, the information systems 22, the third party applications 24 and the third party data sources 26.

Figure 3:
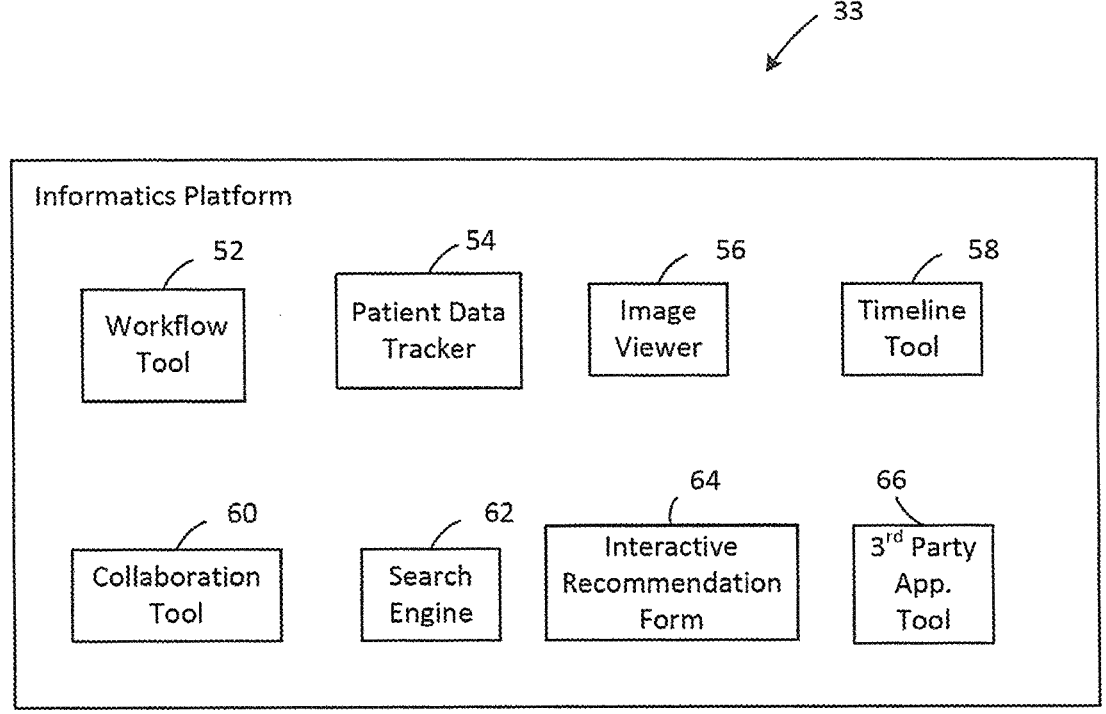
FIG. 3 schematically shows an embodiment of the informatics platform from the server of FIG. 2.

FIG. 3 shows an embodiment of the informatics platform 33. The informatics platform 33 can retrieve data from database 35 and store data in database 35. The informatics platform 33 can provide interfaces, utilities and tools to permit users, e.g., medical personnel, to retrieve and visualize the data and information in the database 35. A workflow tool 52 can enable users to prepare, present and document or archive patient information associated with a multi-disciplinary board meeting. A patient data tracker 54 can provide the ability to visualize disparate clinical variables residing in disparate information systems in a graphical form. An image viewer 56 can provide basic image manipulation and direct, SSO access to source PACS and DP information systems. A timeline tool 58 can generate a visual timeline of patient events that can be filtered by department, procedure or other similar filtering parameter to obtain only the patient events of interest. A collaboration tool 60 can facilitate both synchronous and asynchronous collaborations and communications among medical personnel with patient specific information and archives the discussion threads as independent reference points. A search engine 62 can provide for automated and manual search queries based on specific, clinical attributes that provides search results of similar populations of patients with matching clinical attributes to easily visualize previous treatments/outcomes for similar patients and the ability to search for "populations" of similar patients that may be eligible for clinical trials or other research purposes. An interactive recommendation form 64 can provide system aggregated patient information, clinical trial query results specific to the patient and the capturing of multi-disciplinary board meeting recommendations. A third party application tool 66 can enable medical personnel access to numerous third party applications or data sources and enable the integration of clinically relevant tools and information from third party vendors that can be applied to specific patients.

FIGS. 4-12 show different embodiments of the tools of the informatics platform 33 as implemented for oncology patients. It is to be understood that the informatics platform 33 and the corresponding tools and functionality of the informatics platform can be used for different medical branches or specialties besides oncology.

Figure 4:
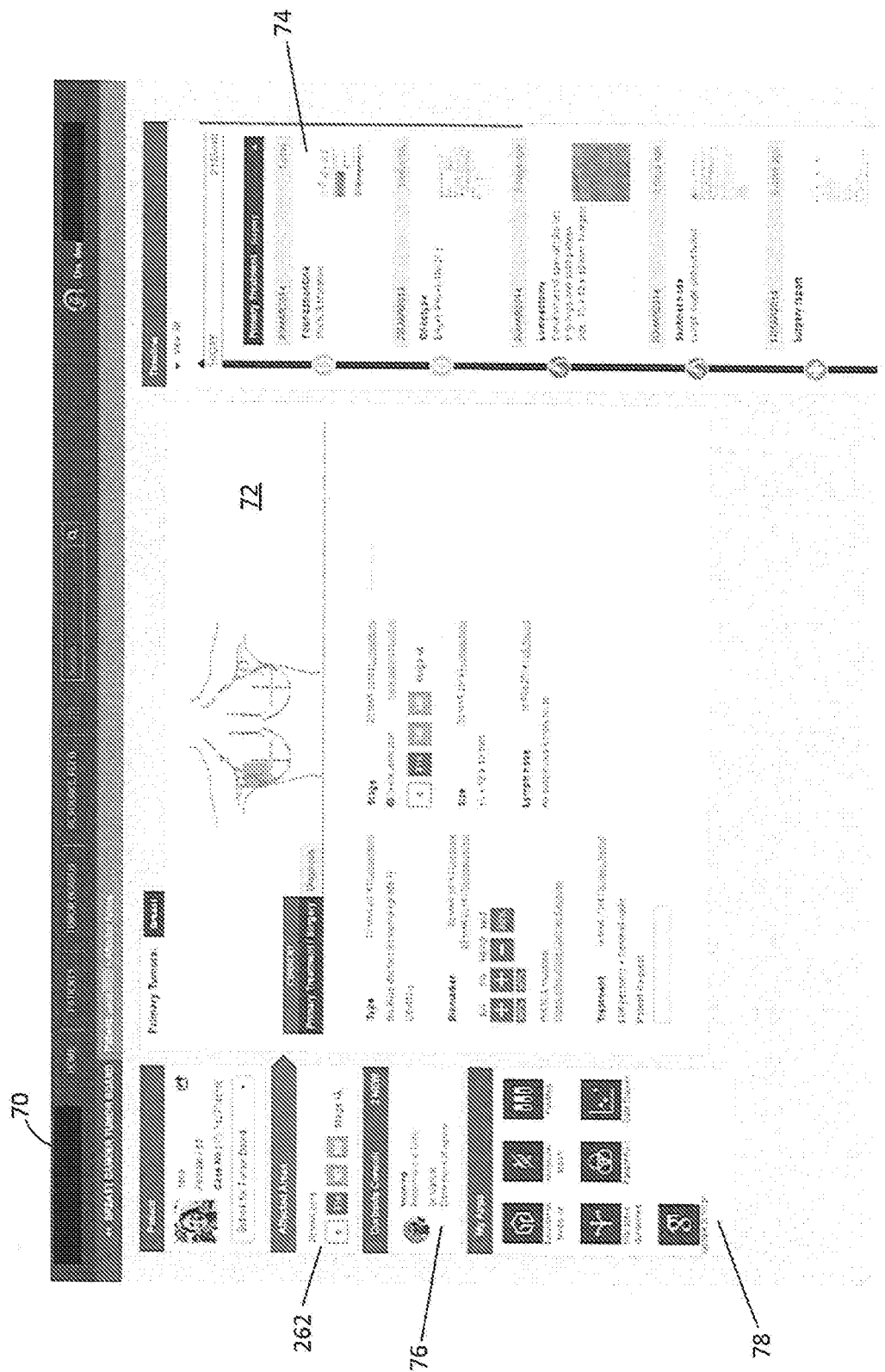
FIG. 4 shows an exemplary screenshot of a graphical user interface (GUI) displayed by a workflow tool from the informatics platform of FIG. 3.

FIG. 4 shows an exemplary screenshot of graphical user interface (GUI) that is displayed by the workflow tool 52 and can be used for tumor board meetings. The workflow tool 52 enables medical personnel to prepare and present patient information and archive the discussion for multi-disciplinary tumor boards relating to cancer patient treatment plans. The workflow tool 52 includes a patient information page 70 having one or more sections providing different information and functionality to the user. The patient information page 70 includes a summary section 72, a timeline section 74, a collaboration section 76 and a reference tool section 78.

The summary section 72 summarizes relevant tumor information along with patient demographics associated with a patient. The summary section 72 can include information on the type, stage and size of the tumor(s) of the patient. The summary section 72 can also include a diagram showing the location of the tumor and information on biomarkers and treatment plans. The tumor information provided by the summary section 72 can be aggregated in the database 35 after being obtained from the EMR system 20 and/or the information systems 22.

The timeline section 74 can provide an interactive visual timeline that provides intelligent filtering capabilities. The timeline section 74 can include events or occurrences associated with surgeries, treatments, laboratory evaluations and genetic evaluations. Each specific event can have a corresponding symbol identifying the type of event being listed. The user is able to filter the timeline to be presented to include only events of a particular type or occurring in a particular timeframe.

The collaboration section 76 enables both synchronous and asynchronous collaborations and communications among medical personnel. The reference tool section 78 displays icons that can link the user to a corresponding application or reference source. When linking to the application or reference source, the workflow tool 52 can provide automated contextual access to the selected application or reference source by providing relevant patient clinical values. In one embodiment, one or more of the applications and references sources can be included in the informatics platform 33 and the database 35. Additional applications and reference sources included in the reference tool section 78 can be provided by third party entities. The third party applications can either be downloaded and stored in database 35 or accessed over network 28 after anonymizing the patient clinical values. Some examples of applications that can be included in and accessed from the reference tool section 78 include visualizing applications (e.g., Data Tracker) and searching applications (e.g., Patient Pool). Some examples of reference sources that can be included in and accessed from the reference tool section 78 include PubMed and Google Scholar.

The reference tool section 78 can also include a Foundation Medicine icon/application that provides a hyperlink to an order form for full genome testing provided by Foundation Medicine, Inc., a Molecular Match icon/application that provides access to an API (application programming interface) to the Molecularmatch.com interface to initiate a clinical trials search query, and an Interactive Guidelines icon/application that provides access to an interactive clinical guidelines application, for example NCCN. The Molecular Match application can take extracted relevant key words from a patient's clinical attributes to formulate the search query. The Interactive Guidelines application can take relevant clinical information from a specific patient and map it to a clinical guideline to provide medical personnel with information on where in the clinical guideline a patient would be from a treatment perspective.

Figure 5:
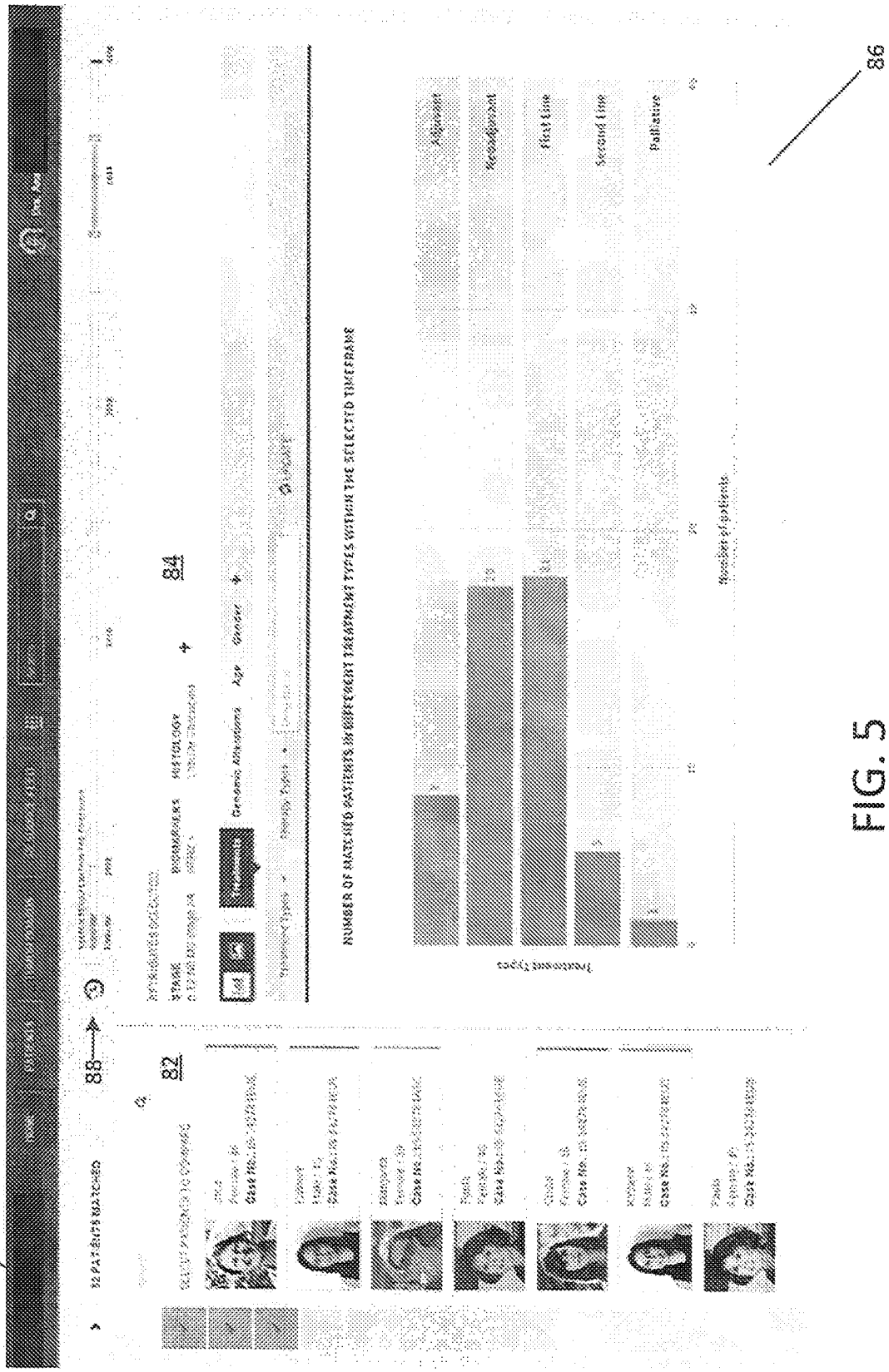
FIG. 5 shows an exemplary screenshot of a GUI displayed by a search engine from the informatics platform of FIG. 3.

FIG. 5 shows an exemplary screenshot of a GUI displayed by the search engine 62. The search engine 62 enables medical personnel to search the database 35, which includes information from EMR system 20 and information systems 22, such as radiology RIS/PACS, digital pathology and LIS, using both automated and manual queries. The search engine 62 includes a search results page 80 having one or more sections providing different information and functionality to the user. The search results page 80 includes a results section 82, an attribute selection section 84, a display section 86 and a date range selection section 88.

The results section 82 provides a listing of the patients in the database 35 that match the selected attributes from the search query. In one embodiment, the user may select one of the patients in the results section 82 and be provided with the medical file of the selected patient. In another embodiment, the user may select several patients in the results section 82 and be provided with a comparison of the attributes of the selected patients. The attribute selection section 84 can provide an interface to select clinical attributes to be used to initiate an updated search for similar patients. In one embodiment, the clinical attributes that can be used for a search for similar patients can include tumor stage, biomarkers and histology. Other attributes that may be searched can include type of cancer, history of smoking, gender, age and physical location.

The display section 86 enables the visual or graphical display of matching attributes. The display section 86 can use different categories to organize the information and attributes for display. Some examples of categories can include age, gender, treatment, and genomic alterations. The categories can then be further organized into sub-categories to provide more refinement to the displayed results. For example, the treatment category may include categories for treatment types and therapy types. The display section 86 can then display information on the number of patients for each treatment type who matched the selected attributes. The date range selection section 88 provides an interactive interface to select the range of years/months/days to update the query for similar patients. The user can select both the starting point of the date range and the duration or length of the date range with the range selection section 88. The search engine 62 then uses the selected date range to limit the scope of the search to only those patients having the selected attributes within the selected date range.

Figure 6:
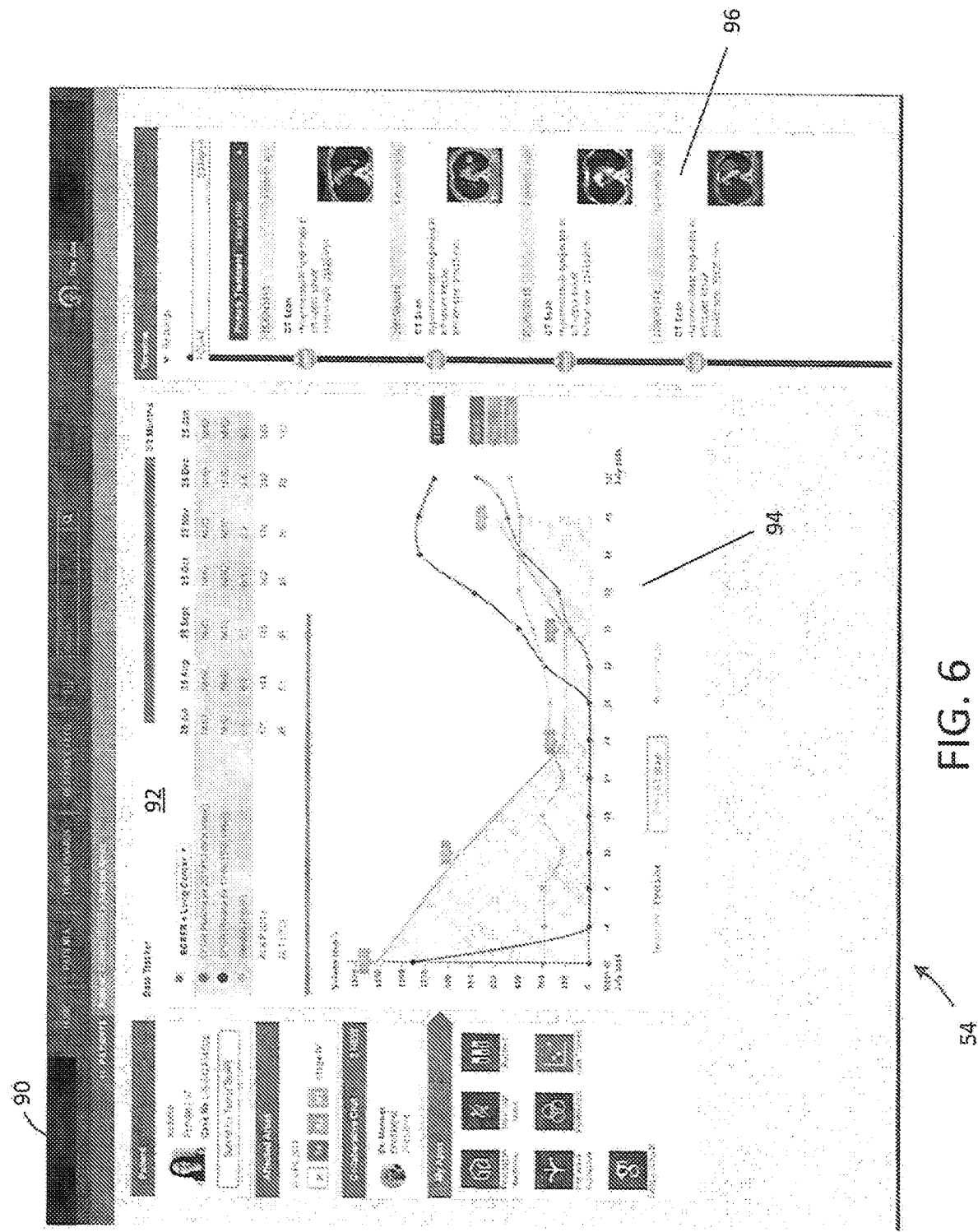
FIG. 6 shows an exemplary screenshot of a GUI displayed by a patient data tracker from the informatics platform of FIG. 3.

FIG. 6 shows an exemplary screenshot of a GUI displayed by the patient data tracker 54. The patient data tracker 54 provides for the visualization of multiple patient attributes such as laboratory results and images and treatments, in a quantitative display (chart) that includes access to qualitative studies. The patient data tracker 54 includes a user interface 90 having one or more sections providing different information and functionality to the user. The user interface 90 includes a table section 92, a charting section 94 and a timeline section 96.

The table section 92 can display numeric results for multiple clinical laboratory procedures and related attributes for a predetermined time period selected by the user. The charting section 94 can provide automatic charting of one or more results from the table section 92. The automatic charting can be for the same time period as in the table section 92 or for a different predetermined time period selected by the user. The charting section 94 can also include plots for treatment and imaging procedures that provide numeric results, e.g., tumor sizes determined from imaging procedures. In one embodiment, the charting section 94 can plot numeric values with different scales on independent X/Y axes. Further, in the cases of images or non-numeric data, thumbnails or other corresponding icons for the images or non-numeric data can be plotted chronologically along a time axis that corresponds with the plotted time axes. The charting section 94 can display all the results included in the table section 92 or can display specific results selected by the user. The timeline section 96 can provide a patient timeline that automatically filters for related imaging procedures when images or non-numeric data is displayed in charting section 94 to permit users to easily hyperlink from chart view in the charting section 94 direct to the imaging study.

Figure 7:
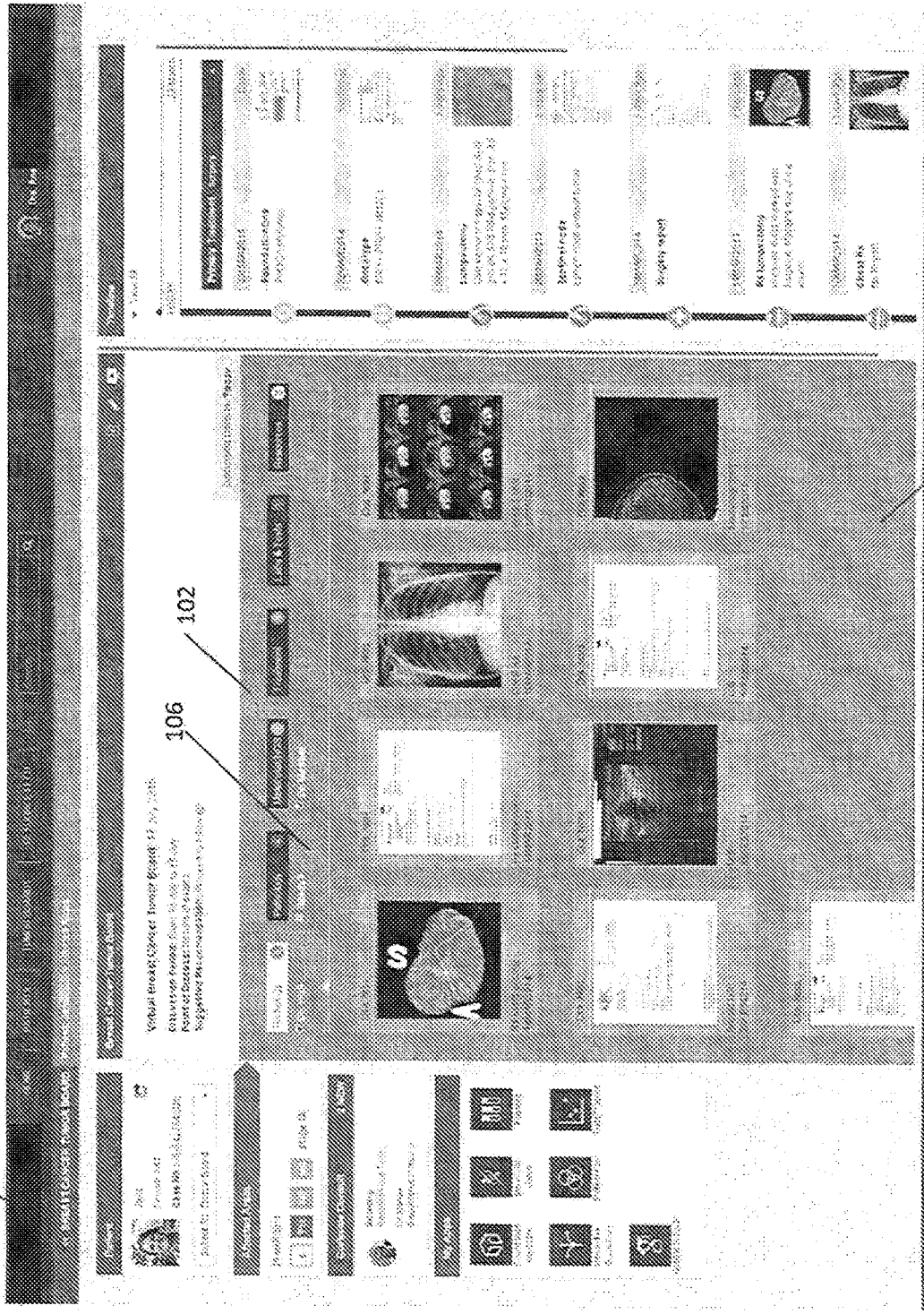
FIG. 7 shows an exemplary screenshot of a GUI displayed by the workflow tool from the informatics platform of FIG. 3.

FIG. 7 shows an exemplary screenshot of a GUI displayed by the workflow tool 52 that can be used for tumor board meetings. The workflow tool 52 provides a virtual "PinBoard" for medical personnel to document and store relevant clinical information, by category, for a patient's multidisciplinary tumor board meeting. The workflow tool 52 includes a virtual PinBoard user interface 100 having one or more sections providing different information and functionality to the user. In one embodiment, the virtual PinBoard user interface 100 can be accessed from either the tumor board timeline element or the tumor board main menu. The virtual PinBoard user interface 100 includes a counter section 102, a display section 104, and a readiness indicator 106.

The counter section 102 includes a counter for each category of clinical information that tracks the number of clinical items selected or "pinned" in a category by specific medical personnel for use in a tumor board meeting. In one embodiment, medical personnel can manually pin or select items by choosing the "save for tumor board" option as they are reviewing timeline elements. Further, medical personnel are also able to "flag" or select images or reports related to a patient from the source systems by saving as "key images" and adding "TB" or "CT" in the associated comment field. The use of the "key images" identification and preselected key words enables the informatics platform 33 to associate the flagged information from the source system with the virtual PinBoard for the patient.

In addition to counting the number of clinical items selected by category, the counter section 102 can also track the number of clinical items selected by a particular doctor or specialist. In one embodiment, each timeline element has an associated category based on the source system supplying the element. Using the associated category for the timeline element, the information, when pinned, is saved into the corresponding category of the virtual PinBoard. In one embodiment, the "pinning" of information for the virtual PinBoard can often be performed by medical personnel from the department corresponding to the information's category. For example, a radiology image in the timeline can be reviewed by a radiologist who can decide to "pin" the image to the virtual PinBoard in the radiology category. Some examples of medical categories can include radiology, pathology, molecular/NGS, treatments, laboratory and test results and resources. In addition, the person who selected the item is stored and associated with the selected item. In one embodiment, a doctor can select clinical items for multiple categories and each category can include clinical items selected by more than one doctor. Medical personnel, such as oncologists, can gauge the preparation for the tumor board meeting by the activity in each category or specialty indicated by the number of selected clinical items.

The display section 104 can provide the user with a display of representative thumbnail images and .pdfs of the clinical items selected for a category. The user can select the category of interest from counter section 102, and the display section can provide thumbnails of the items included in that category. The thumbnails can include the doctor that selected the item and a brief description of the item and the date the item was generated. The thumbnails in the display section 104 can be selectable by a user and can provide the user with access to clinical items. For example, an x-ray thumbnail, if selected, would display the corresponding x-ray for the user and permit the user to interact with the x-ray information. The readiness indicator 106 can be a check box or other similar indicator selected by a doctor under each of the participating clinical specialties to indicate a doctor's readiness in his/her preparation for the associated patient's tumor board discussion. In one embodiment, the workflow tool 52 is aware of the user based on the user's login to the informatics platform 33. When the user manually clicks or selects the "Ready" check box, button or other corresponding displayed option for a category, the workflow tool 52 indicates under that category the name of the person that has selected the Ready check box using the user's login to identify the person. In one embodiment, one or more doctors or specialists can be indicated as ready for a particular category.

Figure 8:
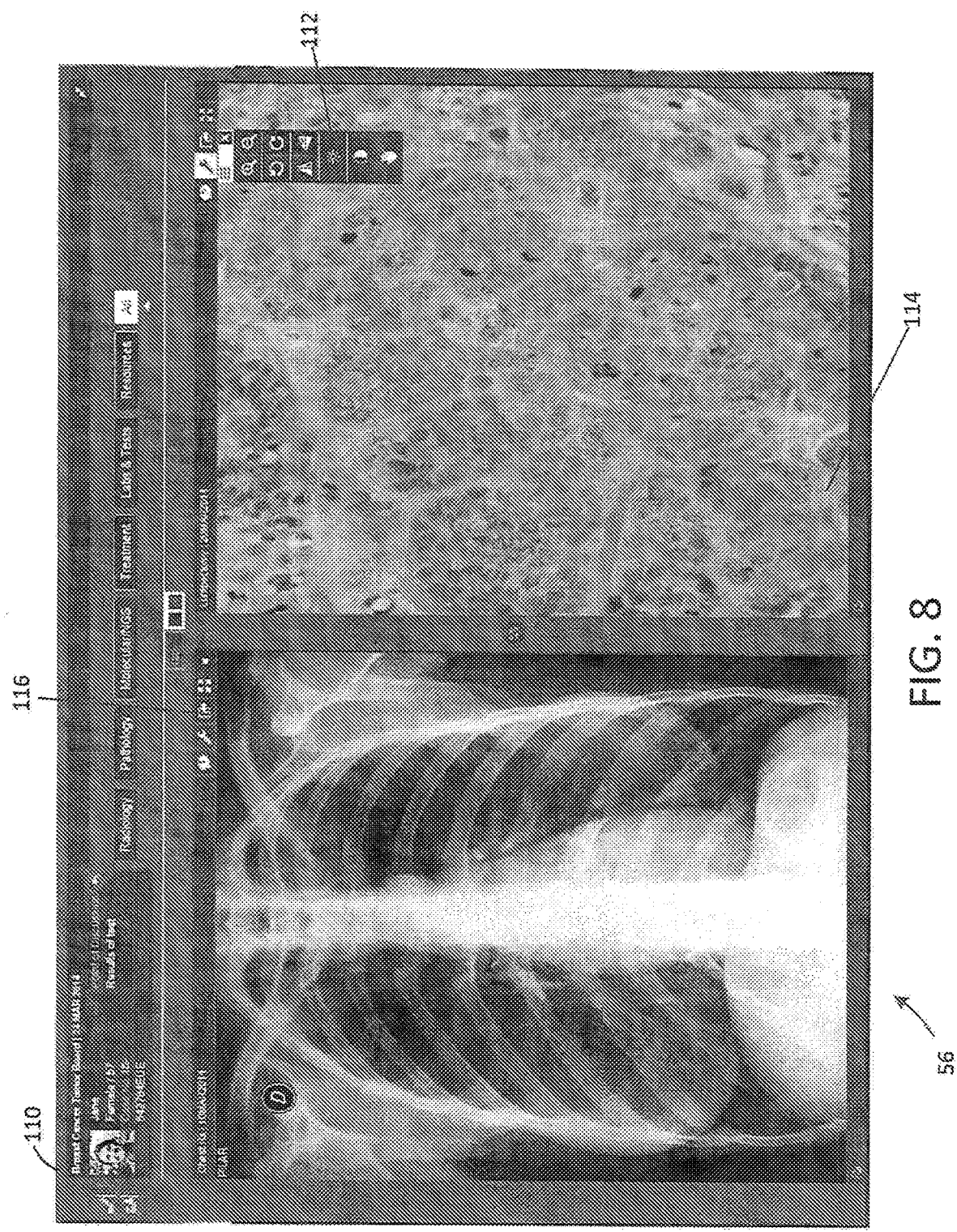
FIG. 8 shows an exemplary screenshot of a GUI displayed by an image viewer from the informatics platform of FIG. 3.

FIG. 8 shows an exemplary screenshot of a GUI displayed by the image viewer 56. The image viewer 56 provides an imaging viewing application to enable medical personnel to view medical images associated with a patient. The viewer 56 includes a user interface 110 having one or more sections providing different information and functionality to the user. The user interface 110 includes manipulation tools 112, image comparison section 114 and a "go to" button 116.

The manipulation tools 112 provide the user with the ability to perform different functions on a displayed image to better enhance the user's viewing of the displayed image. Some of the functions that can be performed on the image include pan, zoom, flip, rotate, brightness/contrast and move.

The image comparison section 114 enables multi-modality image comparison of images of different types and from different information systems. For example, the image comparison section 114 can display a radiology image of the patient next to a pathology image of the patient. In one embodiment, the image comparison section 114 can enable medical personnel to view the same area of the patient with images from different information systems. To access multiple images in the image comparison section 114, the doctor has to manually select the first image by displaying the image in the image comparison section 114. When the doctor would like to compare the currently displayed image to another image, the doctor would click or select the "Compare" button, which can be located adjacent the image comparison section 114, to initiate the comparison mode. The doctor can then select another image for the comparison by clicking or selecting the desired image and the selected image can then be displayed next to or side-by-side to the original image. The go to button 116 provides for SSO access, with patient context, to open up the full fidelity imaging study for the patient within the source system for the image (e.g., PACS/radiology, DP/pathology or NGS/genomics).

Figure 9:
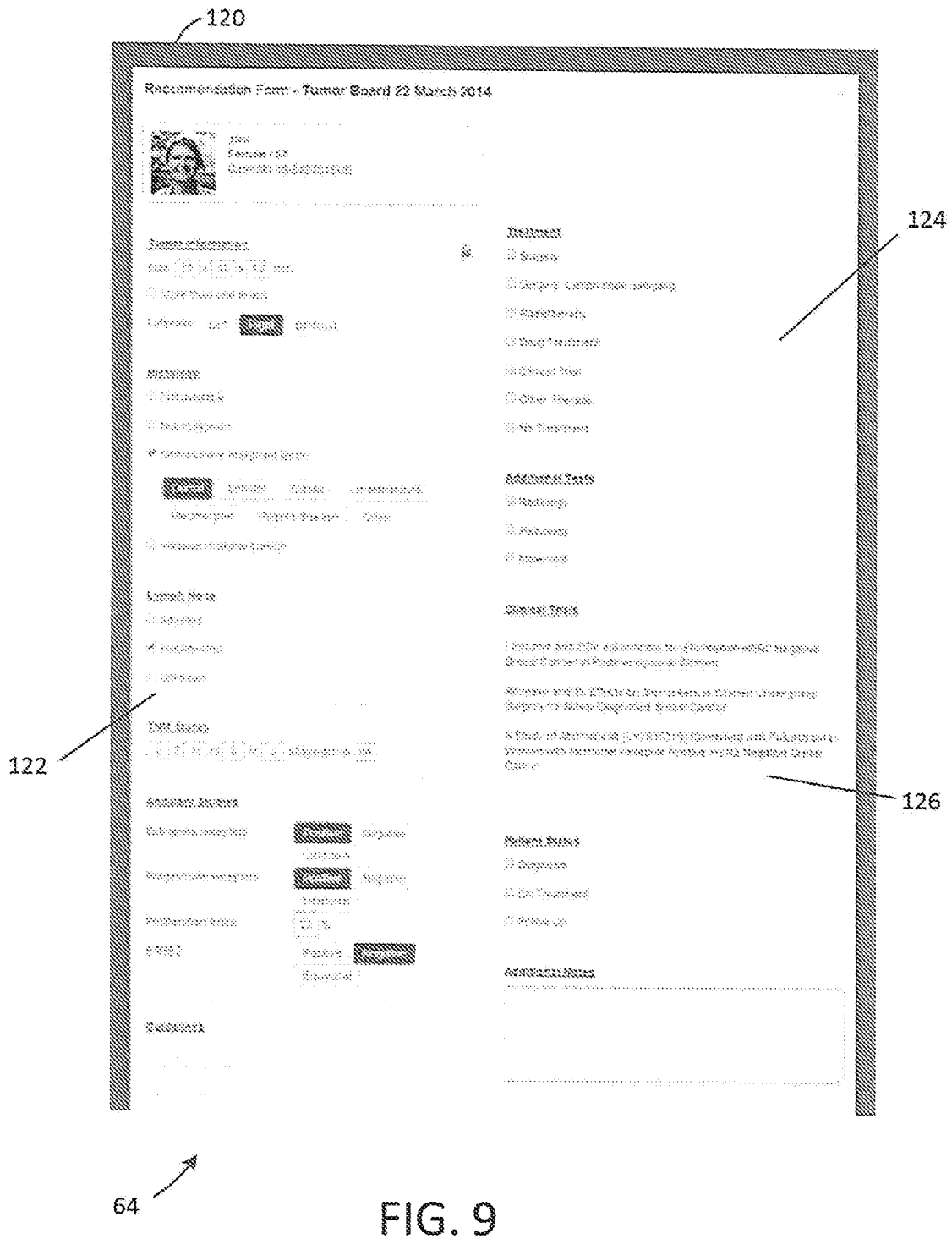
FIG. 9 shows an exemplary screenshot of a GUI displayed by the workflow tool from the informatics platform of FIG. 3.

FIG. 9 shows an exemplary screenshot of a GUI displayed by the workflow tool 52 that can be used for tumor board meetings. The workflow tool 52 includes the interactive recommendation form 64. In one embodiment, the interactive recommendation form 64 can be accessed by clicking or selecting the "Recommendation Form" button in the upper left hand corner of the tumor board presentation mode window. The interactive recommendation form 64 can provide medical personnel with the ability to document patient contextual information, the relevant lab reports and clinical tests results that are presented at the tumor board meeting and to prepare structured tumor board recommendations that can be mined for analysis and future disease patterns.

The interactive recommendation form 64 provides medical personnel the ability to select cascading, structured tumor board recommendations in preparing the specific recommendation or treatment plan for the patient. In one embodiment, the medical personnel can complete the recommendation form in real-time based on the conversations of the multi-disciplinary doctors present during the tumor board meeting. The workflow tool 52 can capture the participating doctors for inclusion in the recommendation form to further document the specific group members that contributed to the treatment plan in the recommendation form. In another embodiment, the completed recommendation form can be provided to each of the participating doctors to obtain their approval of the treatment plan in the recommendation form. The interactive recommendation form 64 includes a recommendation form interface 120 having one or more sections providing different information and functionality to the user. The recommendation form interface 120 includes a patient information section 122, a treatment section 124 and a clinical trials section 126.

The patient information section 122 provides medical personnel with the automated ability to include relevant patient information (e.g., age, gender, clinical problems, allergies and current medications), tumor information (e.g., type of cancer, size, location, staging and TNM staging) and other related demographic information with the ability to edit clinical values. In one embodiment, the workflow tool 52 can auto-populate some or all of the patient information, tumor information and demographic information based on the stored information for the patient in the database 35. The information not completed or entered by the workflow tool 52 can be manually entered by the medical personnel. In addition, when entering some of the information into the patient information section 122, the user may be prompted to enter further information to clarify the user's previous entry. For example, if the user selects a "Non invasive malignant lesion" under a "Histology" tab of patient information section 122, the user may then be prompted to enter or select the type of lesion (e.g., ductal, lobular, undetermined, pleomorphic, Paget's disease or other).

The treatment section 124 provides a structured interface to document recommended treatments (e.g., surgery, radiotherapy, chemotherapy, clinical trial and other therapy) and additional clinical tests (e.g., radiology, pathology and molecular) that can be performed for the patient. Similar to the patient information section 122, when entering information into the treatment section 124, the user may be prompted to enter further information to clarify the user's previous entry.

The workflow tool 52 uses relevant patient and clinical attributes, e.g., gender, age, type of cancer, biomarkers, and/or TNM value, as key words or parameters in formulating a search query to perform a search in one or more databases such as clinicaltrials.gov for potential clinical trials for participation by the patient. Once the potential clinical trials for the patient are identified based on the results of the search, the workflow tool 52 auto-populates the identified clinical trials in clinical trials section 126, so the doctor does not have to exit the workflow tool 52 in order to identify possible clinical trials for the patient.

The recommendation form interface 120 also provides the user with access to interactive NCCN Guidelines to provide the medical personnel with a visualization of how the patient's current attributes, staging and treatments align with appropriate guidelines. In one embodiment, the recommendation form interface 120 can include interactive ability to include radiology images and reports, pathology images and reports, and genomic sequencing images and reports as part of the tumor board recommendation. In another embodiment, the recommendation form interface 120 can include the medical personnel that attended the tumor board meeting, based on their RSVP to participate, as part of the tumor board recommendation. The information entered into the recommendation form interface 120 can be saved in the database 35 and form part of the patient's medical history and/or record.

Figure 10:
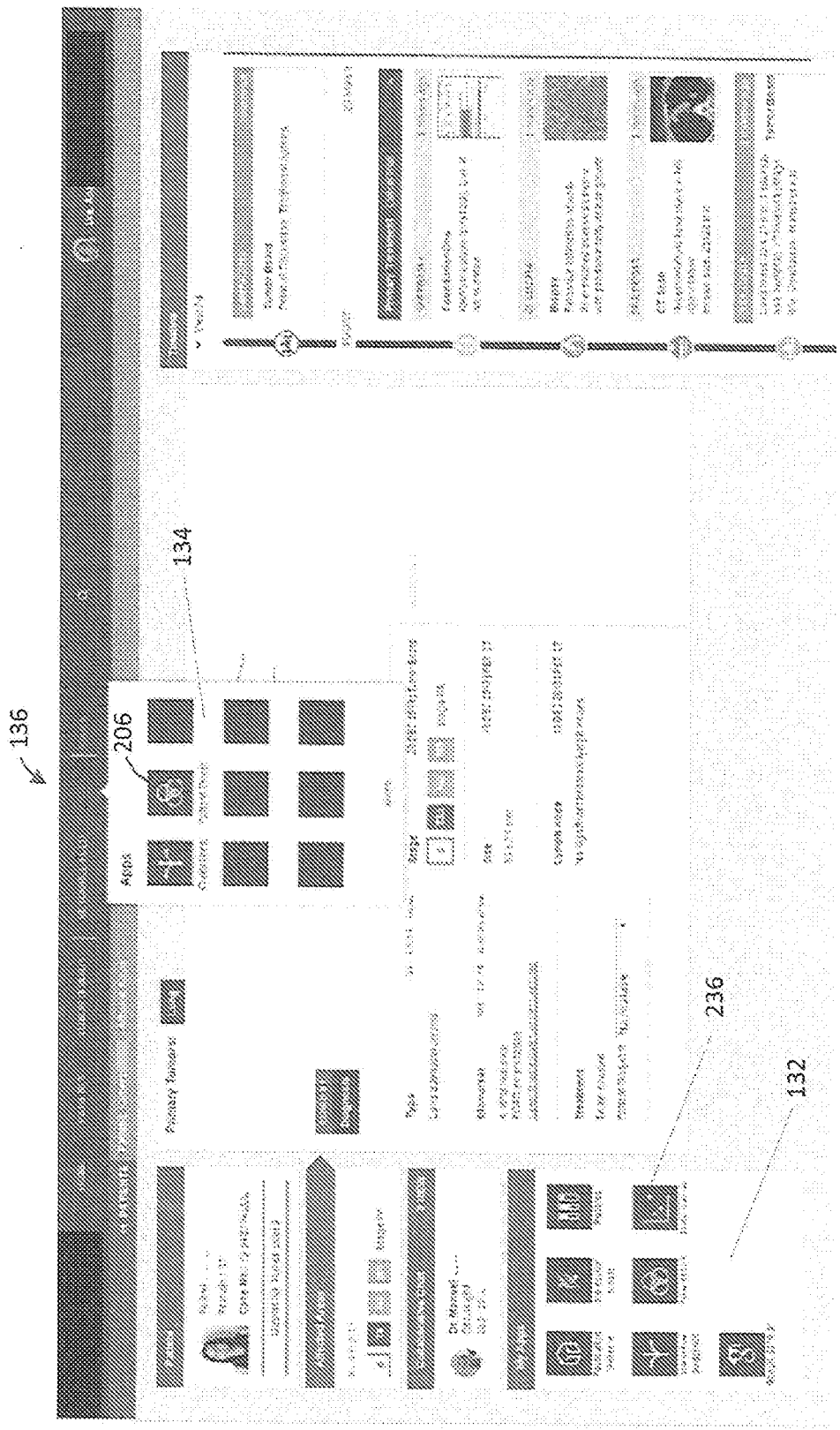
FIG. 10 shows an exemplary screenshot of a GUI displayed by a third party application tool from the informatics platform of FIG. 3.

FIG. 10 shows an exemplary screenshot of a GUI displayed by the third party application tool 66. The informatics platform 33 can provides an open architecture that enables both internal and external (third party) developers to develop applications that work with the informatics platform 33. In addition, the open architecture of the informatics platform 33 enables the developed applications to access and use clinical and contextual data pertaining to a specific patient. When a user accesses or launches an application, the application can automatically access the patient's clinical and contextual data and provide patient-specific results to the user without the user having to perform any additional data entry into the application. For example, for a patient with breast cancer, the third party application tool 66 can assemble the key words originating from various fields in the workflow tool 52 that can include age, gender, type of cancer, biomarkers and family history. After assembling the keywords, the third party application tool 66 passes the assembled keywords into the "APP" API that initiates a search query or other function that relates specifically to the provided keyword values.

The third party application tool 66 can provide a user with a "My Apps" interface or widget 132 and an "Apps" interface or widget 134 in order to access the applications. The My Apps interface 132 can be included with one or more of the tools of the informatics platform 33 (e.g., the workflow tool 52, patient data tracker 54 and the collaboration tool 60) and is the area from which third party applications can be launched. The applications included in the My Apps interface 132 can be "patient-aware" and receive specific clinical and contextual attributes associated with the patient directly from the informatics platform 33, so that when a user selects one of the applications, the screen immediately populates with the resulting analysis and visualization provided by the selected application specifically directed to the patient.

Patient-aware applications can retrieve specific clinical data points of the patient such as gender, age, type of cancer, staging and biomarkers from the database 35. When a user selects a patient-aware application, the patient-aware application can automatically present the compiled results that relate to the retrieved clinical data of the patient. For example, an application could be developed that would retrieve the following patient data: gender, age, type of cancer, location, biomarker and procedures. From the retrieved information, the application could map the data points against NCCN clinical guidelines, display how the data points map out or correspond to the most appropriate guideline and display the next line of recommended treatment for a specific patient. The user would not have to enter any information into the patient-aware application which would save time and provide more time to focus on treating the patient.

In one embodiment, users would have the ability to download paid or free software applications from third party developers that are stored in database 35 and would be able to facilitate the automated passing of relevant clinical information from the database 35 to the application. In another embodiment, a user can select one of the applications from the My Apps interface 132 and launch or access the application over network 28. The application would query for the clinical information from the database 35 and would execute the application with the queried information to perform the desired actions, so the end user would have to do no work, except launch the application, to perform the action and obtain the desired results.

The Apps interface 134 can be accessed from an "Apps" icon 136 in a menu bar of the informatics platform 33. The Apps interface 134 is an area that generic applications can be accessed. Generic applications are not "patient-aware" and require the user to input additional information to initiate the interaction with the application. In one embodiment, generic applications do not use patient-specific information and can be directed to providing access to patient independent information, e.g., treatment guidelines, or can be directed to providing access to one of the tools of the informatics platform 33, e.g., search engine 62.

Figure 11:
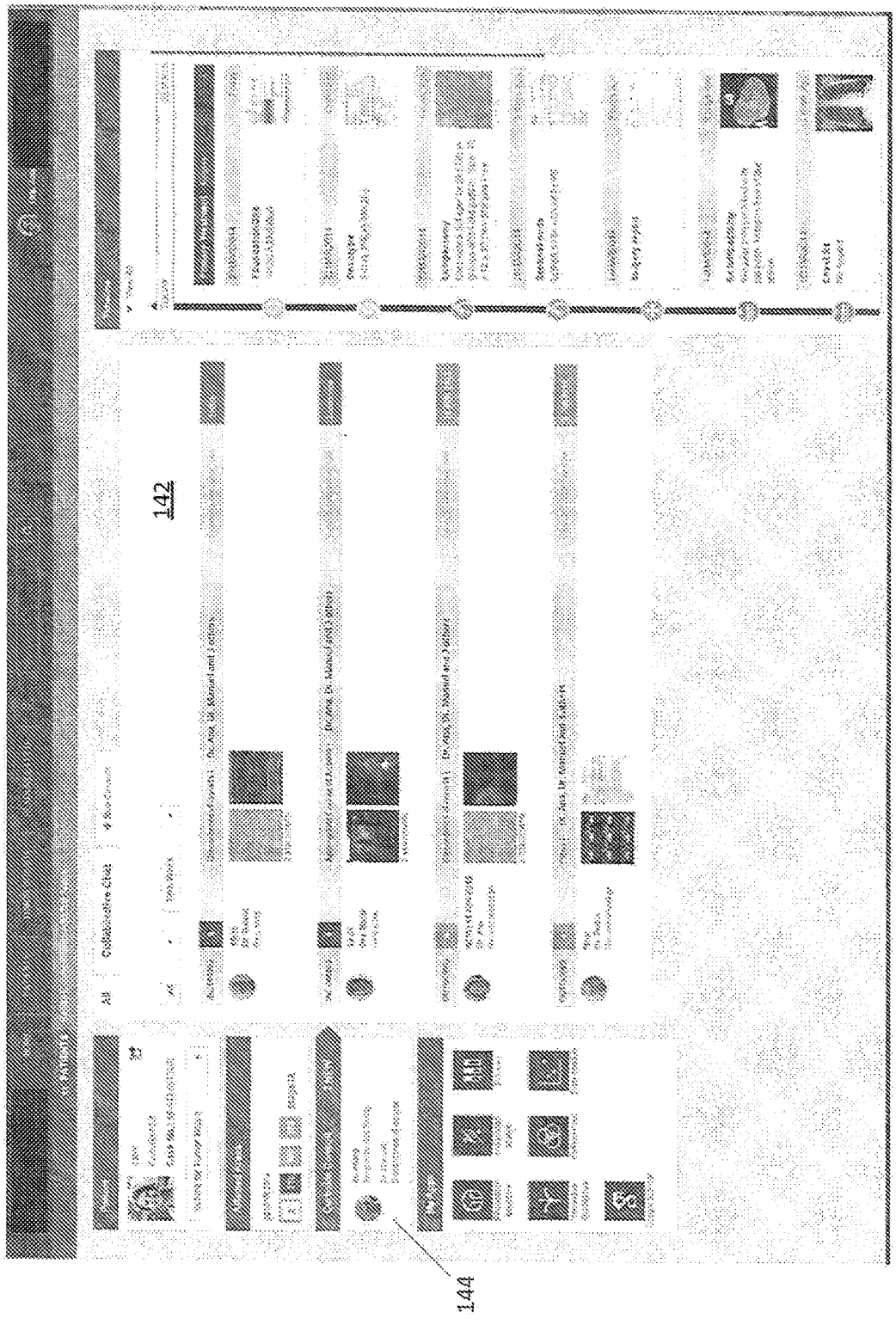
FIGS. 11 and 12 show exemplary screenshots of a GUI displayed by a collaboration tool from the informatics platform of FIG. 3.
Figure 12:
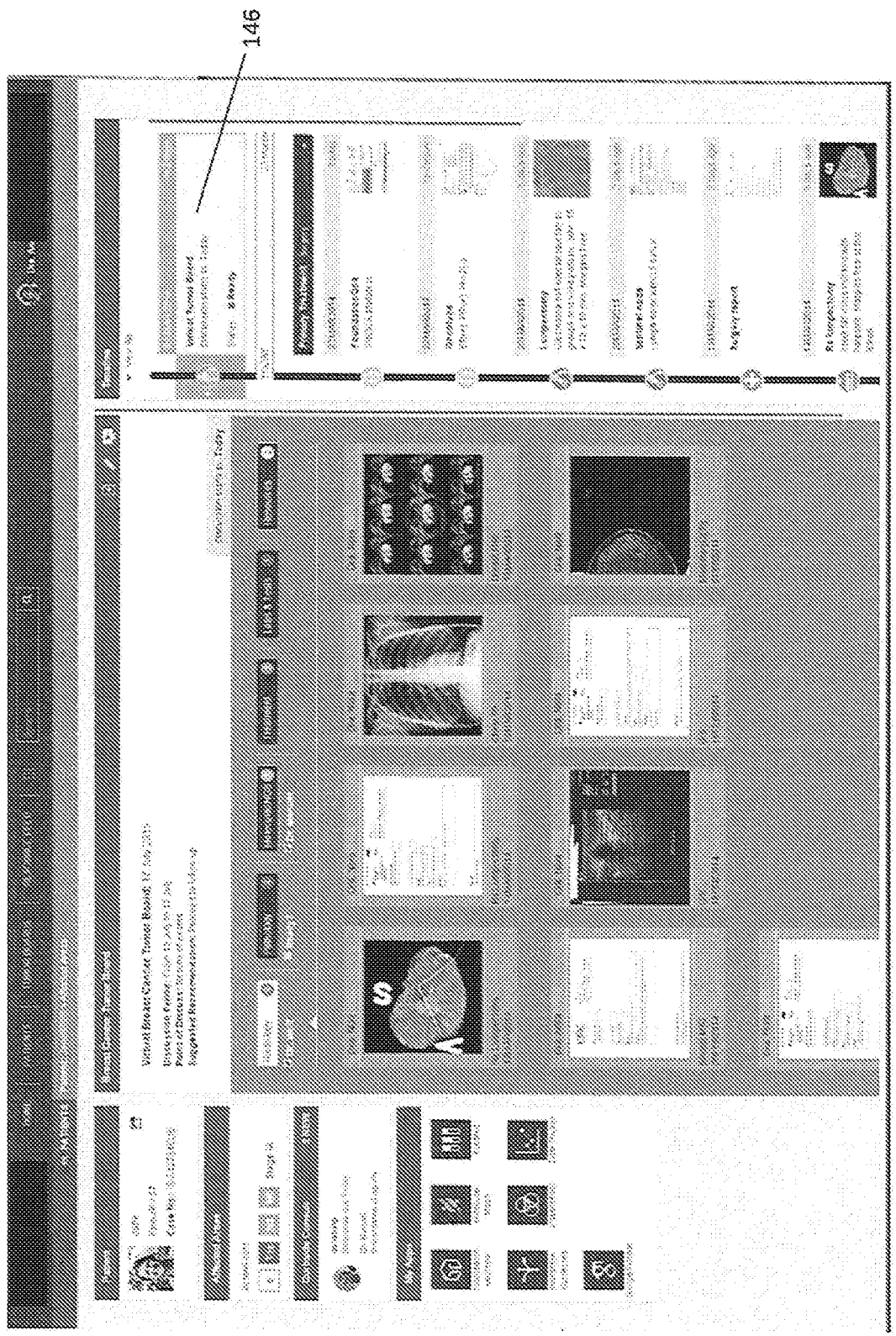

FIGS. 11 and 12 show exemplary screenshots of a GUI displayed by the collaboration tool 60. The collaboration tool 60 provides a communication interface that enables collaboration, both synchronous and asynchronous, among medical personnel. In one embodiment, the collaboration tool 60 can be used with the workflow tool 52. However, in other embodiments, the collaboration tool 60 can be used with other tools of the informatics platform 33 or as a stand-alone tool. The collaboration tool 60 can include a chat interface 142 (see FIG. 11), a consultation interface 144 (see FIG. 11) and a virtual meeting interface 146 (see FIG. 12).

The chat interface 142 enables two or more doctors or other medical personnel to have either synchronous or asynchronous communication among each other. Synchronous communications occur when the doctors or medical personnel are using the chat interface 142 at the same time, i.e., in real-time. Asynchronous communications occur when the doctors or medical personnel are using the chat interface 142 at different times, e.g., offline. In addition to exchanging messages, the chat interface 142 enables doctors or other medical personnel to include contextual patient attributes such as images and reports with a message to be exchanged.

The chat interface 142 can include messaging functionality to permit the medical personnel to exchange messages with each other. In addition, the chat interface 142 can also determine user presence based on the user's login status and can provide other users with the ability to detect when a particular user is accessing the informatics platform 33 and available for collaboration. In addition, the chat interface 142 can be used to share clinical context and information when exchanging messages regarding a patient. The chat interface 142 also provides the ability to save the collaboration sessions and to include the saved collaboration session in a patient's medical record.

The consultation interface 144 enables doctors to request impromptu consultation sessions from one doctor to another doctor in real-time (synchronous) and offline (asynchronous) modes. In one embodiment, the collaboration tool 60 can document the chats and consultations regarding a patient and can include the documented chats and consultations as part of the patient's medical record. In another embodiment, the collaboration tool 60 can determine a doctor's active availability and the best form of communication with the doctor.

The virtual meeting interface 146 may be used to initiate and document an asynchronous collaboration stream for remote or virtual tumor board workflow. In a virtual tumor board, medical personnel can "pin" information, provide contextual overview for their specific discipline and provide a "draft" recommendation form and treatment plan for the board to review. Once all the medical personnel have indicated "readiness" and a "draft" recommendation form and treatment plan is prepared, the virtual meeting interface 146 provides an asynchronous collaboration window to capture any agreement/disagreement among board members and/or notes for each participating doctor. If all board members agree on the "draft" recommendation form and treatment plan, the virtual meeting interface 146 changes the status of the recommendation form and treatment plan to "final" and documents the participating medical personnel and the dialog that determines full consensus. If there is not 100% agreement among board members and the responsible doctor for the patient doesn't want to continue pursuing the "draft" treatment plan with the virtual tumor board, the virtual meeting interface 146 can add the patient to the next physical tumor board. The virtual meeting interface 146 can enable users to review and prepare, offline or asynchronously, for a virtual tumor board and provide respective input for an interactive treatment form or the recommendation form that can occur before the physical tumor board event takes place.

Workflow Tool

The workflow tool 52 enables the preparation, presentation and archiving of information associated with multi-disciplinary tumor boards relating to cancer patient treatment plans. The workflow tool 52 enables medical personnel to: visualize contextual patient data chronologically from disparate information systems 22; access the timeline tool 58 for a visual timeline that allows filtering by department and procedure; access the image viewer 56 that provides basic image manipulation, side by side comparison of images from different specialties and direct access to source information systems 22; visualize relevant clinical information specific to the oncology patient with the ability to drill down for full granular details; access the collaboration tool 60 that provides synchronous and asynchronous communications and the sharing of clinical information; access to patient lists that provide graphical indicators to understand the current state and readiness for a tumor board presentation with an ability to understand the point of discussion at a patient's tumor board; and access an interface to enable tumor board managers the ability to quickly see patients to be discussed, understand preparation requirements and progress, see doctor participation and allocate or schedule meeting rooms and doctor calendars. In one embodiment, the workflow tool 52 can be used for tumor boards for different cancer types such as breast, lung, ENT (ear, nose and throat), GI (gastrointestinal), Gyn (gynecological), Hemo (hematological) and Neuro (neurological).

Figure 13:
FIG. 13 shows an exemplary screenshot of a GUI with a management page displayed by the workflow tool.

FIG. 13 shows an exemplary screenshot of a GUI displaying a management page for the workflow tool 52. The management page 150 provides tools that enable the management of tumor board meeting, provide information on the patients to be discussed at the tumor board events and provide an understanding of the current state of tumor board progress. The management page 150 has one or more sections providing different information and functionality to the user. The management page 150 includes a dialog section 152, an events section 154, a patient list section 156 and a patient card section 158.

The dialog section 152 provides information on tumor board event details, such as the time, date and location of the tumor board, the RSVP status of the user, and the number and status of the RSVPs of the other medical personnel participating in the tumor board.

The events section 154 displays tumor board event details such as the number of cases to be discussed at the tumor board and the readiness, i.e., ready or not ready, of patients to be discussed at the tumor board. The events section 154 also provides the ability to filter the information to obtain more focused results for the user.

The patient list section 156 displays a filterable list of patients by cancer type. The patient list section 156 includes a patient card section 158 for each patient included in the patient list section 106 and to be discussed at the tumor board meeting. The patient card section 158 provides patient details that can include the following: name, gender, age, MRN (medical record number), photo, responsible physician, point of discussion and a readiness counter, which can be similar to counter section 102 and readiness indicator 106 shown in FIG. 7.

Figure 14:
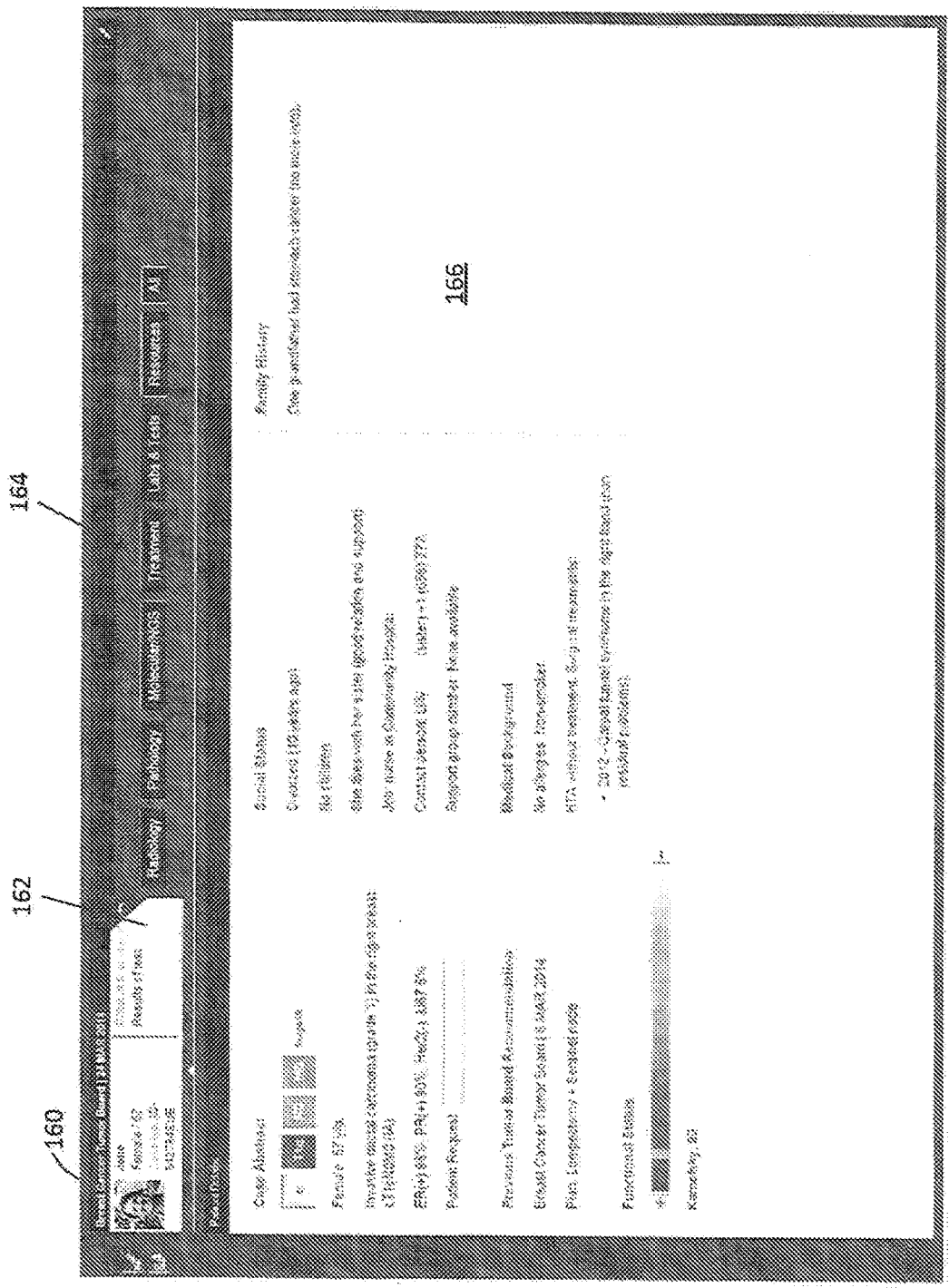
FIG. 14 shows an exemplary screenshot of a GUI with a presentation page displayed by the workflow tool.

FIG. 14 shows an exemplary screenshot of a GUI displaying a presentation page or widget for the workflow tool 52. The presentation page 160 can be used to present the clinical information "flagged" by medical personnel as the most relevant clinical information required by the tumor board to make the most appropriate treatment plan for the patient. The presentation interface 160 has one or more sections providing different information and functionality to the user. The presentation interface 160 includes a patient details section 162, a menu bar 164 and a presentation workspace 166.

The patient details section 162 provides basic patient information to the user and, when selected by the user, provides a detailed patient summary in the presentation workspace 166. The patient summary displayed in the presentation workspace 166 can include details from the patient overview page and contain the summarization of the most recent clinical reports of the patient. In one embodiment, a doctor can prepare/present this information at the tumor board meeting.

The specialty PinBoard menu bar 164 provides "tabs" for several specialty PinBoards that are used to store the pinned or flagged information by medical personnel. In one embodiment, there can be specialty PinBoards for radiology, pathology, molecular/NGS, treatments, laboratory and test results and resources. In addition, there can be an "All" tab that displays the information from each of the specialty PinBoards in the presentation workspace 166. In another embodiment, the tabs of the specialty PinBoards can correspond to the categories of the counter section 102 of FIG. 7. The most relevant clinical images, reports, and related information can be stored in the specialty PinBoards and can be displayed in the presentation workspace 166 when one of the tabs is selected by the user. The presentation workspace 166 displays the associated information for the selected specialty PinBoard and the information displayed in the presentation workspace 166 can be updated by selecting a different tab associated with a different specialty PinBoard.

Referring back to FIG. 4, the patient information page 70 of the workflow tool 52 can provide a summarized glance of a patient such that medical personnel can quickly understand the patient's current status with the ability to drill down to detailed source system detail, if necessary. As previously described with respect to FIG. 4, the summary section 72 can display graphical information that summarizes cancer type, biomarkers, state, tumor size and other parameters. In addition, the workflow tool 52 can include the virtual PinBoard to document and store relevant clinical information, by category, for a patient's multi-disciplinary tumor board as described with respect to FIG. 7, the image viewer 56 as described with respect to FIG. 8, the third party application tool 66 as described with respect to FIG. 10, and the collaboration tool 60 as described with respect to FIGS. 11 and 12.

Search Engine

The search engine 62 incorporates search tools that enable medical personnel to search the database 35 with the aggregated information from the EMR system 20 and the information systems 22. The search engine 62 can be used for an automated similar patient search and a manual interactive similar patient search.

For an automated similar patient search, the search engine 62 uses the search query patterns of medical personnel for a specific cancer type to automate a search query for patients with that specific cancer type based on specific clinical characteristics that may include age, gender, biomarkers, BIRADS classification, staging information, previous treatments, outcomes and family history. The user can edit any of the automatically generated attributes for the search query to obtain the desired search results. From the automated query, the search engine 62 can display patient profiles with similar clinical characteristics, treatments and outcomes. The patient list provides a mechanism for medical personnel to quickly review how other similar patients have responded to prescribed treatments to better understand how a specific patient, with similar clinical attributes, might possibly respond to a particular treatment plan.

The manual interactive similar patient search can be used by clinical researchers, clinical trial principal investigators, or other similar medical personnel to look for "pools" of similar patients based on very specific clinical attributes that reside in the database 35. Medical personnel have the interactive ability to search on very specific clinical attributes such as, age, gender, clinical stage, biomarkers, histology, previous treatments, genomic alterations, and outcomes to find patients that match the selected characteristics or attributes. Medical personnel would have the ability to interactively modify the search queries to narrow or further clarify the results. Additional analysis can be performed on the patients from the resulting search queries and the identified patients could potentially be considered or recruited for clinical trials not previously available during their initial clinical consultations.

Figure 15:
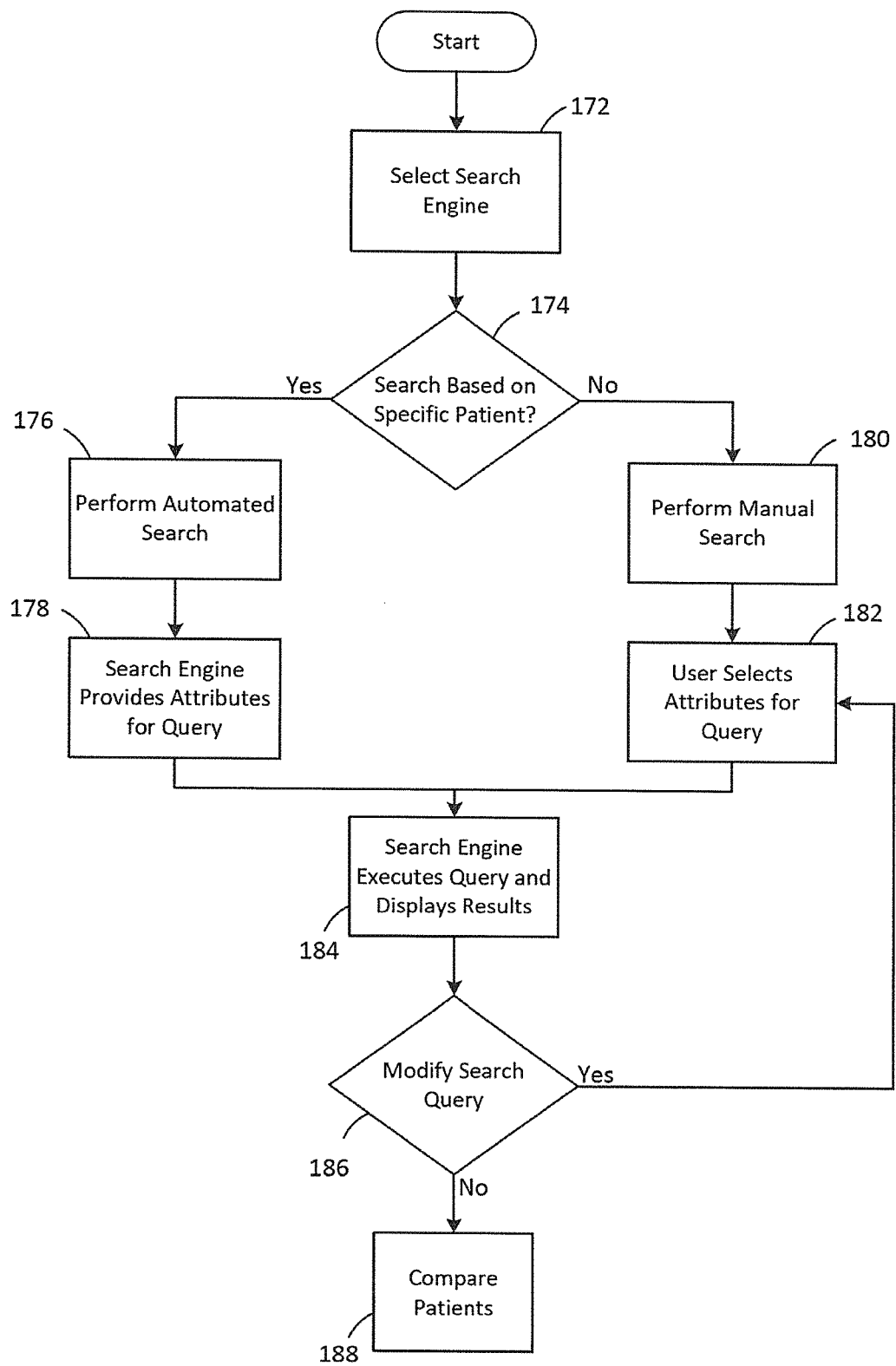
FIG. 15 shows a flowchart of an embodiment of a process for performing a patient search with the search engine.

FIG. 15 shows a flowchart of an embodiment of a process for performing a patient search with the search engine. The process begins with the user selecting or launching the search engine 62 (step 172) to perform a patient search. In one embodiment, the search engine 62 can be selected from either the My Apps interface 132 or the Apps interface 134 of the third party application tool 66. A determination is then made as to whether the patient search is going to be based on a specific patient (step 174). In one embodiment, the determination of whether the patient search is going to be based on a specific patient can be made automatically based on whether the user selects the search engine from the My Apps interface 132 or the Apps Interface 134. Since the applications in the My Apps interface 132 are patient-aware, the search engine 62 would perform the search based on the patient being reviewed. In contrast, the applications in the Apps interface 134 are not patient-aware and thus, the patient search is not based on a specific patient.

If the patient search is to be based on a specific patient, the search engine 62 performs an automated search (step 176) and automatically selects attributes such as age, gender, cancer type, TNM staging, histology, biomarkers and genomic alterations for the search query (step 178). If the patient search is not based on a specific patient, a manual search is performed by the search engine 62 (step 180). For a manual search, the user has to manually select the desired patient attributes to form the search query (step 182). Once the search query has been generated, the search engine 62 executes the search query and displays the results for the user (step 184). If an automated search is being performed, the search engine 62 automatically performs the search once the query is generated. However, for a manual search, the user has to instruct the search engine 62 to perform the search on the generated query. After the search results have been displayed, a determination is made as to whether the search query should be modified (step 186). If the search query should be modified, the search returns to step 182 for the user to select the desired attributes for the search query. If the search query does not need to be modified, the user then has the option to compare information such as treatments and outcomes for the patients identified by the search query (step 188).

In one embodiment, for an automated similar patient search, the search engine 62 can automatically aggregate patient attributes and initiate the query for similar patients without any manual input requirement from the user. In another embodiment, for a manual similar patient search the user has to manually input specific clinical attributes of interest and initiate the query with the search engine 62.

Figure 16:
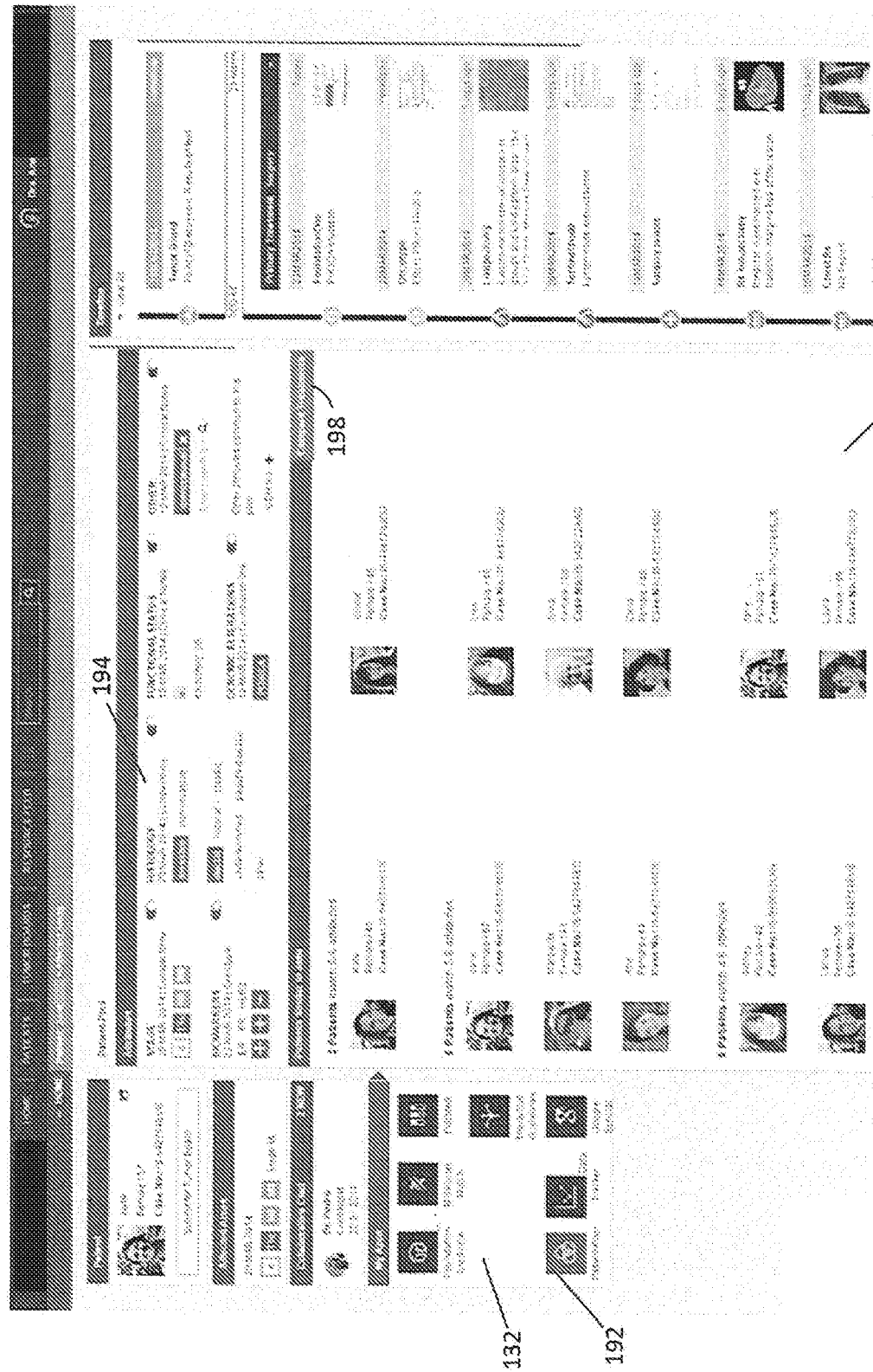
FIGS. 16-18 show exemplary screenshots of a GUI with automated similar patient search pages displayed by the search engine.
Figure 17:
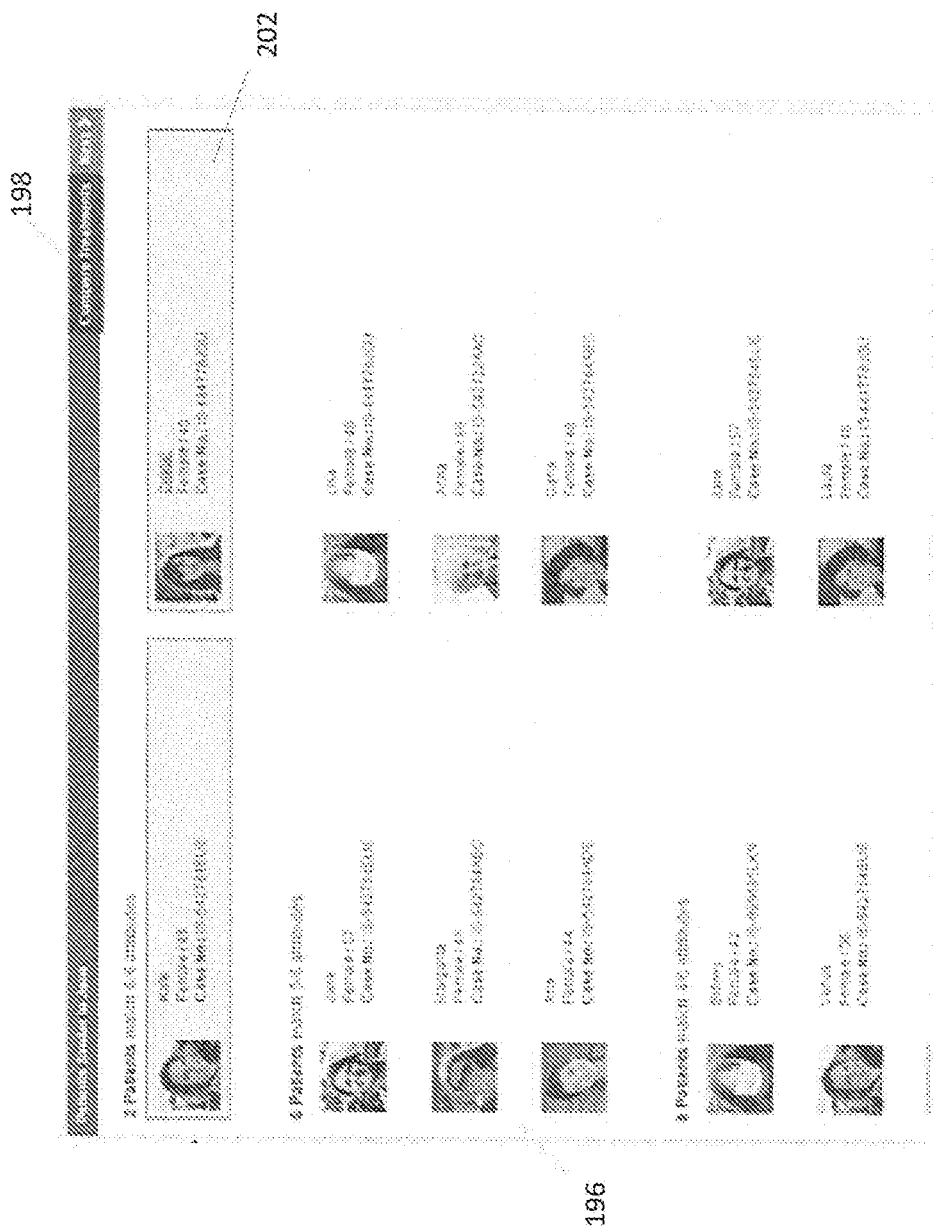
Figure 18:
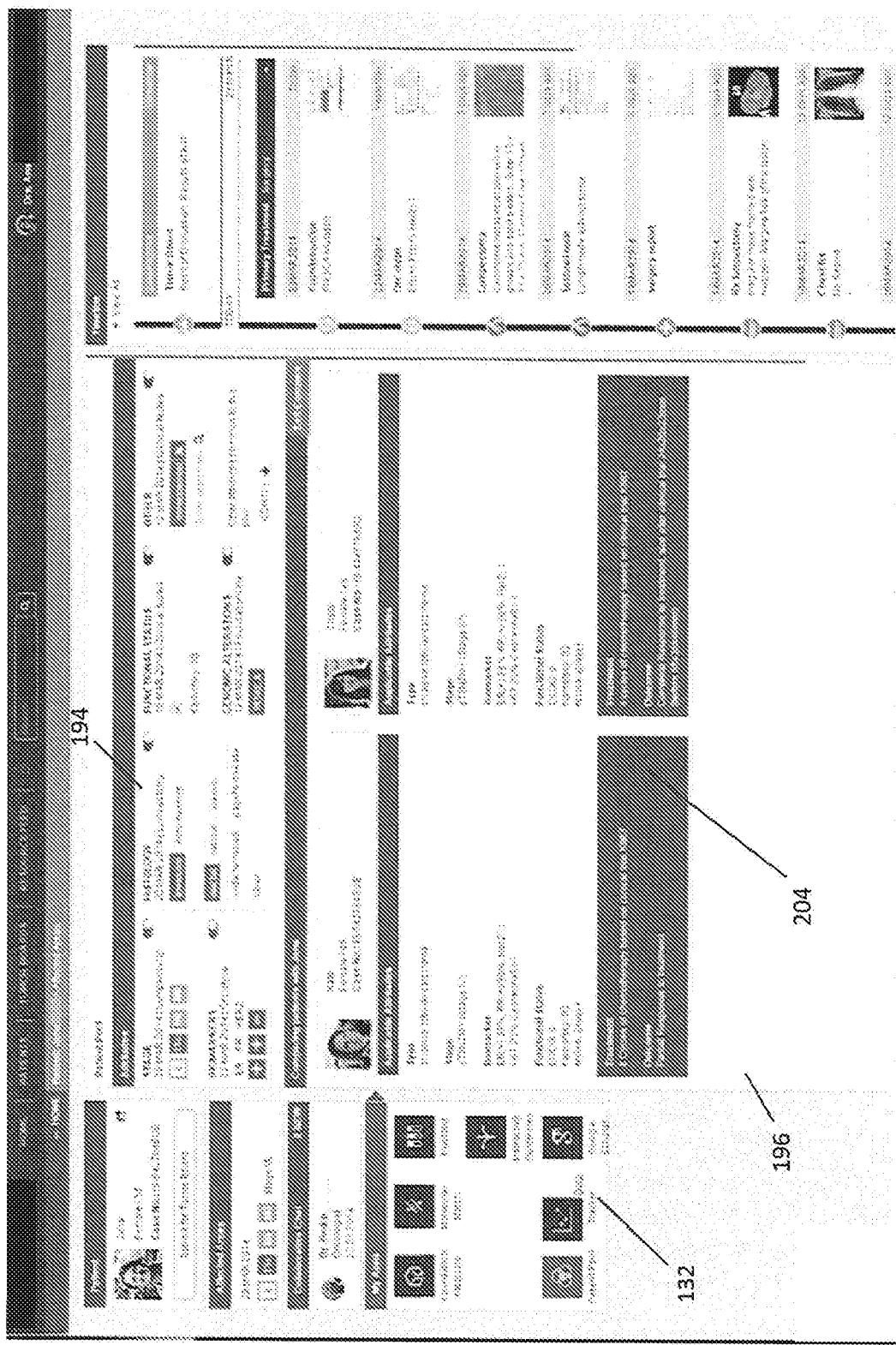

FIGS. 16-18 show exemplary screenshots of a GUI displaying automated similar patient search pages for the search engine 62. As shown in FIG. 16, an automated similar patient search can be initiated by the user selecting the patient pools application or similar patient search icon 192 from the My Apps interface 132. The search engine 62 then selects the corresponding clinical attributes of the current patient being reviewed to initiate a similar patient search query. The selected clinical attributes by the search engine 62 can be displayed in a query section 194. The query section 194 defines the attributes used by the search engine 62 for the patient search and permits a user to edit the attributes used for the search. In one embodiment, the attributes in the query section 194 used to form a search query can include stage, biomarkers, histology, functional status, genomic alterations and other attributes. When the similar patient search icon 192 is selected from the My Apps interface 132 by the user, the search engine 62 automatically generates the search query and performs the search using the generated search query. The results from the search can be displayed in results section 196 for review by the user. The results section 196 can display lists of patients with similar clinical attributes to the patient and permits the user to review all of the results that satisfy the search query. In one embodiment, the results section 196 can categorize the patient lists based on a total number of matched attributes between the patients in the patient list and the specified attributes in the query section 194 (which is based on a specific patient for an automated search) used to initiate the patient search. In other embodiments, the results section 196 can categorize the patient lists based on the specific attribute that is matched or the results section 196 can display a patient list of those patients with attributes that match all or a predefined number of the attributes in the search query.

After the patient lists are displayed in the results section 196, the user then has the option to compare and review how patients in the patient lists have been previously treated and the outcomes of those treatments. To compare and review the treatments and outcomes of selected patients from the results section 196, the user can select the Compare Treatments "button" 198 to initiate the detailed comparison functionality of the search engine 62. Upon selecting the Compare Treatments button 198, the user can then select two or more patients to compare and review in detail. As shown in FIG. 17, the selected patients for comparison can be highlighted for the convenience of the user. A detailed comparison of the highlighted patients 202 can then be initiated by selecting the Next "button."

After the user initiates the detailed comparison of the highlighted patients 202, the results section 196 then displays detailed patient cards 204 for each of the highlighted patients 202 as shown in FIG. 18. The patient cards 204 can provide clinical attribute information that corresponds between patients such as type, stage, biomarker, and functional status and can provide information on the treatments the patient received and the outcomes of those treatments. The inclusion of treatment and outcome information provides historical reference to medical personnel for use in formulating a treatment plan for the patient.

In addition to performing automated similar patient searches, the search engine 62 can also be used to perform manual similar patient searches. The manual similar patient search can be used by medical personnel to search for patients with very specific clinical attributes. Medical personnel may need to identify patients with specific clinic attributes when performing research or finding clinical trials subjects. To initiate a manual similar patient search, a user can select the patient pools application or similar patient search icon 206 (see FIG. 10) from the Apps interface 134.

Figure 19:
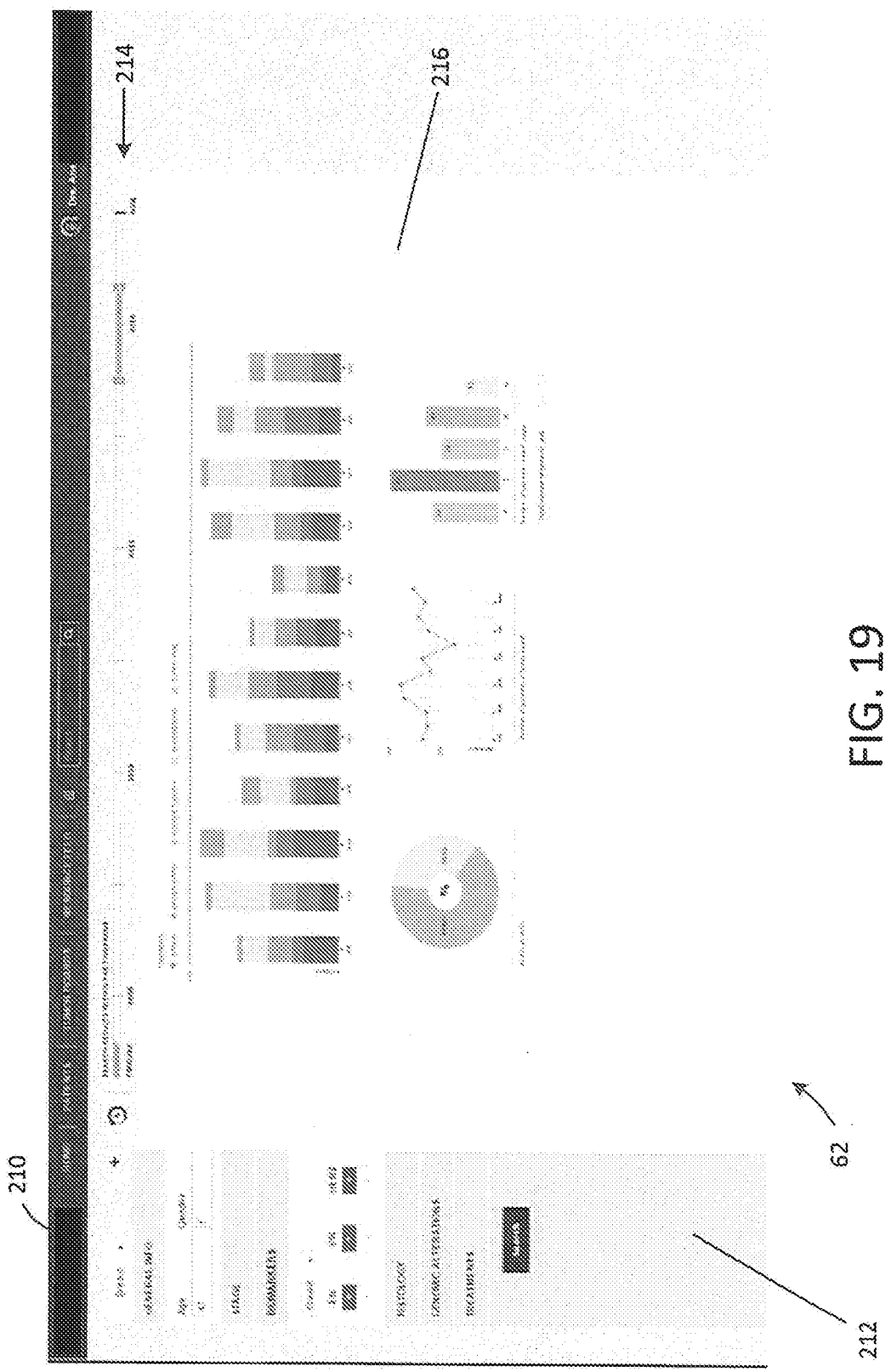
FIGS. 19 and 20 show exemplary screenshots of a GUI with manual similar patient search pages displayed by the search engine.
Figure 20:
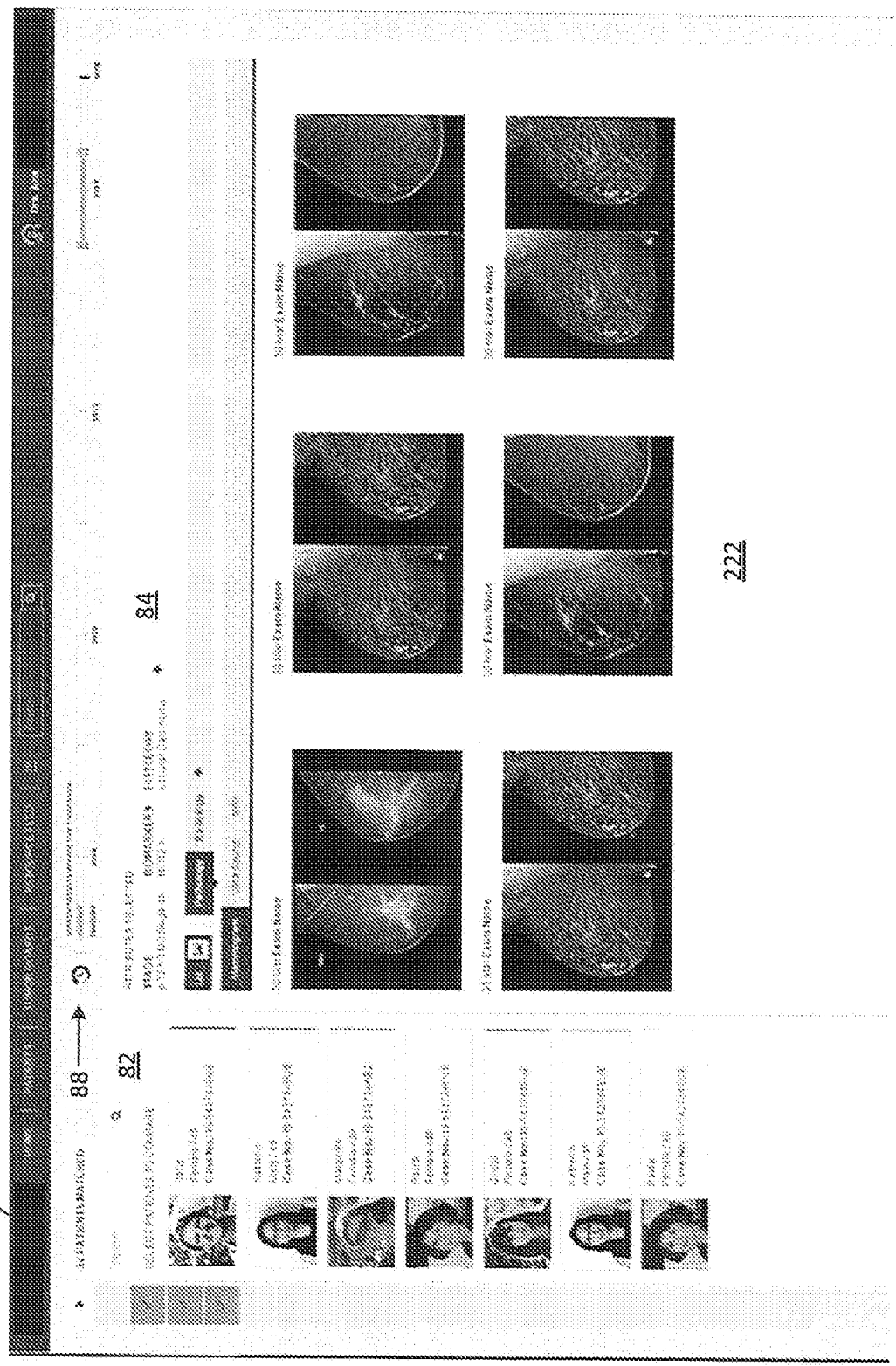

FIGS. 19 and 20 show exemplary screenshots of a GUI displaying manual similar patient search pages for the search engine 62. The manual similar patient search option provided by the search engine 62 permits medical personnel to develop personalized search queries to search the database 35, which includes information from EMR system 20 and information systems 22. As shown in FIG. 19, after selecting the patient pools application or similar patient search icon 206 from the Apps interface 134, the user can be provided with a manual similar patient search page 210 having a query section 212, a date range section 214 and a summary section 216.

The query section 212 provides a listing of several clinical attributes that a user can select from to initiate a similar patient search. The clinical attributes that can be searched include age, gender, stage, biomarkers, histology, genomic alterations and treatment. The user can interactively select any combination of attributes in query section 212 to formulate a search query for the search engine 62. The user can also interactively select a date range defined by years/months/days in date range section 214 to further limit the results from the search query. The date range can correspond to the dates of specific events associated with the patient. For example, the date range can be associated with consultation dates, treatment dates, clinical trial dates, surgery dates and any other event date for the patient. The summary section 216 includes a graphical interface that displays information on the population of patients stored in the database 35. The medical personnel can "mine" the population of patients in the database with specific clinical values or attributes (as established in query section 212) to identify a "pool" of patients that have similar clinical attributes.

Referring back to FIG. 5, the search results page 80 of the search engine 62 can be provided to the user to display the results of the user's search query initiated in query section 212. As previously described with respect to FIG. 5, the attribute selection section 84 can permit medical personnel to view the clinical attributes used to initiate the search query and provide medical personnel with the ability to modify and/or further refine the search query for similar patients. The display section 86 can provide a visual or graphical display of summarized, matching attributes for the similar patients identified in results section 82.

FIG. 20 shows another search results page displayed by the search engine 62. A search results page 220 can be similar to search results page 80 from FIG. 5 and can have one or more sections providing different information and functionality to the user. The search results page 220 includes the results section 82, the attribute selection section 84, a display section 222 and the range selection section 88.

The display section 222 provides the ability for medical personnel to compare other attributes of the patient that include, but are not limited to, radiology imaging, pathology imaging and molecular imaging. The display section 222 can be accessed by a user by selecting an "image button" from either display section 80 or display section 222. Similarly, the display section 80 can be accessed by the user selecting a "chart button" from either display section 80 or display section 222.

The display section 222 can use different categories to organize the information and attributes for display. Some examples of categories can include radiology or pathology. The categories can then be further organized into subcategories to provide more refinement to the displayed results. For example, the pathology category may include categories for mammograms, ultrasounds and MRIs (magnetic resonance imaging). The display section 222 can then display images for the patients in results section 82 for each image type to enable medical personnel to correlate the progression of disease.

Recommendation Form

The workflow tool 52 can include the interactive recommendation form 64. The interactive recommendation form 64 can provide medical personnel the ability to document patient contextual information and the relevant lab reports and clinical tests results that are presented at the tumor board along with structured tumor board recommendations that can be mined for analysis and future disease patterns. The interactive recommendation form 64 provides an interactive ability to include radiology images and reports, an interactive ability to include pathology images and reports, an interactive ability to include genomic sequencing image and reports, an automated ability to include relevant patient information, e.g., age, gender, clinical problems, allergies and current meds, tumor information, e.g., type of cancer, size, location, staging and TNM, and other related demographic information with the ability to edit clinical values, and an interactive ability to easily select cascading, structured tumor board recommendations. The interactive recommendation form 64 can use relevant patient and clinical attributes as key words and auto-populate clinical trials specific to a patient, so the doctor does not have to exit the interactive recommendation form 64. The interactive recommendation form 64 can also provide an interface to document additional clinical tests that can be performed for the patient and can capture the medical personnel that attended the tumor board meeting based on their RSVP to participate.

In one embodiment, the interactive recommendation form 64 can be used by medical personnel during a tumor board meeting to document the discussion and treatment decisions for each patient. At the beginning of or during the discussion of each patient, the user can select the Recommendation Form "button" to open the interactive recommendation form 64 for the patient. The interactive recommendation form 64 can receive information on the patient currently displayed in the workflow tool 52 and then retrieve and aggregate the relevant patient information from the database 35. In another embodiment, the user can select a patient for the interactive recommendation form 64 and the interactive recommendation form can then retrieve and aggregate the relevant patient information from the database 35. The interactive recommendation form 64 can display the most appropriate clinical guidelines from the NCCN, ASCO (American Society of Clinical Oncology), ESMO (European Society for Medical Oncology) or Institution (site configurable) based on the patient's current cancer related attributes and genetic alterations. The guidelines, e.g., the NCCN guidelines, can be interactive and provide visualization to the user as to how the patient's current attributes, staging, treatments align with appropriate guideline.

The interactive recommendation form 64 provides a structure to document treatments (e.g., surgery, radiotherapy, chemotherapy or drug treatment, clinical trial or other therapy) or that no treatment is needed. The interactive recommendation form 64 can be used to indicate additional clinical tests, such as radiology, pathology or molecular/genetic tests, which can be performed for the patient. The interactive recommendation form 64 provides a data structure that can be mined for treatments and outcomes information. The interactive recommendation form 64 also uses relevant patient and clinical attributes as key words to auto-populate a clinical trials section specific to the patient, so the medical personnel does not have to exit the interactive recommendation form to search for clinical trials at a website such as clinicaltrials.gov. Free-text and voice dictated additional notes can be included in the interactive recommendation form to supplement the structured report. After the information has been entered into the interactive recommendation form 64, the information and form can be saved to database 35 to document the collaborative treatment plan for the patient.

Figure 21:
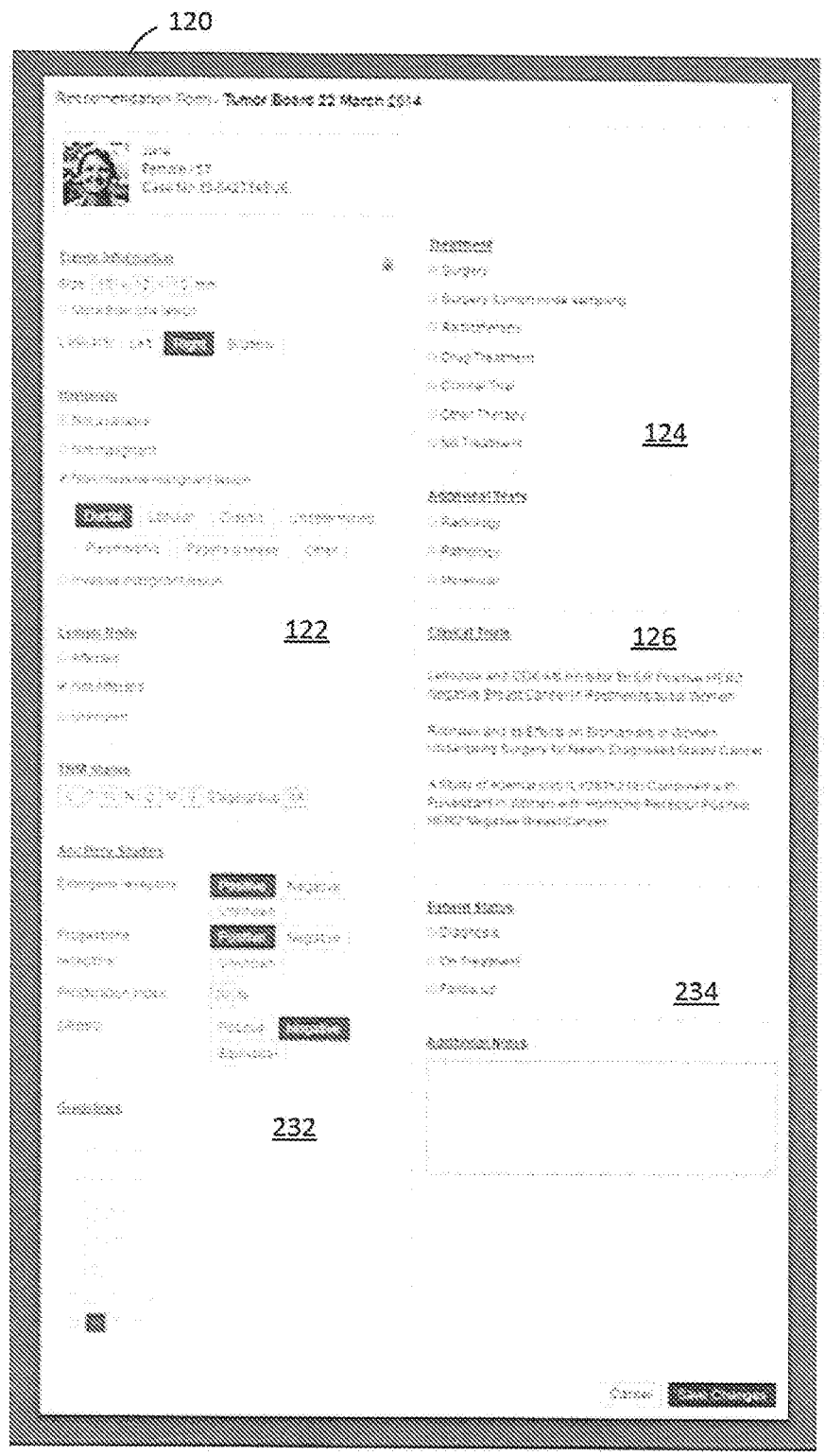
FIG. 21 shows an exemplary screenshot of a GUI displaying the interactive recommendation form.

FIG. 21 shows an exemplary screenshot of a GUI displaying the interactive recommendation form 64. The interactive recommendation form 64 includes the recommendation form interface 120 as previously described with respect to FIG. 9. The recommendation form interface 120 includes the patient information section 122, the treatment section 124, the clinical trials section 126, a guidelines section 232 and an additional information section 234.

The interactive recommendation form 64 can pre-populate patient information, tumor information and demographic information into patient information section 122 using the stored information for the patient in the database 35. In addition, the user can edit the values pre-populated in the patient Information section 122. The treatment section 124 provides a structured interface to document recommended treatments and additional clinical tests that can be performed for the patient and the clinical trials section 126 can be pre-populated with clinical trials for possible participation by the patient. The interactive recommendation form 64 also has the interactive ability for medical personnel to filter patient attributes, e.g., age, gender, type of cancer, gene variants and staging, to refine the search results for clinical trials displayed in clinical trials section 126.

The guidelines section 232 can display the most appropriate clinical guideline from the NCCN, ASCO, ESMO or Institution based on the patient's current cancer related attributes and genetic alterations. In one embodiment, the guidelines section 232 provides the user with access to interactive NCCN Guidelines to provide the medical personnel with a visualization of how the patient's current attributes, staging and treatments align with appropriate guidelines. The additional information section 234 provides an interface to update the status of the patient and to add free-text and voice dictated additional notes to supplement the information in the interactive recommendation form 64.

In one embodiment, the recommendation form interface 120 can include interactive ability to include radiology images and reports, pathology images and reports, and genomic sequencing images and reports as part of the tumor board recommendation. In another embodiment, the recommendation form interface 120 can include the medical personnel that attended the tumor board meeting and involved in the collaborative treatment decision as part of the tumor board recommendation. The information entered into the recommendation form interface 120 can be saved in the database 35 and form part of the patient's medical history and/or record.

Patient Data Tracker

The patient data tracker 54 assists medical personnel with the simultaneous visualization and manipulation of a variety of clinical variables over time. The patient data tracker 54 provides for the graphing of multiple laboratory values over a selected period of time. Additionally, levels of specific patient biomarkers can be graphed and diagnostic images, chemotherapy treatments and other procedures can also be graphed or charted in the same context to provide correlation of data points.

The patient data tracker 54 provides the ability for simultaneous visualization of information from different information systems. For example, the patient data tracker 54 can display line graphs of genetic alteration values from an EMR over a predetermined time period and, at the same time and on the same graph, display white blood cell count results from an LIS over the same predetermined time period. In addition, the patient data tracker 54 can also display tumor size details and the corresponding CT exams from a PACS system on the same graph as the genetic alteration values and the white blood cell count results.

The patient data tracker 54 provides a single interface for medical personnel to access all the relevant data points that have been aggregated into the database 35. Medical personnel can initiate the charting process for a patient by selecting the "data tracker" application from the "My Apps" interface 134 when reviewing information for the patient. The patient data tracker 54 can display a default chart to the user according to a default cancer charting protocol based on the patient's cancer type.

The patient data tracker 54 provides users the ability to interactively display relevant data plots and/or qualitative treatments and examinations. While interactively manipulating the patient data with the patient data tracker 54, medical personal can have complete access to every relevant clinical attribute for the specific patient and can add new and meaningful correlations to the patient data. The patient data tracker 54 can then save the generated charts in the database 35 to preserve the information as a reference for decisions or for patient communications.

When reviewing a patient's relevant clinical information in the informatics platform 33, medical personnel have the ability to initiate the patient data tracker 54 to visualize patient data. To initiate the patient data tracker 54, a user can select the "Data Tracker" application icon 236 (see FIG. 10) from the My Apps interface 132. The patient data tracker 54 is able to aggregate specific clinical values, over time, that relate to the specific cancer type rather than aggregating specific data points.

Figure 22:
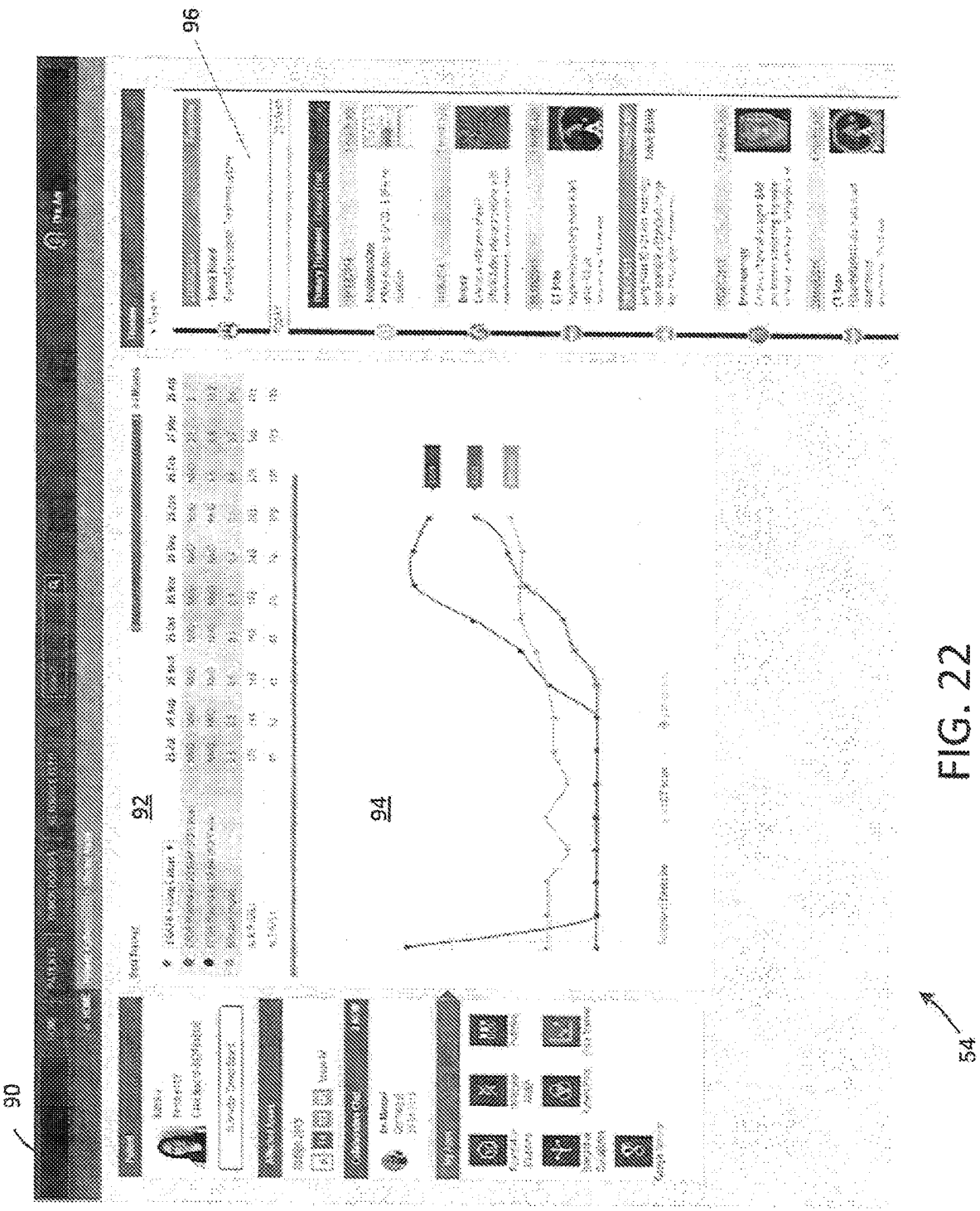
FIG. 22 shows an exemplary screenshot of a GUI displaying the patient data tracker.

FIG. 22 shows an exemplary screenshot of a GUI displayed by the patient data tracker 54. The patient data tracker 54 includes the user interface 90 as previously described with respect to FIG. 6. The patient data tracker 54 provides for the visualization of multiple patient attributes such as laboratory results, images and treatments in a quantitative display (chart) that includes access to qualitative studies. The table section 92 can numerically display multiple clinical laboratory results and related attributes over a predetermined time period. The displayed laboratory results and related attributes in the table section 92 can be obtained from database 35 which aggregates the information from different information systems such as EMR, PACS, RIS and LIS to provide to the table section 92. The charting section 94 can provide for the auto-charting of one or more attribute values from the table section 92 over a predetermined time period in response to the user selecting one or more attributes from the table section 92 for display. The user has the ability to turn on/off the display of individual attributes referencing specific laboratory values in both the table section 92 and the charting section 94. The selected attribute values can be displayed simultaneously in charting section 94 to enable the user to visualize new correlations and relationships among the data. The timeline section 96 can include every clinical test and exam note displayed in charting section 94 and can be accessed by medical personnel at the time of visualization of the attribute values in the charting section 94. The timeline section 96 provides the user with direct access to clinical data, previously accessible only through other information systems, and can immediately reference graphed data and the specific report or laboratory result displayed on the timeline. In one embodiment, the selection of a specific data point on the chart in charting section 94 automatically references the corresponding test/study in the timeline section 96.

Virtual PinBoard

The workflow tool 52 provides a virtual "PinBoard" which enables medical personnel from oncology, radiology, pathology and other contributing departments to designate specific patient data points, such as radiology images, laboratory reports, clinical notes and test results, for discussion at a tumor board meeting. Medical Personnel can "save to Tumor Board" information which can be categorized by clinical domain and numbered to provide tumor board participants the ability to interactively review the preparation status for the tumor board by clinical specialist. Additionally, the virtual PinBoard is saved and documented as supporting evidence for the treatment decision made by the tumor board. Other medical personnel have the ability to reference the detailed clinical information, which provides context to a patient's specific tumor board, in the future as a reference to that patient and in better understanding how other similar patients may be treated.

Figure 23:
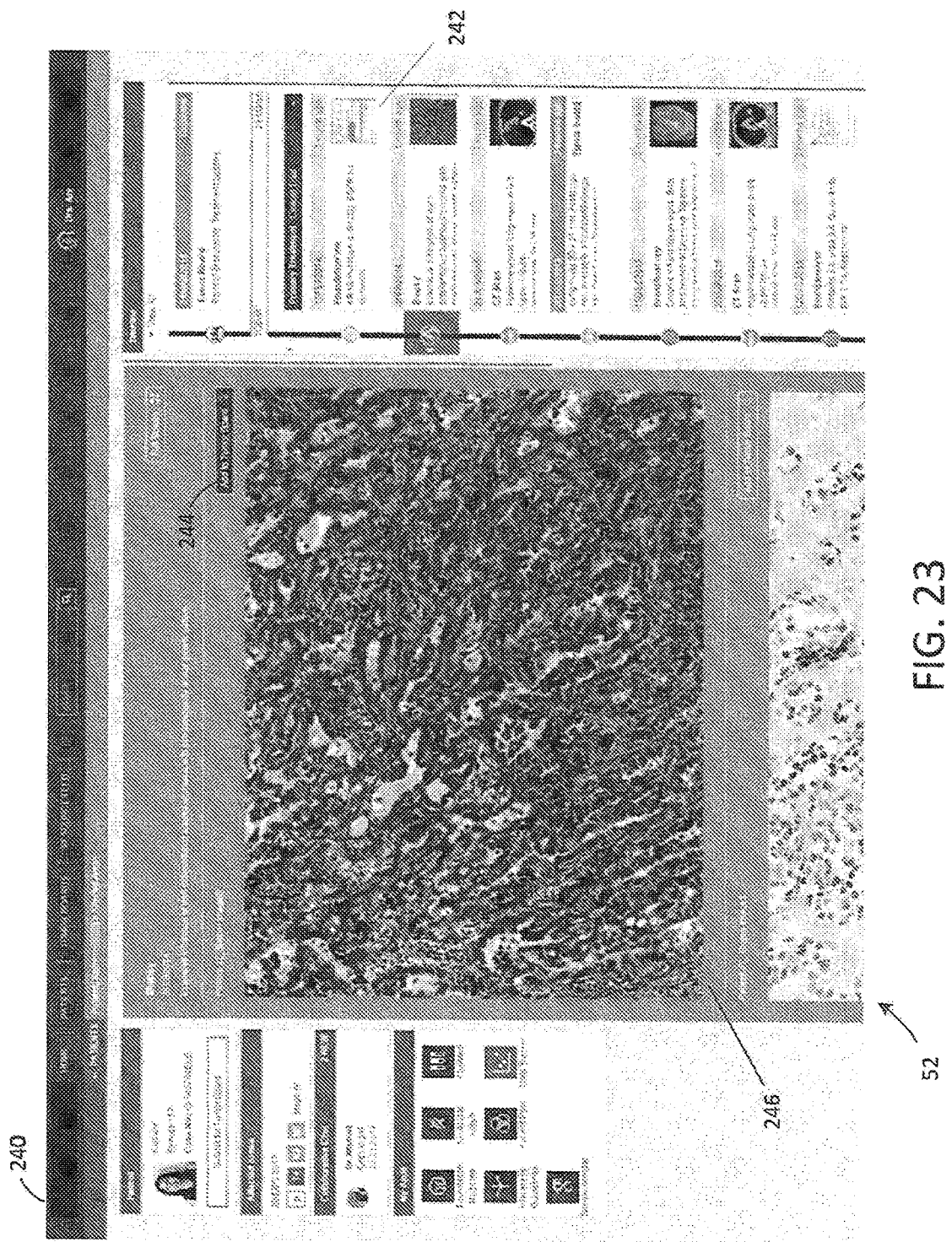
FIG. 23 shows an exemplary screenshot of a GUI with a virtual PinBoard page displayed by the workflow tool.

FIG. 23 shows an exemplary screenshot of a GUI displaying a virtual PinBoard page from the workflow tool 52. The workflow tool 52 provides the virtual PinBoard for documenting and storing relevant clinical information, by category, for a patient's multi-disciplinary tumor board. The workflow tool 52 includes a user interface 240 having one or more sections providing different information and functionality to the user. The user interface 240 includes a timeline section 242, an Add to Tumor Board "button" 244 and a workspace section 246.

The timeline section 242 displays clinical tests, examinations, notes, images and reports from the EMR system 20 and the information systems 22. The user can select one of the items in the timeline section 242 to open a detailed copy of the selected item in the workspace section 246. The workspace section 246 can display the contents of the selected timeline element in more detail. Medical personnel can review the clinical information to better understand the patient's current clinical status. If the medical personnel deems the information relevant or worthy of display at the patient's next tumor board, the medical personnel can select the Add to Tumor Board "button" 244 associated with the information. By selecting the Add to Tumor Board button 246, the user "virtually dog ears" the information and places the information in the virtual PinBoard for later review. The Add to Tumor Board button 246 can be used to store information from the EMR system 20 and the different information systems 22. The virtual PinBoard can automatically categorize the selected item for inclusion based on the department from which the selected item originated.

Referring back to FIG. 7, the virtual PinBoard user interface 100 can provide the user with access to the information selected for the virtual PinBoard. Referring back to FIG. 14, the presentation interface 160 of the virtual PinBoard can provide the user with the clinical information selected by the tumor board members as the most relevant information in formulating a treatment plan for a patient.

Figure 24:
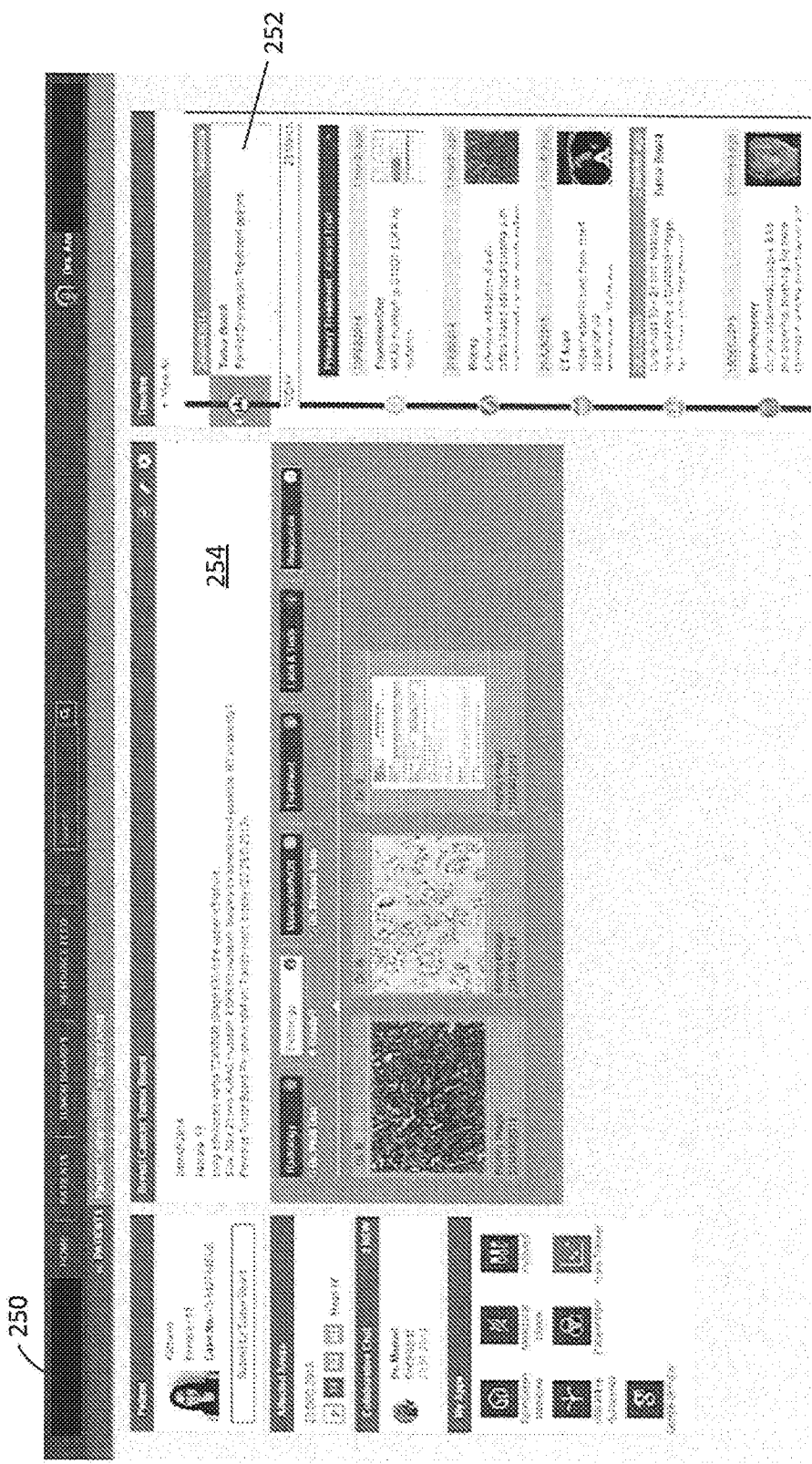
FIG. 24 shows an exemplary screenshot of a GUI with a virtual PinBoard documentation page displayed by the workflow tool.

FIG. 24 shows an exemplary screenshot of a GUI displaying a documentation page from the virtual PinBoard. The virtual PinBoard can be used as historical documentation on the treatment plan for the patient developed by the tumor board. Since the virtual PinBoard serves as a visual storage space for content that was deemed relevant by the participating medical personnel of the tumor board, the virtual PinBoard can also serve to document the clinical artifacts that were presented to the tumor board and contributed to the collaborative decision made by the participating medical personnel of the tumor board. The virtual PinBoard can include a documentation page 250 having one or more sections providing different information and functionality to the user. The documentation page 250 can include a timeline element 252 and a display section 254.

The timeline element 252 can be included as part of the timeline for a patient provided by timeline tool 58 and can be selected by a user to access the virtual PinBoard and display the relevant clinical content for the patient stored by the virtual PinBoard in preparation for the tumor board discussion. In one embodiment, the timeline element 252 can be displayed in the timeline section once information has been selected for inclusion in the virtual PinBoard of a patient by medical personnel.

The display section 254 can display the relevant content specific to the patient's tumor board organized in various clinical categories of information. Under each clinical category, the clinical information that was "Saved for Tumor Board" using Add to Tumor Board button 246 can be displayed in display section 254. The clinical information stored in each of the clinical categories can serve as historical documentation for the clinical context presented and leveraged, by the tumor board, to collaboratively develop a treatment plan for the patient.

Patient Health Status

In one embodiment, the informatics platform 33 can provide information to medical personnel in two broad domains: (1) a general patient health domain; and (2) an oncology-specific patient health domain. The general patient health domain can include information such as the status of allergies, smoking/non-smoking status, current medications, past surgical interventions, and performance status (e.g., Karnofsky, Zubrod, Lansky scoring). The oncology-specific patient health domain can include information such as TNM staging and biomarker status (for hormone, gene and other biological measures such as HER2 status, Progesterone Receptor (PR) antibody level, Estrogen Receptor (ER) antibody level, Ki-67 protein expression level).

The workflow tool 52 can include a visual reference to provide medical personnel with a summary of the patient's health status. The summary of the patient's health status provided by the workflow tool 52 can include information from one or both of the patient health domains. The database 35 can store the information for both of the patient health domains.

To populate the information in the patient health domains stored in the database 35, the informatics platform 33 can use natural language processing (NLP) to extract patient related information and store the information in the corresponding patient health domain in the database 35. For example, the informatics platform 33 can extract oncology related clinical information from the EMR system 20 and the information systems 22, map the information to specific data fields in the database 35 and display the information in a visual summary page in the workflow tool 52. Some of the information that can be extracted from EMR system 20 and information systems 22 and displayed in the visual summary page can include: cancer type and location; type of cancer; biomarkers; treatments; stage of cancer; size of tumor; lymph nodes affected and metastasis.

The cancer type and location information can be derived from radiology and pathology reports and the visual summary page can provide the user with a graphical representation of the anatomical location and type of cancer. In one embodiment, the graphical representation can show medical personnel a patient having breast cancer in the upper left hand quadrant of the left breast. The type of cancer information can be extracted from the core biopsy report and the visual summary page can provide the user with the file name for the report and date of the report as supporting documentation. The visual summary page can also include a hyperlink to directly access the report from the database 35.

The biomarkers can also be extracted or detected from the core biopsy report and the visual summary page can provide the user with graphical positive and negative icons associated with each biomarker to provide a quick, visual reference to aid in cognition and memory by medical personnel. Treatments information, i.e., previous cancer related treatment information, and patient preferences can be extracted from the EMR system 20. Staging of cancer information, i.e., TNM staging values, can be extracted from radiology/MRI reports and the visual summary page can visually display the information to aid in cognition and memory by medical personnel.

The size of tumor (tumor size) information can be extracted from radiology/MRI reports. The visual summary page can include hyperlinks to the MRI images and reports to permit medical personnel to direct access the MRI images and reports from the source PACS system via SSO credentials. The lymph nodes affected information, if identified and applicable, can be extracted from radiology/MRI reports. The visual summary page can include hyperlinks to the MRI images and reports from the source PACS system. Metastasis information, if metastatic cancer has been diagnosed, can be extracted or detected from various radiology images and reports and the visual summary page can provide the user with visual references to the anatomical locations of the affected organs and areas.

Figure 25:
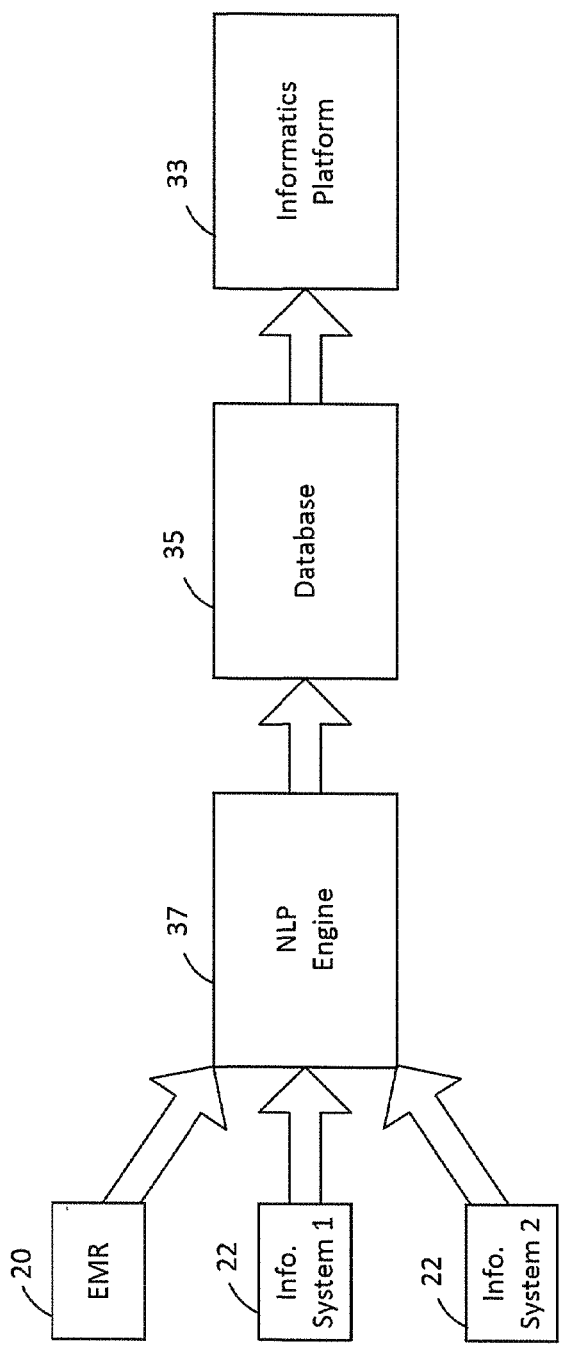
FIG. 25 shows schematically an embodiment of a process for extracting and associating patient data.

FIG. 25 shows schematically an embodiment of a process for extracting and associating patient data. Free-text fields and other information from EMR system 20 and information systems 22, e.g., PACS, RIS and LIS, can be sent to NLP engine 37. The NLP engine 37 can extract and associate the data from the EMR system 20 and the information systems 22. The data extracted by the NLP engine 37 can be mapped or indexed to corresponding data fields in the database 35. The data fields in the database 35 can then be used by the informatics platform 33 to generate the visual references and provide hyperlinks to the source documents.

Referring back to FIG. 4, the summary section or visual summary page 72 provides a visual summary of patient health status along with patient demographics using information in the database 35 obtained from disparate information systems. To access the visual summary page 72, the user can select the "Affected Areas" section or widget 262 (see FIG. 4) of the patient information page 70. The visual summary page 72 can include a visual summary of oncology related details to provide medical personnel a quick understanding of the current clinical state of a cancer patient with minimal free-text comprehension.

Figure 26:
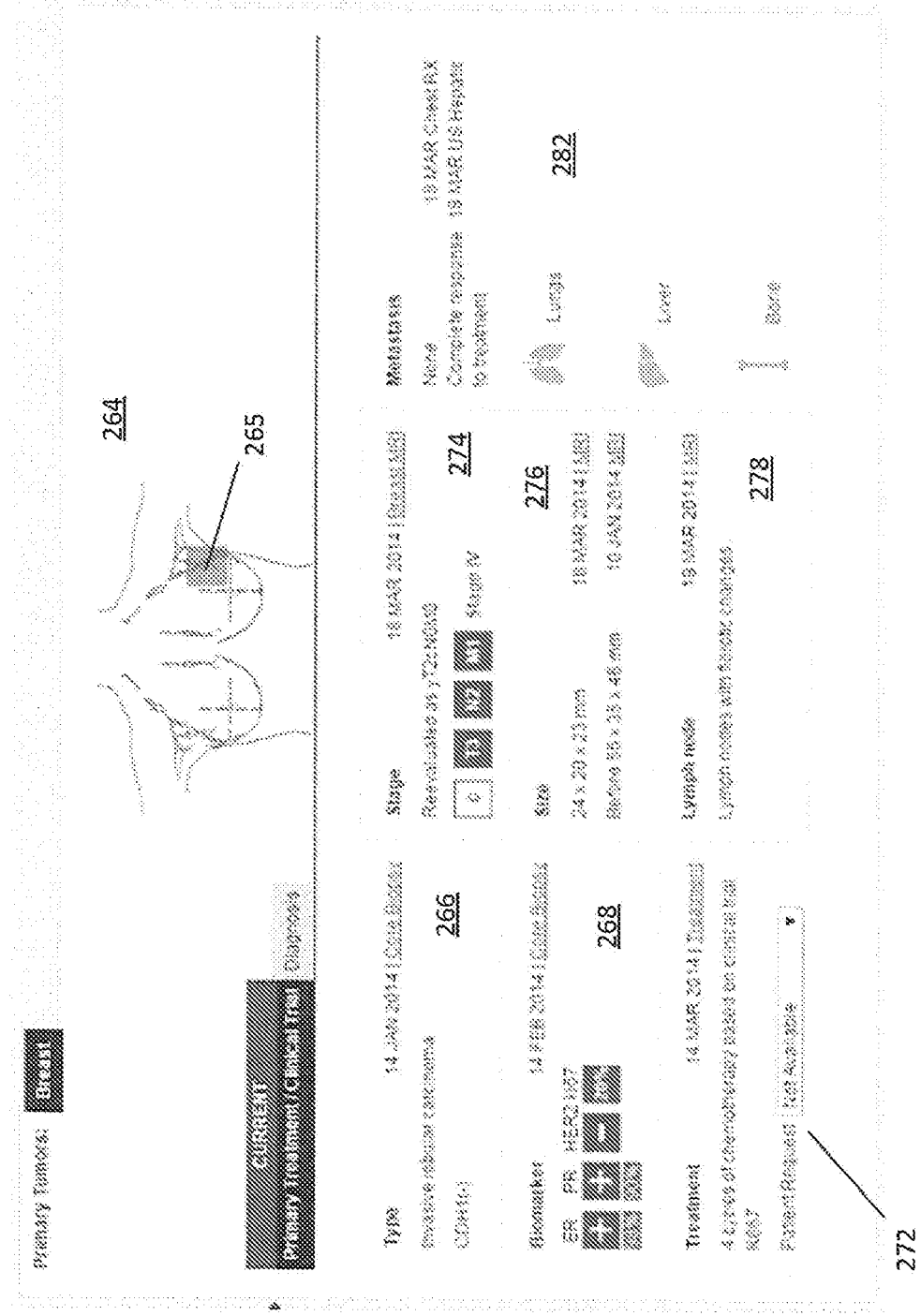
FIG. 26 shows an exemplary screenshot of a GUI displaying the visual summary page.

FIG. 26 shows an exemplary screenshot of a GUI displaying the visual summary page 72. The visual summary page 72 can have one or more sections providing different information and functionality to the user. The visual summary page 72 includes a location section 264, a type section 266, a biomarker section 268, a treatment section 272, a stage section 274, a size section 276, a lymph node section 278 and a metastasis section 282.

The location section 264 can provide the user with a graphical representation of the anatomical location and general type of cancer. The information displayed in the location section can be derived from radiology and pathology reports. As shown in FIG. 26, a highlighted area 265 of the human body can indicate to medical personnel that the patient has breast cancer in the upper left hand quadrant of the left breast.

The type section 266 can display the specific type of cancer and corresponding date information associated with the cancer type information. The type section 266 can include a hyperlink to the core biopsy report that supplied the information used in the type section 266. The biomarker section 268 can include graphical icons providing a positive or negative indication for each displayed biomarker and corresponding date information associated with the biomarker information. In one embodiment, one or more of the icons may have an associated numeric value, e.g., a percentage, for the corresponding biomarker. The biomarker section 268 can include a hyperlink to the core biopsy report that supplied the information used in the biomarker section 268. The treatment section 272 provides information on previous cancer related treatments, any patient preferences or requests that may be associated with the treatments and corresponding date information associated with the treatment information. The treatment section 272 can include a hyperlink to the treatment report that supplied the information used in the treatment section 272.

The stage section 274 can display TNM staging values and corresponding date information associated with the TNM staging information. The stage section 274 can include a hyperlink to the breast MRI report that supplied the information used in the stage section 274. The size section 276 can display information on tumor size (including current and previous tumor sizes) and corresponding date information associated with the tumor size information. The size section 276 can include a hyperlink to the MRI report that supplied the information used in the size section 276. The lymph node section 278 can provide information on any affected lymph nodes and corresponding date information associated with the lymph node information. The lymph node section 278 can include a hyperlink to the MRI report that supplied the information used in the lymph node section 278. The metastasis section 282 can provide visual references to the organs and affected areas having metastatic cancer, if any.

Other Functionality

Figure 27:
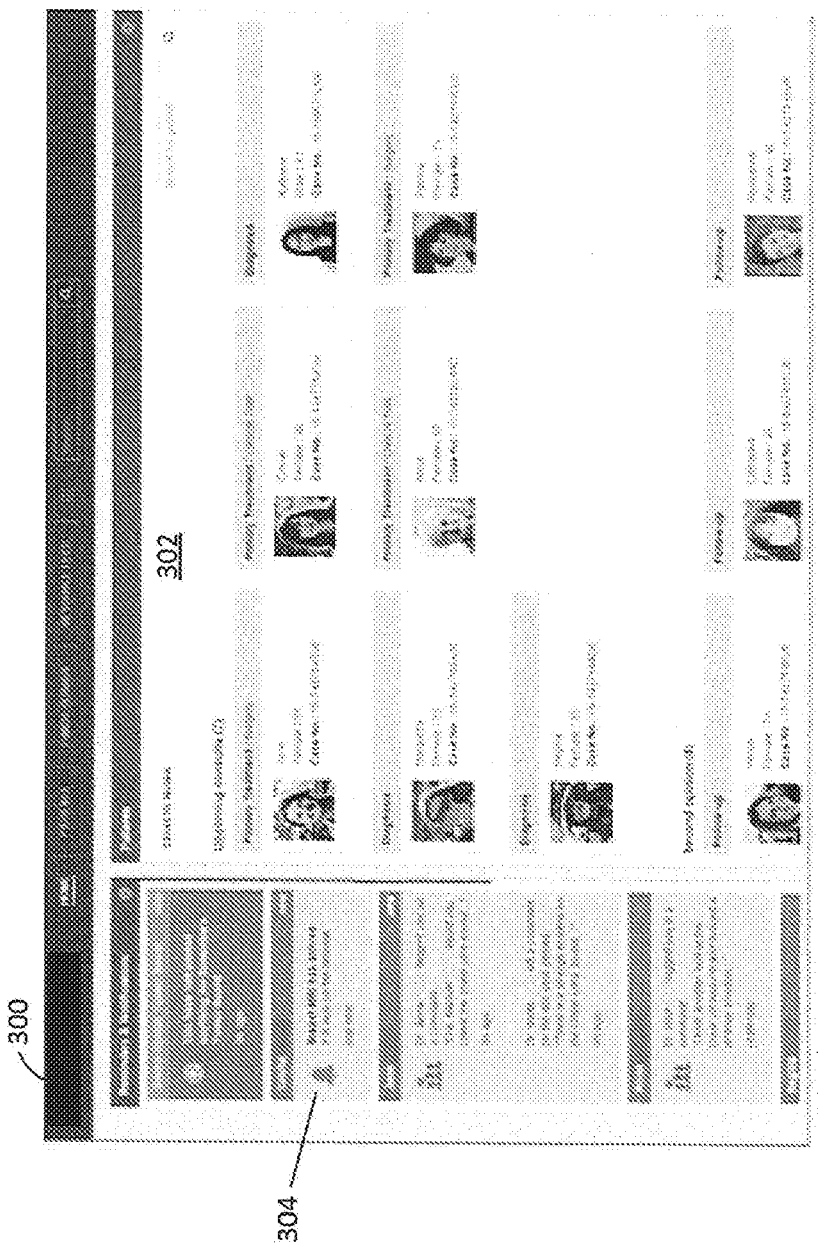
FIG. 27 shows an exemplary screenshot of a GUI displaying a home page from a home tab of the informatics platform.

FIG. 27 shows an exemplary screenshot of a GUI displaying a home page from a home tab of the informatics platform. The home page 300 can have one or more sections providing different information and functionality to the user. The home page 300 includes a patient section 302 and a notifications section 304.

The patient section 302 can provide a doctor with a graphical based list of patients being treated by the doctor. The patient section 302 can include sub-sections that can be used to categorize the patients into different categories. In one embodiment, the patient section 302 can categorize patients into "Upcoming Consults" and "Second Opinions." However, different categories can be used in different embodiments. In addition to categorizing the patients, the patient section 302 can also include some general information associated with the patient for review by the doctor.

The notifications section 304 can display recent notifications for the doctor. The notifications section 304 can provide a notice to the doctor when new clinical data is available for a patient. The notification section 304 can identify the patient and the specific clinical data that is available for the doctor to review. The notification section 304 can also include comments and collaborations with other doctors. The comments and collaborations from other doctors can be identified by the patient to whom the comments and collaborations pertain. The notifications section can also notify the doctor of upcoming tumor boards for the doctor and whether or not the doctor has prepared materials for the upcoming tumor boards.

Figure 28:
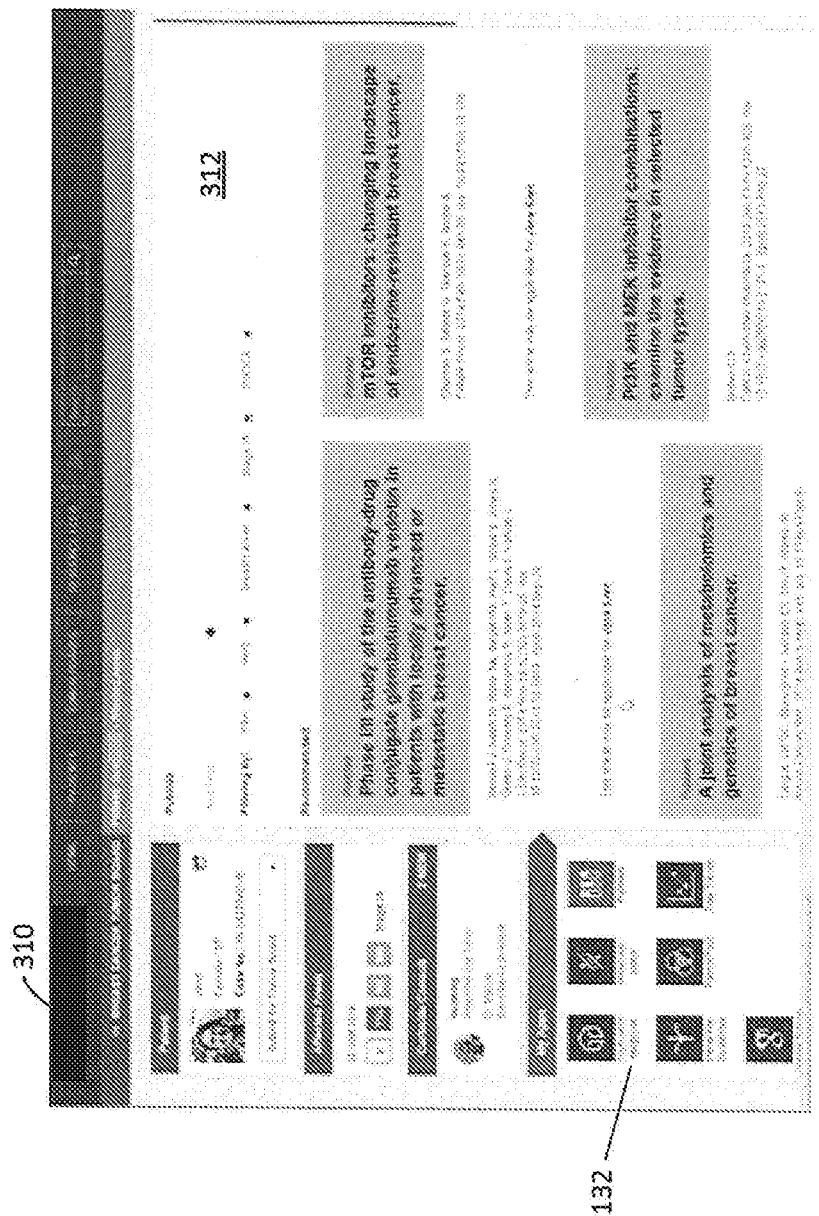
FIG. 28 shows an exemplary screenshot of a GUI displaying a reference page from a third party application.

FIG. 28 shows an exemplary screenshot of a GUI displaying a reference page from a third party application. The reference page 310 can be provided to the user in response to the user selecting a reference application, e.g., PubMeds, from the My Apps interface 132. Once the reference application has obtained the search results based on a search query associated with the patient, the results can be displayed in results section 312. Results section 312 can provide the user with some basic information on the articles that satisfied the search query such as title, authors, publication date and keywords. If the user is interested in a particular article, the user can select the article and be linked to the full text of the article. In addition, the user can be provided with search tools that permit the user to further refine the results.

Figure 29:
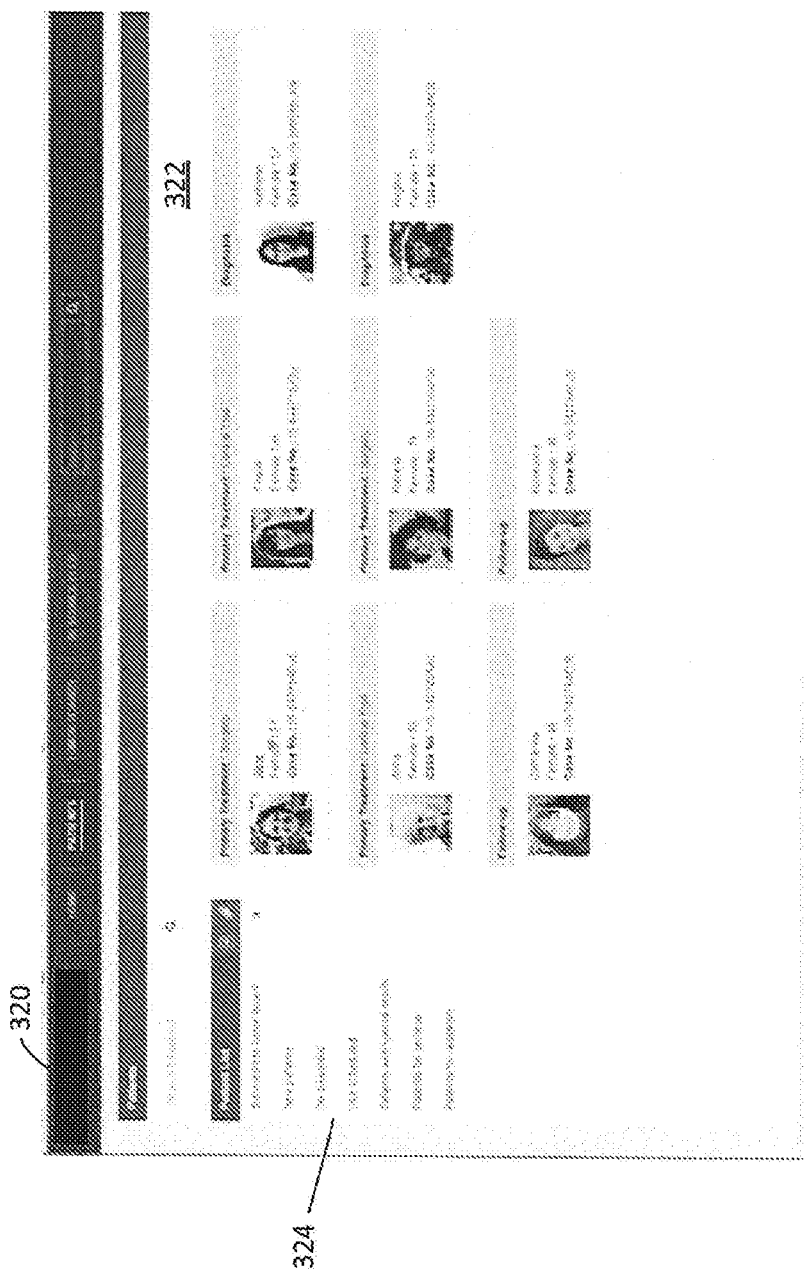
FIG. 29 shows an exemplary screenshot of a GUI displaying a patients page from a patients tab of the informatics platform.

FIG. 29 shows an exemplary screenshot of a GUI displaying a patients page from a patients tab of the informatics platform. The patients page 320 can have one or more sections providing different information and functionality to the user. The patients page 300 includes a patient section 322 and a filtering section 324.

The patient section 322 can provide a doctor with a graphical based list of patients being treated by the doctor. The patient section 322 can provide some general information associated with the patient for review by the doctor. The list of patients in patient section 322 can be based on the filtering specification selected by the doctor in filtering section 324. The filtering section 324 enables the doctor to filter his/her patients into several different categories. In one embodiment, the patients can be filtered according to whether the patients are: submitted to a tumor board; new patients; on treatment; scheduled to visit; patients with special needs; patients for seminar; or patients for residents. Once the doctor selects the desired filtering criteria in filtering section 324, the patients page 320 can display the patients satisfying the associated criteria in patient section 322.

Biostatistical Analysis and Visualization Tool Integrated With Curated Oncology Dataset Currently, treating physicians and diagnosticians (such as, for example, radiologists, endocrinologists, pathologists, etc.) are trained to follow evidence-driven medical decision-making guidelines. These guidelines cover a wide range of medical conditions and are useful in ensuring that the best evidence is used for the broadest number of patients. Evidence-based guidelines rank evidence quality based on the source from which the evidence for or against a treatment is generated with double-blinded, placebo-controlled Phase III clinical trials ranking highest, and individual "case reports" falling near the lowest level of acceptable evidence.

While guidelines provide physicians with a range of options that cover the needs of many patients, there remain difficult situations in which a patient's case may not clearly fall within a single guideline-based recommendation and may instead represent an ambiguous or complex case in which a physician's reliance on evidence (as defined by typical clinical guidelines) is either conflicting or otherwise absent.

Kaplan-Meier survival curves and other types of biostatistical analytic tools are typically run only during a clinical trial and would not be accessible to patients that are not participating in a clinical trial. Manually plotting a patient's clinical attributes against existing clinical trials biostatistics would be a tedious task and is not a standard of clinical care.

In such cases, clinicians would benefit from the ability to interrogate a data set of similar patients (i.e., patients with a similar condition or disease state, medical history, family history, or other characteristics) who have been treated in the past (but were not a part of a clinical trial or other organized study) in order to determine to the extent possible how the treatment of those patients affected their outcomes (either positively or negatively) over time.

The present application also generally relates to systems and methods which enable physicians to collect and analyze a large pool of patient data. By enabling physicians with the ability to quickly and seamlessly interact with large volumes of underlying data and to access the insights contained within these data in an intuitive manner that does not require advanced statistical training, this application (1) allows physicians to access the best available evidence for difficult treatment decisions in cases where more reliable evidence may not exist; (2) enables physicians to interact with one another and collaborate with researchers in a manner that complies with health data privacy regulation; (3) enables hospitals, healthcare institutions (such as insurers and government agencies), and life science research entities to interact with physicians and more readily understand what evidence gaps may be impacting treatment decisions as well as what evidence physicians themselves are able to uncover using the systems and methods disclosed herein.

Currently, statistical analysis of health-related data is an activity that is separated from those activities related to clinical care. The workflow today relies on the following stepwise process: 1) gathering data from one or multiple sources; 2) collating data in a manner that allows multiple sources to be used together; 3) querying the collated data to determine whether it contains a sufficient quantity of data points that relate to a question or hypothesis at hand; and 4) using the available data and apply a statistical model or analytic tool in a manner that generates insight or an answer to the question or hypothesis.

The present disclosure describes a "data hub" which automates steps (1) and (2) allowing those steps to be performed "in the background" each day as clinical care is delivered. In one embodiment, the data hub comprises a system that extracts data and collates it automatically without intervention from the end user, prior to any expressed need for analysis or inquiry. In this embodiment, the data hub represents an automatically gathered data pool, designed to address future clinical questions. When such questions arise, a researcher or even a clinician can use the presently described interactive toolset to query the data hub and determine whether sufficient data exists on a given question or hypothesis. For example, a physician may already know that a particular test will help her determine if patients are likely to respond to a specific, targeted drug. However, the physician may want to know whether the test also predicts side effects in older patients. Specifically, when the test result value is over a specific threshold, does a the diagnostic test in breast cancer for women over the age of 60 with no prior history of smoking but a previous diagnosis of colon cancer predict side effects as well as drug efficacy?

In one embodiment, the analytics described herewith enables novice users to apply complex statistical models in standard, well-understood and well-characterized settings so that non-expert users can determine whether a particular analytic tool (1) yields a valid insight and (2) whether that insight is meaningful. Consider the prior hypothetical example: the data hub contained approximately 300 women meeting the selection criteria for the question at hand. Applying an Odds Ratio (OR) analysis, it is determined that the side effects are twice as likely among patients whose test values were above a specified cutoff threshold compared with those whose tests were below the threshold or otherwise 'negative.' However, the probability of this result based on the data available in the data hub was just over 5%—a level of likelihood that is flagged as unacceptably high.

In the above example, the disclosed analytics allows a non-statistician to determine that although the data suggest that a particular test may predict side effects the data are not in fact robust enough to support this hypothesis. Here, a physician has tested "a hunch" about something that has not been fully researched. This hunch might otherwise have been acted on without data were the data hub and analytics suite not been available. With these tools in hand, the physician is able to readily query the available data and determine that this particular hunch is reasonable—but not properly substantiated by the data available at this time.

In one embodiment, the disclosed interactive application enables physicians to leverage the population of patients contained within the server and leverage this data to populate biostatistical models that chart out potential outcome, latency and other predictive models that leverage oncological nomograms that are open source and commercially available as industry recognized as standard of practice. Exemplary biostatistical models & nomograms may include, for example, the Kaplan Meier Survival Analysis, a cox proportional hazard regression, outcome models, an odds ratio, a hazard ratio, a risk ratio, an absolute risk reduction, sensor sensitivity and specificity analysis, latent variable models, predictive models, and so forth.

In one embodiment, the presently disclosed server contains comprehensive patient data from multiple institutions. Such data may originate, for example, from the EMR, Radiology, Pathology and Laboratory information systems which have been curated from an oncology perspective. Leveraging this dataset, clinicians and researchers have the ability to aggregate very specific clinical attributes/values that are common from de-identified patients residing on the server to identify single patient types or populations or patient types.

In an additional embodiment, the disclosed system will leverage existing open source and commercially available biostatistical models and nomograms and provide an interface for clinicians and researchers to interactively select one or multiple models to explore with the system dataset. An interactive wizard will provide a means for the system to pre-populate values required by a biostatistical model that exists, in a structured means, in dataset. The wizard will also provide a useful technique for the clinician/researchers to modify clinical values to provide a method to "experiment" with the generated results and patient populations.

Once the clinician/researchers have completed their experimentation in exploring the generated datasets and identified patient types, they can accept the clinical values in the wizard, which causes the system to calculate and generate the resulting plotted analytical graphs. The graphs may be customized to provide for a technique to determine population of patients response, individual patient response and/or a hybrid combination Once a graph has been plotted, researchers and clinicians have the ability, through an interactive interface, to further modify the clinical attributes and update the graphs to better understand the effects of modifying treatments, etc. Users have the ability to save multiple variations of plotted graphs to the system to an individual patient's record or to the individual researcher's database of interesting cases.

Researcher and clinicians are also able to share saved plotted explorations with colleagues within their institution or outside for consultative purposes. The disclosed system comprises an interactive interface that will allow collaborators to confirm, comment or further modify the plotted explorations. Outside users will have the ability to save and return modifications to the researchers and clinicians that initiated the query to follow-up or close on the dialog.

Figure 30:
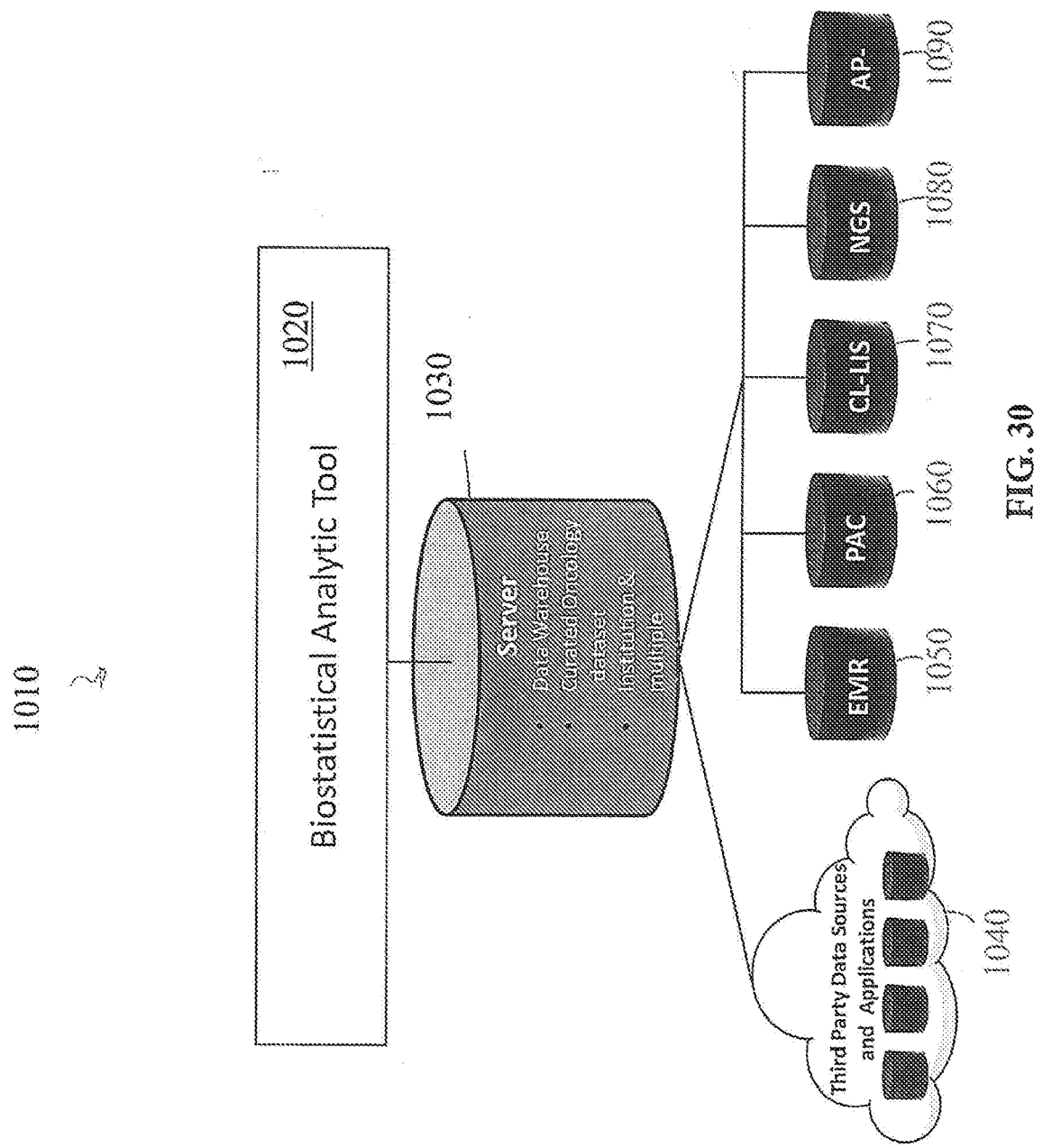
FIG. 30 is a diagram illustrating an exemplary biostatistical analytical tool of the present disclosure atop a curated oncology dataset.

FIG. 30 illustrates the presently disclosed system 1010 comprising a biostatistical analytical tool 1020 integrated with a curated oncology dataset 1030. Here, the server 1030 integrates with the a plurality hospital IT systems, for example, EMR 1050, PACS 1060, CL-LIS 1070, Next Gen Sequencing 1080, AP-LIS 1090, etc. The server 1030 also integrates with online, third party references such as, for example, PubMed, Up-to-Date, clinicaltrials.gov, etc. (not shown). The platform is software based and provides the ability to provide workflow and visualization of Oncology Patient Clinical Information all originating for the disparate IT systems listed above. The biostatistical analytic tool 1020 provides automated and semi-automated queries of the curated dataset and leverages biostatistical models to generate analytical graphs that relate to predictive, potential outcome, latency, remission for a patient or pools of patients.

Figure 31:
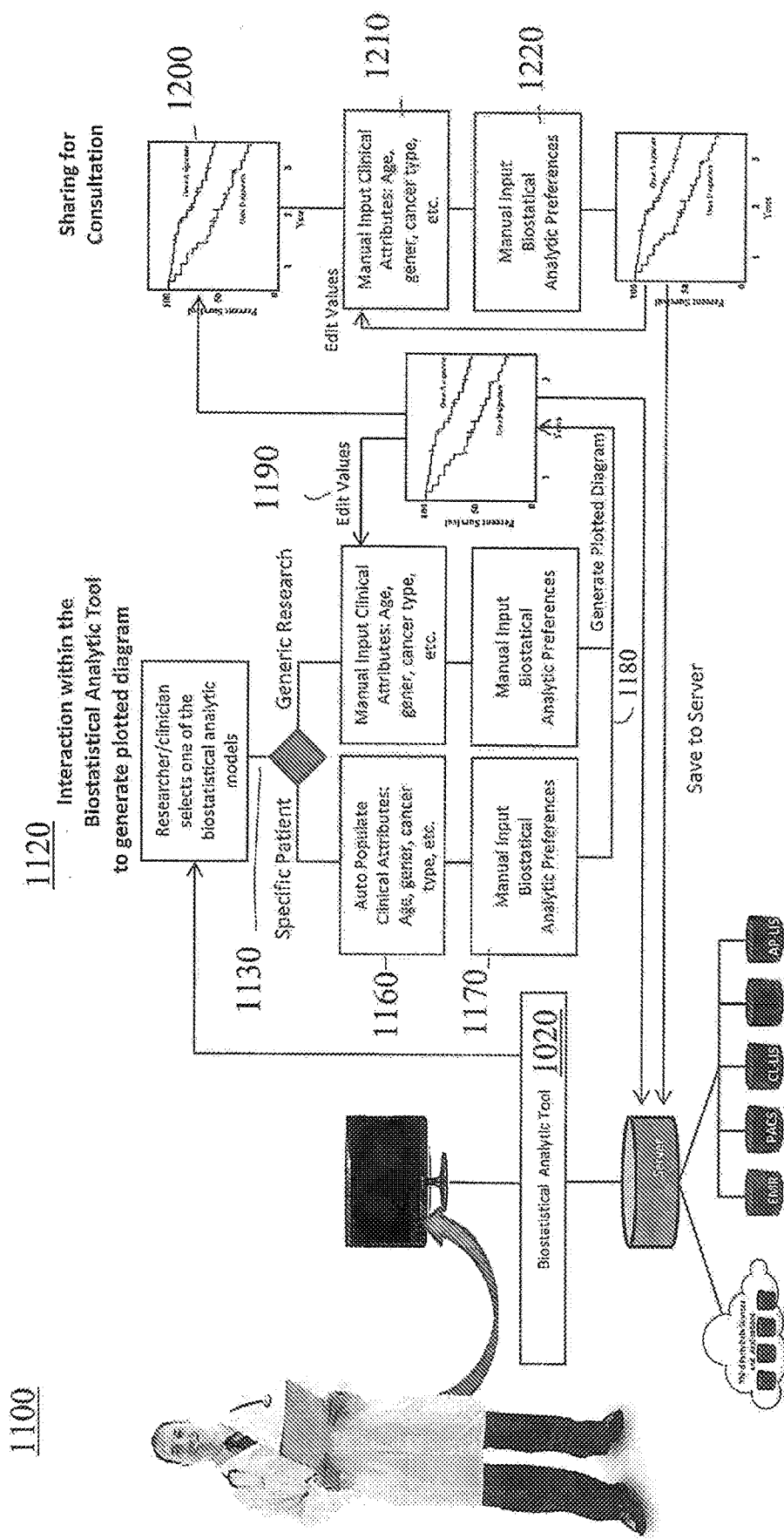
FIG. 31 is a diagram illustrating an exemplary researcher/physician workflow.

FIG. 31 is a flow diagram illustrating an exemplary researcher/clinician workflow which leverages the biostatistical analytical tool 1020 within the system 1010. At step 1100 the researcher/clinicians access the software application that accesses anonymized & curated patient data for an institution of multiple institutions. Presently, the focus of data and analytics companies is on mining the Electronic Medical Record (EMR) alone. The present method utilizes other types of patient data (see FIG. 30).

Moving to step 1120, the researcher/clinician is able to access the biostatistical analytic tool 1020 from the generic applications widget in the title bar. This step occurs within the software application. Clinicians focusing on a specific patient (step 1130) have access to a number of open-source and commercially available biostatistic analytical models 1140, 1150. The clinician the selects the model that is of interest for example the Survival Analysis: Kaplan Meier (not shown). The system 1010 auto populates relevant clinical values such as Age, Gender, Type of Cancer, biomarkers, etc. (step 1160). Researchers that are more focused on pools of patient types would manually input clinical values that relate to the population of patients that they are interested in further interrogating the data (step 1170).

Referring to step 1180, the system 1010 provides a wizard that allows the clinician the ability to interactively select attributes of the plotted chart. The clinician then has the ability to preview the plotted chart or further modify the attributes to better hone the resulting chart (step 1190). Once a plotted graph has been rendered the researchers or clinicians are able to do the following: (1) save various states of the plotted graph to a patient's medical record or for the clinicians teaching files (not shown); (2) further modify the plotted graphs by editing, modifying previewing various states of the plotted graph (step 1210 and 1220); and (3) send the plotted graph, with full interactive data, to colleagues for confirmation, discussion or further modification (step 1200). Consulting physicians have the ability to further modify the plotted graphs and send their results to a patient's medical record (steps 1210 and 1220).

Figure 32:
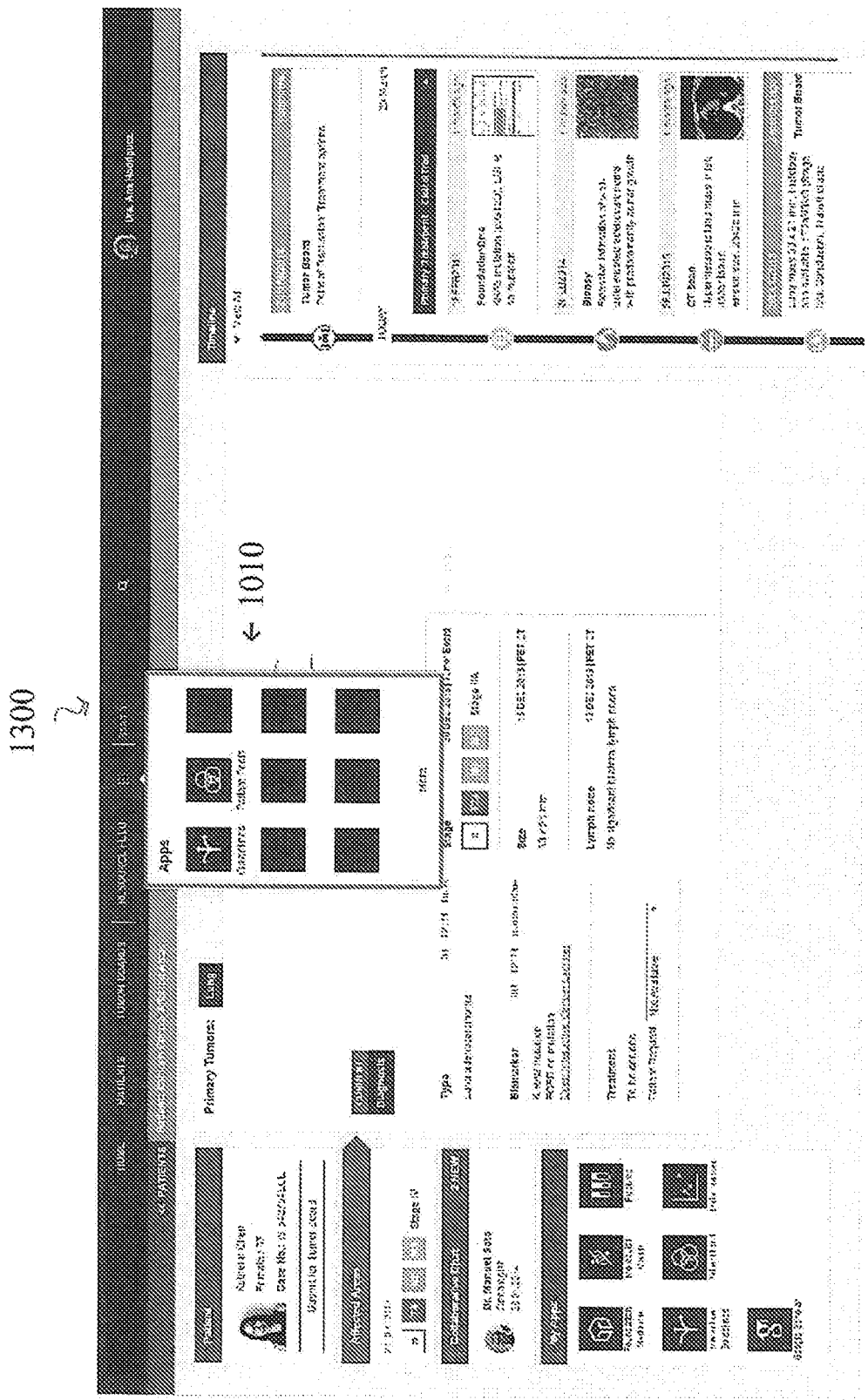
FIG. 32 is a diagram illustrating an exemplary application widget.

FIGS. 31 and 32 describe the generic research widget 1300 of the present system 1010. The system 1010 provides an open architecture that not only enables internal and external third party developers to leverage for their application, but also provides the ability to leverage clinical contextual data pertaining to a specific patient to be leveraged by these applications. No additional work to input data is required when accessing these applications.

Referring again to FIGS. 31 and 32, the generic application widget 1300 comprises the area where applications are displayed and are accessible to end users. These applications are not "patient-aware" and require the user to input additional values to initiate the interaction with the application. The researcher clicks on the biostatistical analysis tool 1020 which would be accessible via the generic application widget on the title bar of the application. The biostatistical analysis tool would launch in the workspace of the application.

Figure 33:
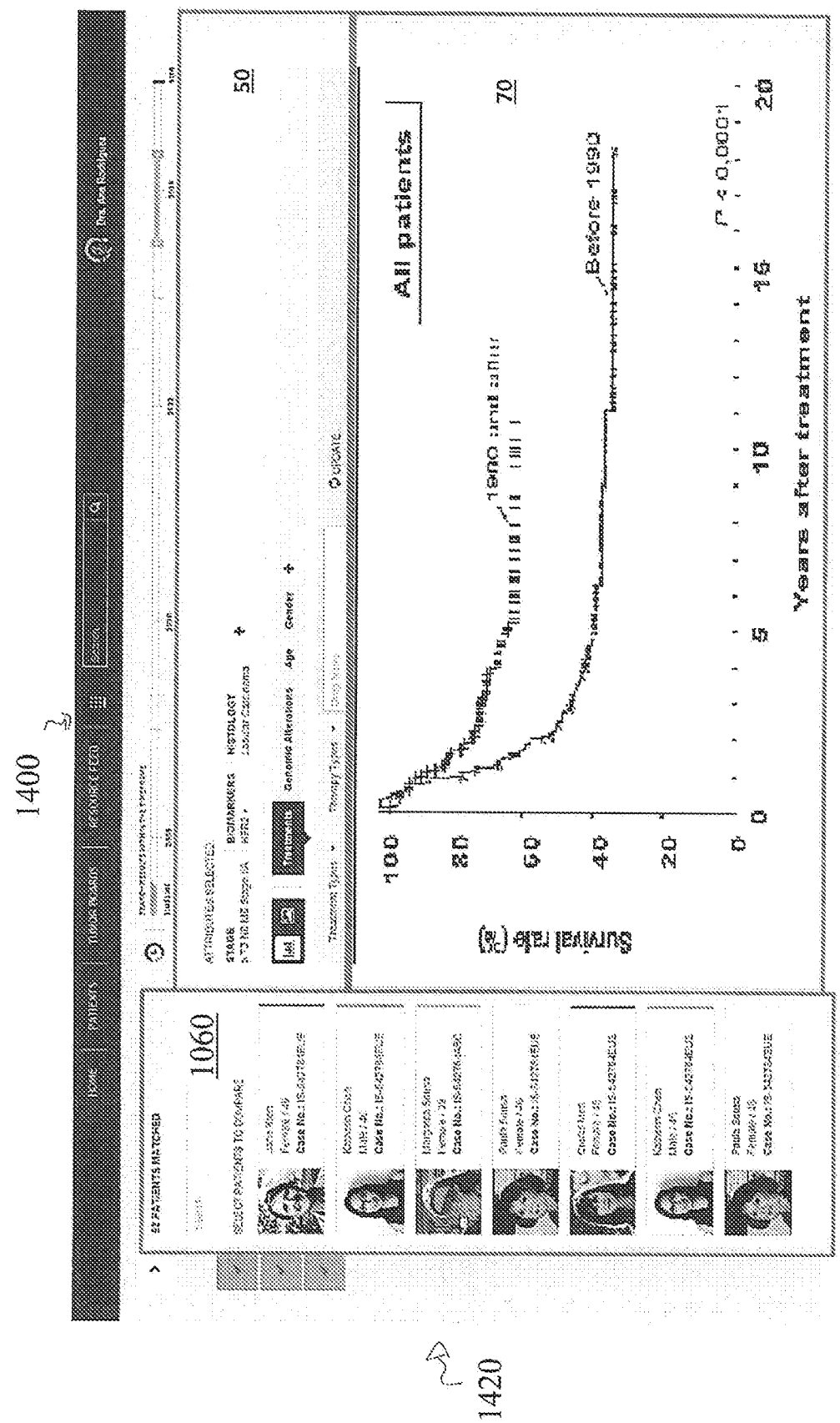
FIG. 33 is a diagram illustrating an exemplary biostatistical analytic tool workspace.

FIG. 33 illustrates the biostatistical analysis tool workspace 1400. This tool 1400 fully integrates with the curated oncology dataset. The workspace 1400 comprises an interactive interface 1420 allowing the user to select clinical attributes and values used to initiate the search for pools of similar patients. This provides a targeted focus for biostatistical analytics. In an additional embodiment, the biostatistical analytic tool workspace 1400 may also provide the researcher/clinician with the ability to interactively select variable specific to the Kaplan Meier Survival Analysis. These variables may include Survival Time and End Point Factor (remission/metastasis/death/etc.). The tool 1400 may also provide options on how to display this plotted data. Such options may include Linear trend for factor levels, Survival probably (%), 100—survival probability (%), include 95% CI in graph, Mark censored data in graph and number at risk table below graph. In addition, the researcher would have the ability to select a specific patient to compare to an aggregated population to visualize how the individual patient's values would compare. Once variables have been selected, the user would have the ability to render the plotted graph. The data and variables on the plotted graph may be edited to replot the analysis. The plotted analysis may be saved to a patient record or personal archive of interesting cases.

Also accessible from this interface would be the ability to share the plotted analysis with full interactive data accessible for confirmation/comment/further exploration of the analysis, determination of the patients matching the clinical attributes and values selected by the researcher/clinicians, and the graphical plotting of a generic biostatistical model or nomogram.

An example of how researcher/clinicians would interact with the disclosed application to determine Kaplan Meier Survival Analysis for a pool of cancer patients with an institution is as follows: researcher/clinician would login to the system and click on the "Biostatistical Analysis" tool which would be accessible via the generic application widget on the title bar of the application. The "Biostatistical Analysis" tool would launch in the workspace of the application. Researcher/clinician would select patient age, gender, type of cancer, specific biomarkers, treatments and any other clinical variable captured within system that would be of interest for research or patient treatment.

Researcher/clinician would then have the ability to select from any of the available "biostatistical analysis" models that have been integrated with the system software application. In this example, the Kaplan Meier Survival Analysis Tool would be selected. In the background, the system tool contains institution and outside patient data bases which contains the data for remission, death, times from initial treatment, etc. The researcher/clinician would then have the ability to interactively select variable specific to the Kaplan Meier Survival Analysis for example: Survival Time, End Point (remission/metastasis/death/etc.) Factor, as well as provide options on how to display this plotted data that include Linear trend for factor levels, Survival probably (%), 100—survival probability (%), include 95% CI in graph, Mark censored data in graph and number at risk table below graph. The researcher would have the ability to select a specific patient to compare to an aggregated population to visualize how the individual patient's values would compare. Once variables have been selected, the user would have the ability to render the plotted graph. The plotted graph would provide the ability to "edit" the data and variables to replot the analysis. Also available would be the ability to save the plotted analysis to a patient record or personal archive of interesting cases.

Synchronous and Asynchronous Collaboration in Treatment of Chronic and Complex Diseases In the last decade there's been a growing global trend to utilize personalized treatment and evidence-based medical practice to improve quality of care and increase patient safety. As a result, medical care delivery has moved from an isolated, individualized process towards a highly dynamic practice, which requires collaboration between different specialties. This teamwork approach is of especially great importance in complex, chronic diseases such as cancer (but also heart disease, diabetes, autoimmune disorders, etc.). The complexity of these chronic diseases and their general long course of treatment require the involvement of several disciplines, resources, and competence in order to provide optimal treatment to patients.

To take the case of cancer, specifically, recent studies have shown that to achieve optimal care for cancer patients, four factors must be realized: providers should collaborate with each other, care should be provided in the most optimal sequence, process of care should be integrated in a way to ensure connection between providers and at the same time retain their autonomy and unique role, and relationship between patient and care providers should be maintained.

Many hospitals and healthcare professionals have focused on increasing multi-disciplinary collaboration in treatment of cancer by convening Multidisciplinary Cancer Conferences (MCCs) also known as Tumor Boards. These conferences are regularly scheduled meetings where each individual patient case is reviewed by a team comprised of medical oncologists, radiation oncologist, surgeons/surgical oncologist, pathologist, radiologists, nurses, and social workers. The primary goal is to ensure that all appropriate tests, treatment options, and recommendations are considered for each patient. It is widely recognized that this interdisciplinary approach is attributed with enhanced clinical decision making and improved clinical outcomes, yet in the US only a small percentage of cancer patients are treated though cancer conferences. One of the reasons attributed to only a small percentage of patients being treated through medical conferences is the lack of a supporting workflow and adequate technology to allow physicians to timely prepare for, host, and facilitates medical conferences.

The current method and technology for facilitating Medical Conferences revolves around telepresence/telemedicine. This is where audio visual conference technology is utilized to give the essence of all being together in a room. This is not sufficient and many find this unsatisfying. These solutions also do not solve the time burden problem of having to gather everyone one at once which still puts a limitations on the number of patients that can be treated in a medical conference.

In addition, to date, at hospital systems in the US and around the world, it has been documented that it is difficult and challenging to identify discordance in Radiology and Pathology diagnosis. In many cases Radiology and Pathology diagnosis doesn't typically occur until the medical Oncologist is reviewing the diagnostic data to decide on best treatment or at times the discordances isn't realized until each department presents their findings at the multi-disciplinary tumor boards. It is typically at these physical meetings that the discordance is typically "teased out." Once a patient's discordance in Radiology and Pathology findings has been identified, new tests and procedures are typically ordered for the patient to enable both disciplines to resolve the discordance and come to an agreement on diagnosis.

Therefore, what is needed is a system and method that overcomes these significant problems found in the conventional system for Multidisciplinary conferences and provides an improved method for conducting asynchronous virtual medical conference boards, resolving diagnostic discordances, and facilitating curbside consultations (second opinions).

Described herein are systems and methods that establish a software platform that leverages the latest IT solutions and infrastructure to support all manners of information exchange and communication among clinical team members. The systems and methods described provides a software platform and infrastructure that facilitates asynchronous medical conference boards, aids in resolving diagnostic discordances, and facilitates formal curbside consultations (second opinions). This will allow for more patients to be able to benefit from an interdisciplinary approach to their treatment by eliminating the need for all members of the care team to meet at the same time and in the same location.

In one embodiment the system may comprise an architecture that leverages comprehensive integration of all relevant IT systems within a hospital system to enable visualization, correlation, and collaboration between medical care teams within a hospital system. The system may provide a method for a physician to initiate or request the convening of an asynchronous virtual medical board. That is to say collaborators through the system will be able to review, discuss, and make recommendations for a patient without all being in the same place or at the same time. The system may also provide a method for a physician to select a patient and purpose for the virtual tumor board. All the patients relevant medical data may be fully integrated into the platform and may be reviewed by the organizing physician. The system may provide an auto suggestion of physicians and other medical professional to be included in the virtual tumor board. The system can also allow for the organizing physician to search and select from list of medical care professionals associated with the hospital.

The system may comprise a central permission management system that is tightly coupled with the active directory or Lightweight Directory Access Protocol (LDAP)-based system utilized by the hospital IT system. This permission management system may be a learning system that is actively algorithmically constructing a neural social graph of all users of the system. This algorithm may consider, among other things, the patient population overlap, specialty, location, and system use characteristic of each user to construct the social graph.

Once the organizing physician as selected patient, purpose, and list of collaborators to the virtual tumor board, the system can send notifications to the invited collaborators. These invitations can be sent to the user's preferred communication choice (as stored in permission management system). The notifications can all have a link and method to bring the physician into the System to review and collaborate in the virtual tumor board. The invitations can also contain secure login credentials that ensure the identity of the user.

The system may also support role-based access and permission on a patient level of security. Only those medical professional invited to participate or are already part of the patient's medical team will be able to access and review a patient's case.

The system can provide collaborators a method to exchange input on their various perspectives of the patient case. One embodiment of this method for exchange is a chat application within the system that shows real time discussions and comments by collaborators. Each chat will be linked to contextual patient attribute/data item. The chat can be documented in the patient's medical record within the system.

The system can provide a method for consolidating the recommendations of all collaborators into a unified recommendation for the patient and a method for physicians to check and assure concordance between all diagnostic specialties.

The system can be fully integrated to all the hospital IT systems and provide contextual patient information too all users of the system.

The system can evaluate patient data and search for pre-determined "flags." These flags will trigger to a user of the system a possible need to check concordance. The user will be able to select whether the system should check concordance or not. If the user selected to have concordance checked then the system may initiate a Concordance Check workflow. This workflow will prompt the user to review Radiology, Pathology, as well as any other pertinent diagnostic data for the patient and confirm or refute if there is concordance between the results. If there is discordance in the results, the system will aggregate the relevant images and .pdf reports in a single Radiology/Pathology consolidated interface. From this interface, the managing specialists will have the ability to document their discussion, select the follow-up clinical tests to perform and finally document the resolution of the discordance date stamping and synchronizing with other source systems. The system can also record the results of the concordance check. This workflow can also be triggered and executed through the system at a Medical Conference Board.

The system can keep track of all concordance checks and results and also keep track of whether concordance checks are initiated proactively by a user or are triggered by an observed discordance during a medical conference board. The system can log all the relevant features of the patient data that are found in discordance in order to learn what kind of cases are likely to be discordance. This learning algorithm will allow for improved "flags" and over time reduced rates of occurrence of discordance.

The system can contain in its database architecture a Boolean table that captures the results of the concordance workflow. The concordance feature of the system will serve as a method to determine and quantify the prevalence of discordance and drive quality improvements. The concordance feature data will be able to be reviewed by administrators and the like. The system will support the exporting of reports containing concordance data. The system overtime through machine learning algorithms could be able to automatically flag and highlight discordant data and initiate a workflow to resolve the discordance. These machine algorithms may have the following inputs, for example: all patient data loaded from EMR, PACs, AP-LIS, CP-LIS, etc., including PDFs, Medical Notes, Documents, Image Meta Data, etc.; major oncology and general medical ontologies overlayed into the system (e.g., Snored, NCI Thesaurus, ICD-10, Radlex, etc.).

Through NLP technology the following attributes can be extracted from patient data, for example: demographic information, functional status, family history; cancer staging and characteristics or histology; biomarkers; genetic variations; diagnostic testing and results, additional search queries mapped to oncology ontologies, etc. All unstructured data can be extracted and converted to structured data. All data elements can then be indexed in an optimized manner. All indexed fields can then be passed to the system for storing. The system can then take this data and run comparison for each diagnostic specialty based on date of report to determine if there is concordance.

In another embodiment, the system may comprise an architecture that leverages comprehensive integration of all relevant IT systems within a hospital system to enable visualization, correlation, and collaboration between medical care teams between different hospitals. The system may provide a method for a physician to initiate or request a formal curbside consultation (second opinion). For example, collaborators through the system may be able to review, discuss, and make recommendations for a patient without all being in the same hospital system. The system may comprise a network of hospitals linked via a central database (data hub) that resides independent of any hospital.

The data hub may contain a central permission management system resides. This permission system can keep track and monitor access to patient records in the hub. The data hub will aggregate and contain de-identified versions of the data found in each individual hospital system. The system will have a novel method of removing or obstructing all PHI data from reports, images, and other data related to a patient's case.

As an example of a possible workflow, a physician in hospital A may require a consultation or second opinion about a patient. The system may allow the requesting physician to send a request to another physician in hospital B who has an expertise or knowledge set required. The system can send a notification to the consulting physician prompting the physician to log into the system to review the patient's case. The invitation may contain secure login credentials that ensure the identity of the user. Once logged into the system, the consulting physician is able to review a de-identified version of the patient's case. In some embodiments, patient's health information (PHI) may not be visible to the consulting physician; however the physician could still review all the necessary patient medical data in order to provide an opinion or recommendation.

The system may also facilitate the communication between the requesting and consulting physician. This can be in a chat-like application that records and stores communications to associated data points. The system may facilitate the communication of the recommendations of the consulting physician back to the requesting physician. The system may also provide a method for a patient to initiate or request a formal curbside consultation (second opinion). That is, the patient can send through the system their relevant medical data to be reviewed to a physician in a different hospital system.

Neuro-Oncology Visualization and Workflow Tool

The present application also generally relates to an improved method, computer program product and system for visualizing and providing workflow for neuro-oncology cancer patients' clinical history, tumor details, current clinical laboratory results and treatment decisions, as specified in the independent claims.

Figure 34:
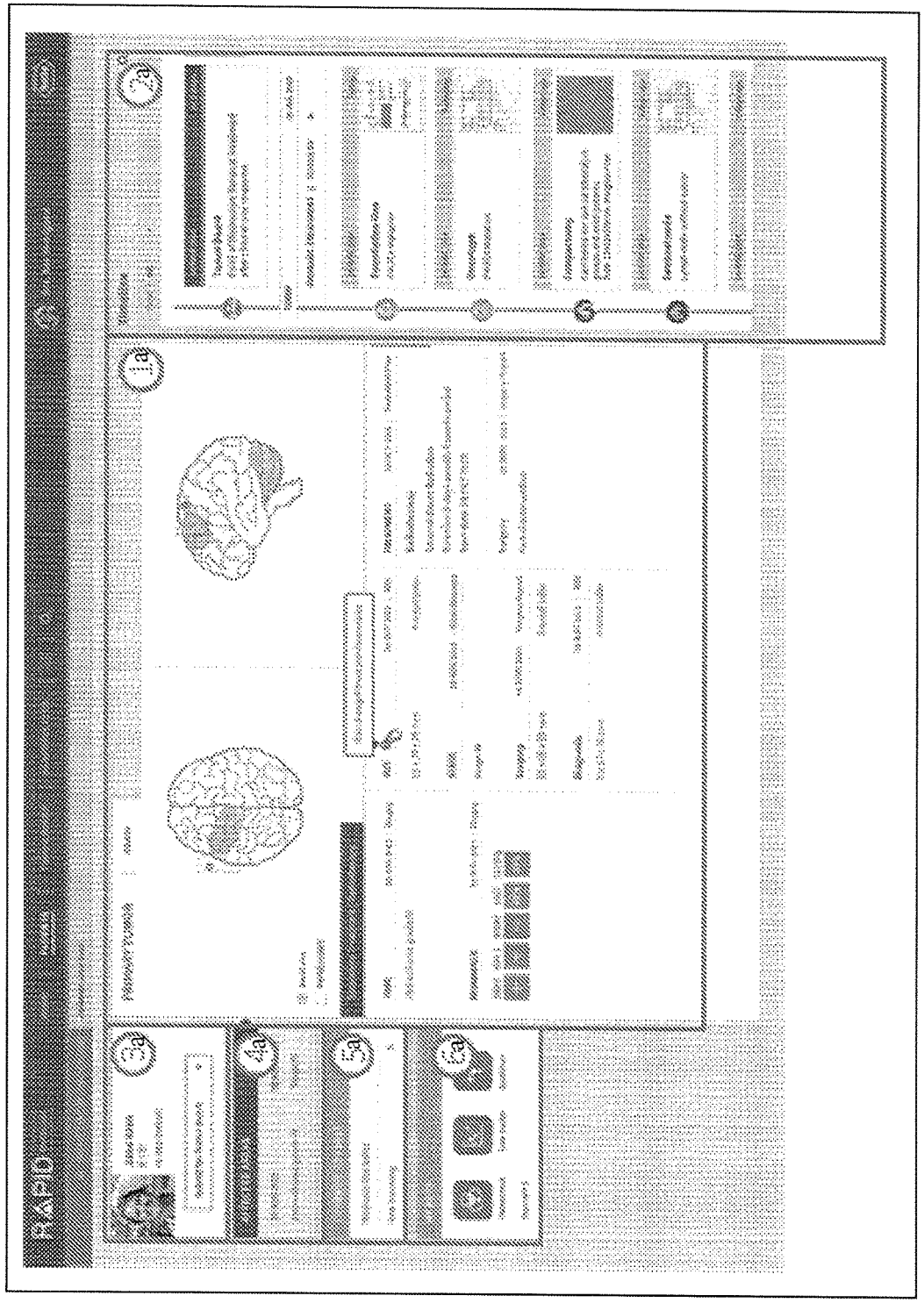
FIG. 34 shows an exemplary screenshot of the items presented on the interactive display after the computer system aggregates a patient's neuro-oncological clinical data.

Referring to FIG. 34, an interactive display is shown. In some embodiments, the interactive display is populated after the computer system aggregates a patient's neuro-oncological clinical data. In FIG. 34, item 1a marks an area on the interactive display wherein simplified pieces of neuro-oncological tumor information are shown. The pieces of neuro-oncological tumor information can include, but are not limited to, tumor type information from biopsy reports and EMR fields, biomarkers captured from the biopsy report and EMR fields, tumor size captured from recent MRI reports, EMR fields and RIS fields, staging Information from other oncological encounters, diagnostic Information captured from radiology reports and RIS or PACS fields, surgical procedures captured from surgical reports in EMR, and treatment plans captured from oncologists' notes and previous tumor board recommendations. Item 2a marks an area on the interactive display with a visual timeline that provides intelligent filtering. Item 3a marks an area on the interactive display that allows access to a patient's history, medical problems, and demographical information. Item 4a marks an area on the interactive display with an "Affected Areas" tab which provides quick access to the area described in item 1a. Item 5a marks an area on the interactive display comprising "Curbside Consult", which is an asynchronous and synchronous collaboration tool that enables clinicians to discuss a patient's clinical information. Item 6a marks an area on the interactive display platform for third-party online reference tools, which provide access to patient-relevant clinical information via the patient's neuro-oncological clinical data.

According to one embodiment, a system that provides neuro-oncology specific information of a patient is provided. The system may comprise a server and a client device capable of communicating with the server. In some embodiments, the server comprises a database and a plurality of aggregated and comprehensive electronic clinical data of the patient. The electronic clinical data may comprise at least neuro-oncological tumor data, in addition to other patient-specific data. In other embodiments, the client device capable of communicating with the server comprises a display interface, a processor operatively coupled to the display interface; and a memory operatively coupled to the processor that stores computer-readable instructions which, when executed by the processor, causes the processor to perform operations. The operations performed by the processor may comprise retrieving neuro-oncological tumor data from the server and displaying an interactive workspace on the display interface which provides patient specific information pertaining to the neuro-oncological tumor data.

According to another embodiment, a method for providing neuro-oncology specific information of a patient is provided. The method may be stored on a computer-readable medium and may comprise logical instructions that are executed by a processor to perform operations comprising retrieving aggregated and comprehensive electronic clinical data of a patient and at least neuro-oncological tumor data for the patient's cancer from a medical database, and displaying an interactive workspace on a display interface that provides patient specific information pertaining to the neuro-oncological tumor data.

In some embodiments, the electronic clinical data comprises picture archiving and communication system (PACS) data, radiology information system (RIS) data, digital pathology, laboratory information system (LIS) data, Next-Gen Sequencing (NGS) data, and electronic medical records (EMR) comprising previous medical treatments and test results. In some embodiments, the interactive workspace can display summary information about the patient and neuro-oncological tumor data, which can be presented as graphically simplified points of information. The summary information may be obtained from tumor type information from biopsy reports and EMR, biomarkers captured from the biopsy report and EMR, tumor size captured from recent MRI reports, EMR or RIS, stage information from other oncological data, diagnostic information captured from radiology reports, RIS or PACS, surgical procedures captured from surgical reports in EMR, and treatment plans captured from oncologists' notes and recommendations.

In one embodiment, the interactive workspace displays at least one image of a tumor and its location. In another embodiment, the interactive workspace enables a user to prepare, present, and archive the neuro-oncology tumor data related to the patient's treatment plans. The interactive workspace may further automatically chart and visualize neuro-oncology-specific clinical values to provide a clinical overview of the patient's neuro-oncology specific information. In some embodiments, the neuro-oncology-specific clinical values are tumor size and biomarkers, wherein the biomarkers are Ki67 (IHQ), MGMT methylation, 1p/19q, IDH-1, and BRAF.

In yet another embodiment, the interactive workspace enables a user to select and display patient data chronologically from the electronic clinical data. The interactive workspace may also enable a user to display information pertaining to previous surgical treatments and previous therapy regimes. In yet a further embodiment, the interactive workspace enables filtering by categories.

In some embodiments, the interactive workspace further comprises an image viewing application that provides basic image manipulation and direct, single sign-on (SSO) access to 3rd party databases for side-by-side comparison of images from different specialties. In other embodiments, the interactive workspace enables a user to generate reports that provide system aggregated patient information, clinical trial query results specific to the patient, and multi-disciplinary recommendations. In still other embodiments, the interactive workspace further comprises clinical tools from $3^{rd}$ party vendors to provide patient specific references.

In one embodiment, the interactive workspace enables a user to collaborate with other users in real-time to share findings and consult on potential clinical courses. In another embodiment, the interactive workspace is synchronous and asynchronous to facilitate user collaboration and to document neuro-oncology discussions as independent reference points. In some embodiments, the collaboration tool can include a chat interface, a consultation interface, and a virtual meeting interface.

In a non-limiting example, the chat interface enables two or more doctors or other medical personnel to have either synchronous or asynchronous communication among each other. Synchronous communications occur when the doctors or medical personnel are using the chat interface at the same time, i.e., in real-time. Asynchronous communications occur when the doctors or medical personnel are using the chat interface at different times, e.g., offline. In addition to exchanging messages, the chat interface enables doctors or other medical personnel to include contextual patient attributes such as images and reports with a message to be exchanged.

In a non-limiting example, the chat interface can include messaging functionality to permit the medical personnel to exchange messages with each other. In addition, the chat interface can also determine user presence based on the user's login status and can provide other users with the ability to detect when a particular user is accessing the informatics platform and available for collaboration. In addition, the chat interface can be used to share clinical context and information when exchanging messages regarding a patient. The chat interface also provides the ability to save the collaboration sessions and to include the saved collaboration session in a patient's medical record.

In a non-limiting example, the consultation interface enables doctors to request impromptu consultation sessions from one doctor to another doctor in real-time (synchronous) and offline (asynchronous) modes. In one embodiment, the collaboration tool can document the chats and consultations regarding a patient and can include the documented chats and consultations as part of the patient's medical record. In another embodiment, the collaboration tool can determine a doctor's active availability and the best form of communication with the doctor.

In a non-limiting example, the virtual meeting interface may be used to initiate and document an asynchronous collaboration stream for remote or virtual tumor board workflow. In a virtual tumor board, medical personnel can "pin" information, provide contextual overview for their specific discipline and provide a "draft" recommendation form and treatment plan for the board to review. Once all the medical personnel have indicated "readiness" and a "draft" recommendation form and treatment plan is prepared, the virtual meeting interface provides an asynchronous collaboration window to capture any agreement/disagreement among board members and/or notes for each participating doctor. If all board members agree on the "draft" recommendation form and treatment plan, the virtual meeting interface changes the status of the recommendation form and treatment plan to "final" and documents the participating medical personnel and the dialog that determines full consensus. If there is not 100% agreement among board members and the responsible doctor for the patient doesn't want to continue pursuing the "draft" treatment plan with the virtual tumor board, the virtual meeting interface can add the patient to the next physical tumor board. The virtual meeting interface can enable users to review and prepare, offline or asynchronously, for a virtual tumor board and provide respective input for an interactive treatment form or the recommendation form that can occur before the physical tumor board event takes place.

Multi-Variable Neuro-Oncological Interactive Chronological Visualization Tool

The present application also generally relates to systems and methods of collecting neuro-oncological data from a plurality of hospital information systems, correlating the data, plotting the data on a time domain, and presenting the data on an interactive display. Users can adjust the view parameters on this interactive display to customize the information and plots on the screen. These systems and methods allow clinicians can quickly visualize and understand a patient's condition and devise a countermeasure in a timely manner.

Figure 35:
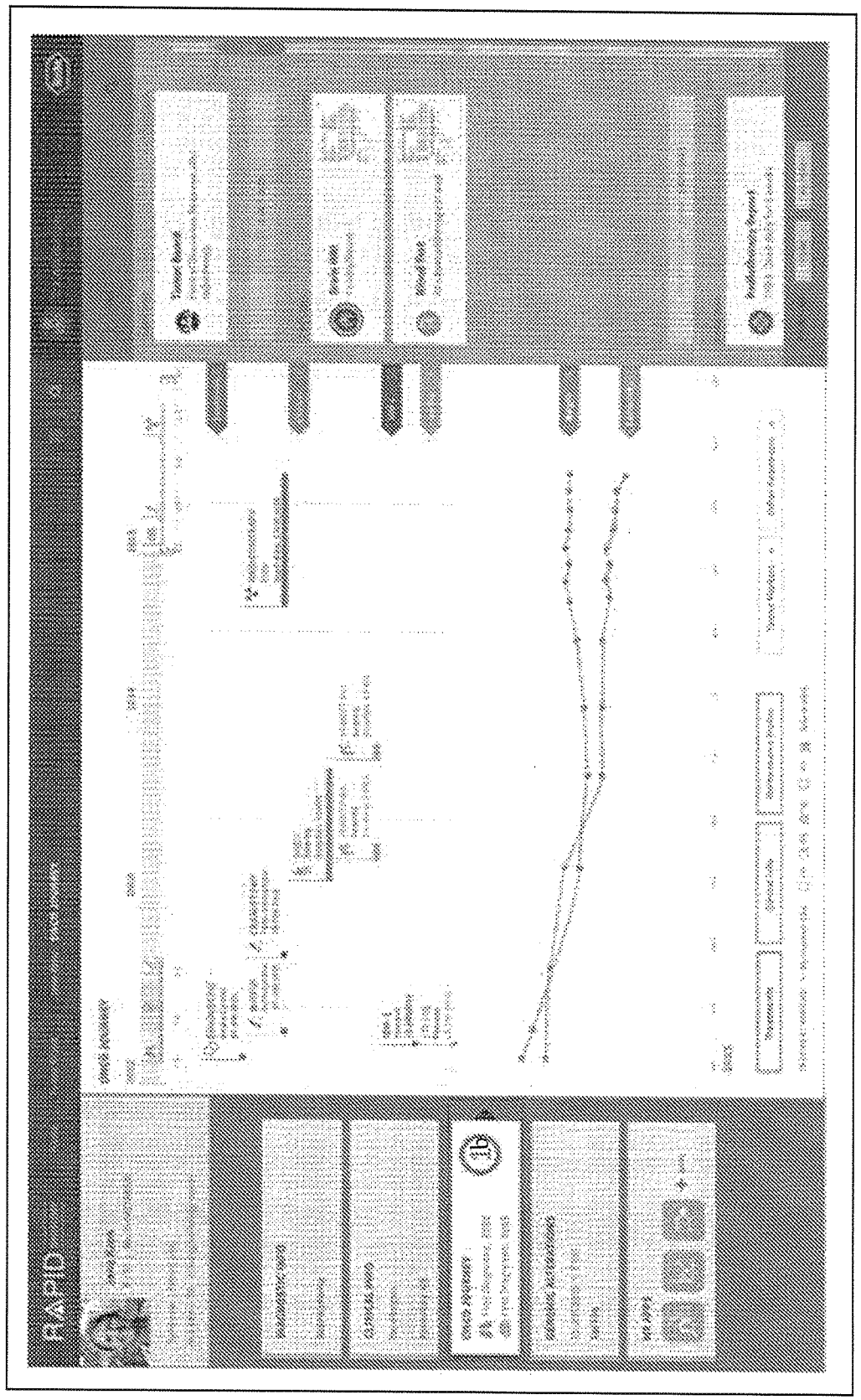
FIG. 35 shows the Multi-Variable Neuro-Oncological Interactive Chronological Visualization Tool main screen.

Referring to FIG. 35, the Multi-Variable Neuro-Oncological Interactive Chronological Visualization Tool main screen is shown. In some embodiments, upon pressing the "Onco Journey Icon" marked out by item 1b, the Multi-Variable Neuro-Oncological Interactive Chronological Visualization Tool is initialized and the patient's aggregated clinical data is plotted in the time domain.

Figure 36:
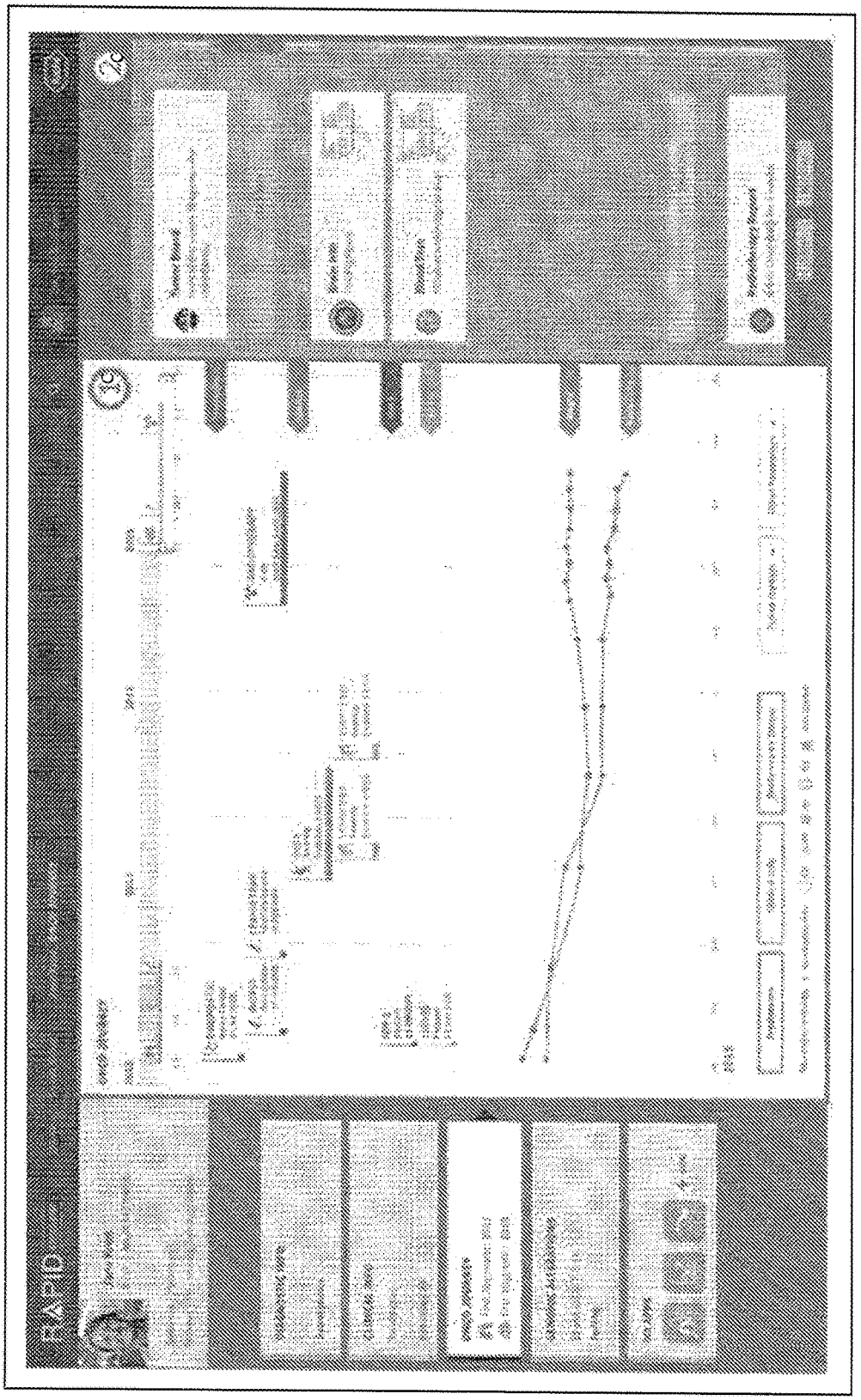
FIG. 36 shows the Multi-Variable Neuro-Oncological Interactive Chronological Visualization Tool visualizing multiple patient attributes.

Referring to FIG. 36, examples of what the Multi-Variable Neuro-Oncological Interactive Chronological Visualization Tool main screen may contain are shown. In some embodiments, the Multi-Variable Neuro-Oncological Interactive Chronological Visualization Tool visualizes multiple patient attributes including but not limited to genetic biomarker values, lab results and images, treatments, and procedures in a quantitative display (chart) that includes access to qualitative studies. Item 1b marks an area wherein relevant Neuro-Oncological data is charted automatically in the time domain and displayed simultaneously to visualize new data correlations and relationships. Item 2b marks an area wherein the patient's timeline comprising every clinical test and exam note can be accessed.

Figure 37:
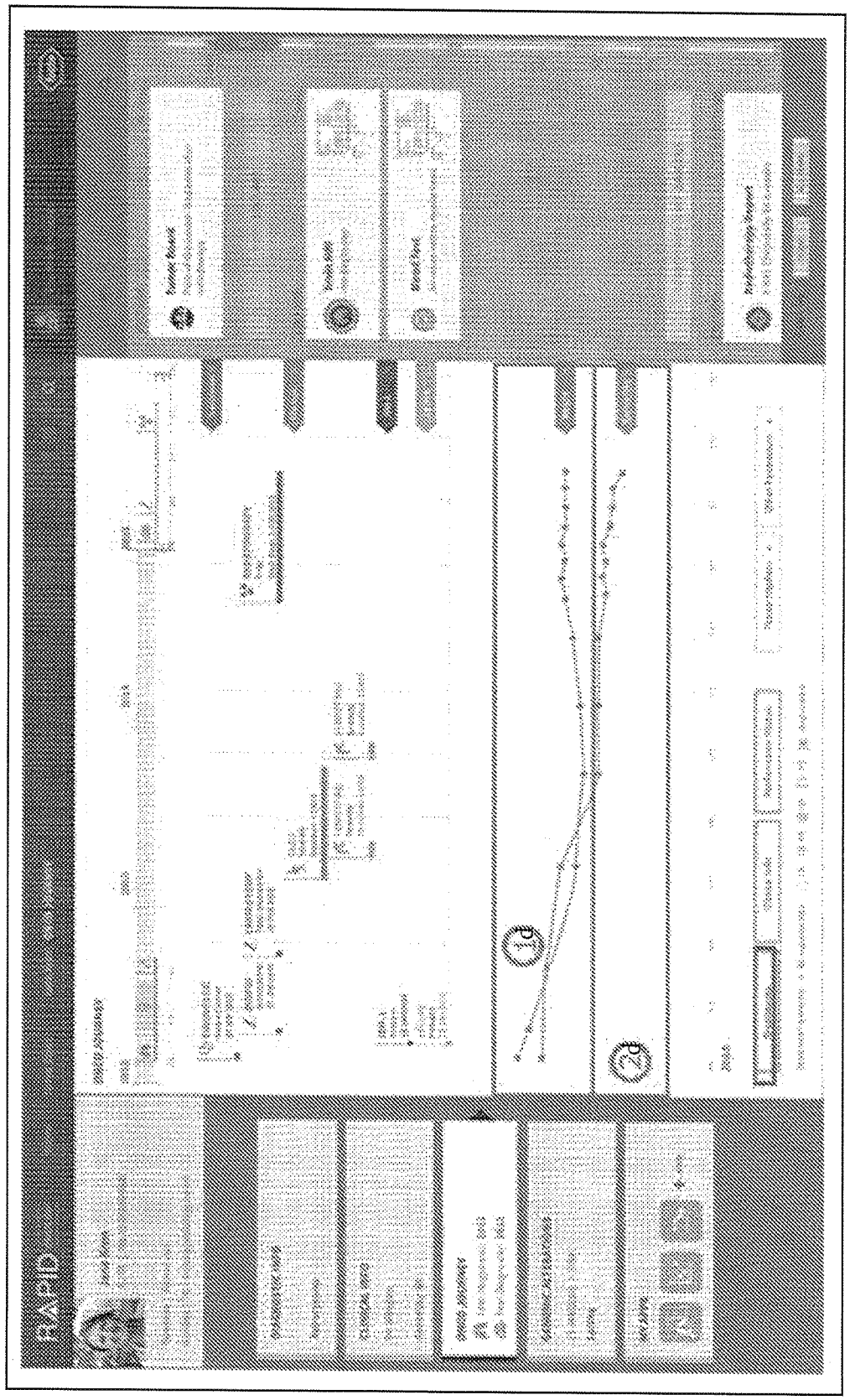
FIG. 37 shows an example of a patient's weight attribute (1) and Karnofsky value attribute (2) trending over time as plotted by the Multi-Variable Neuro-Oncological Interactive Chronological Visualization Tool.

Referring to FIG. 37, examples of plotted attributes are shown. Item 1c marks an area wherein the patient's weight trending over time is plotted. Item 2c marks an area wherein the patient's Karnofsky value trending over time is plotted when the "Treatment" button is pressed. In some embodiments, this allows the clinician to interactively visualize the patient's weight and Karnofsky values over time in response to various treatments and episodes according to the patient's treatment plans.

Figure 38:
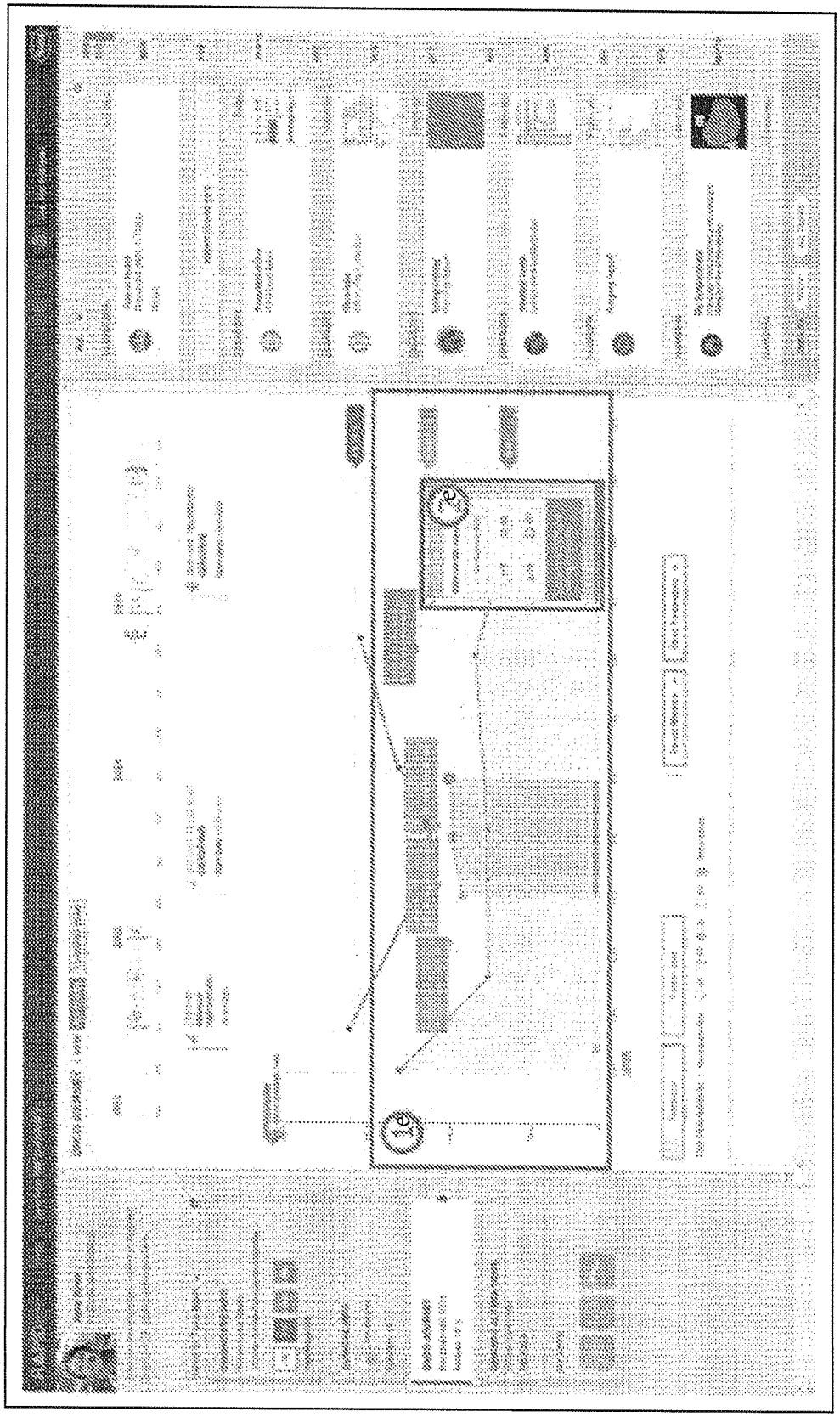
FIG. 38 shows the Multi-Variable Neuro-Oncological Interactive Chronological Visualization Tool's "Mouse-Over" function (1) and manual input function (2).

Referring to FIG. 38, the Multi-Variable Neuro-Oncological Interactive Chronological Visualization Tool's "Mouse-Over" function and manual input function are shown. Item 1d marks out an area wherein an example of the "Mouse-Over" function is shown. In some embodiments, to minimize screen clutter and allow clinicians to see easily view the generated plots, data points are not displayed by default. In some embodiments, when the user hovers over plotted points, the Neuro-Oncological Interactive Chronological Visualization Tool displays meaningful information on the plotted data, including but not limited to data value, date of data capture, and corresponding "Y-axis" values. Item 2d marks out an area wherein an example of the manual input function is shown. In some embodiments, as the patient's responses to certain treatments are not always automatically documented, the Multi-Variable Neuro-Oncological Interactive Chronological Visualization Tool allows clinicians to manually enter treatment response data.

Figure 39:
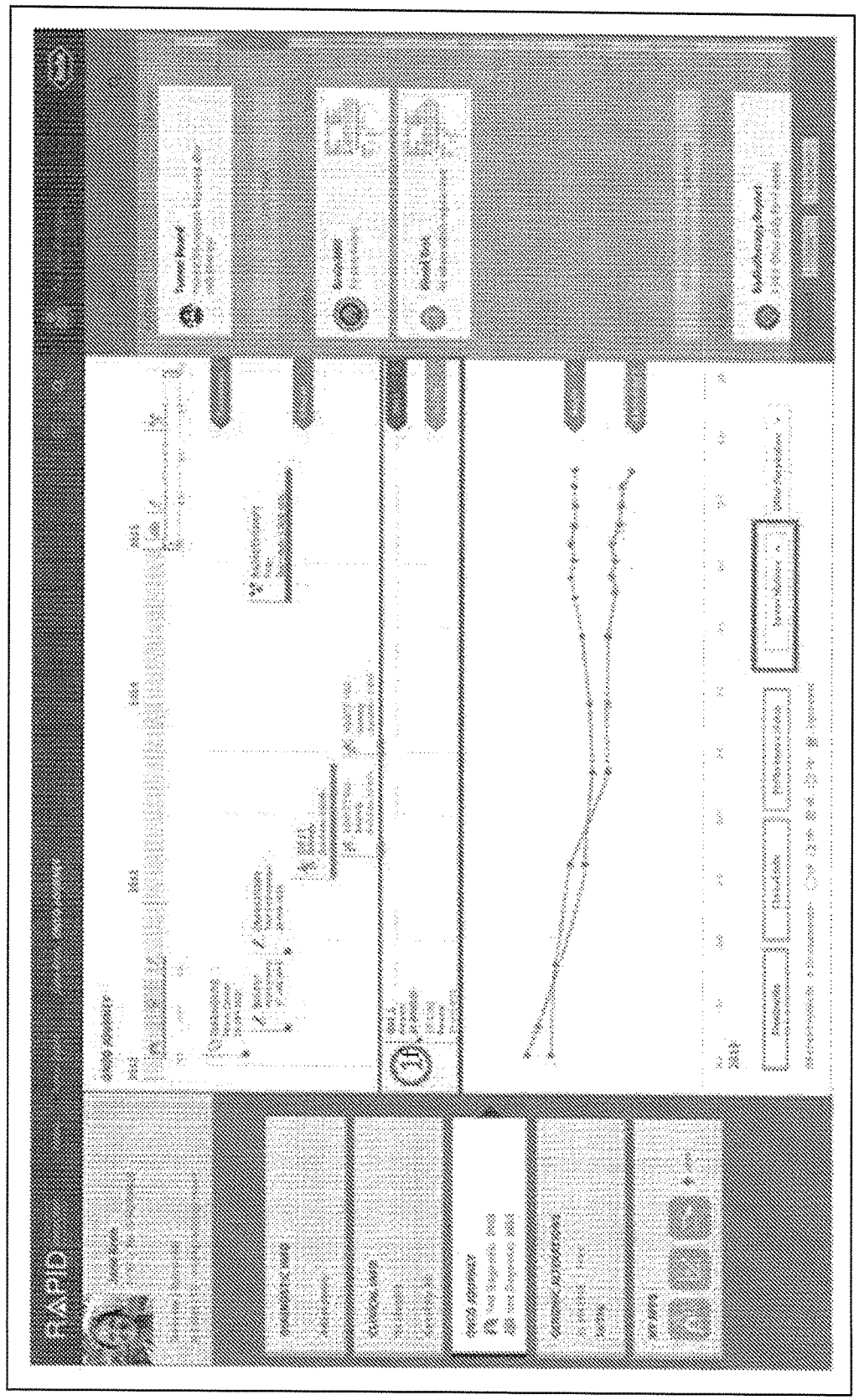
FIG. 39 shows the Multi-Variable Neuro-Oncological Interactive Chronological Visualization Tool's "Tumor Markers" button.

Referring to FIG. 39, the Multi-Variable Neuro-Oncological Interactive Chronological Visualization Tool's biomarker filtering function is shown. In some embodiments, clicking on the "Tumor Markers" button displays the filter that allows user to select which biomarkers to plot over time. Item 1e marks out the area wherein the biomarkers are filtered. Users are allowed to select biomarkers within the same context simultaneously. In some embodiments, each biomarker is color-coded and labeled to allow easy distinction. In some embodiments, new Biomarkers are automatically added if newly available biomarkers are identified for the patient.

Visualization of Interactive Oncology Treatment

To date, genetic sequencing reports are excessive and contain a wide array of information that relates to potential treatments, clinical trials and information on gene variants. For an expert in the field, this information is relevant and informative. To the majority of clinicians, this information is overwhelming and too detailed for these clinicians that need to interpret the reports and prescribe treatments for their patients. Additionally, sequencing reports are solely based on genomic only databases that provide analysis from one perspective. Genetic sequencing reports are, by standard, 16-20 page .pdf reports that contain all relevant information. The initial page typically contains the summarizations, but it is difficult to navigate the pdf report to find and understand the content within the document. Hence, there exists a need for a quick and convenient approach to simplify usage and the vast amount of data typically associated with potential treatment options.

According to one embodiment, a therapeutic mapping system for providing genomic alteration information is provided. The system may comprise a server and a client device capable of communicating with the server. The server may comprise a genomic database and a plurality of aggregated and comprehensive electronic clinical data of a patient. The electronic medical data may include, but are not limited to, picture archiving and communication system (PACS) data, radiology information system (RIS) data, digital pathology, laboratory information system (LIS) data, and electronic medical records (EMR) comprising previous medical treatments and test results. The client device may comprise a display interface, a processor operatively coupled to the display interface, and a memory operatively coupled to the processor.

In some embodiments, the memory stores computer-readable instructions that, when executed by the processor, cause the processor to perform operations comprising retrieving the electronic medical data from the server, including at least one gene and genomic alteration for the patient's cancer; retrieving patient specific and genomic alteration specific information from the genomic database; and displaying an interactive workspace on the display interface that provides patient specific information about the genomic alteration relevant to the patient's cancer. The workspace is configured to display top-level summary information about the patient and genomic alteration, which is easily digestible by the clinician. The workspace incorporates hyperlinks to more detailed information such literature reports and established medical guidelines for the gene, genome interpretations for the genomic alteration, and matching therapies for the genomic alteration on the display interface, allowing the clinician to easily navigate to the most relevant information quickly.

According to one embodiment, the matching therapies may be displayed below the hyperlinks on the display interface. The electronic medical data may be displayed in chronological order as a timeline that is positioned vertically and adjacent to the hyperlinks and matching therapies.

In some embodiments, the matching therapies may comprise information for Food and Drug Administration (FDA) approved drugs, clinical trials, and off-label drugs. The workspace can be configured to display a level of evidence, a treatment regimen, drug resistance, drug cost, and a percent of insurance coverage for the FDA approved drug. The workspace can also be configured to display a plurality of tags, wherein one of the tags is selected and assigned to the FDA approved drug to indicate the patient's response to the drug. In other embodiments, the workspace is configured to display filters for the clinical trials, and to apply selected filters to narrow a number of clinical trials applicable to the patient's cancer. The filters may include, but are not limited to, genetic mutation, patient condition, trial location, trial drug, drug class, drug resistance, institution performing the trial, drug phase, trial type, and trial status. In further embodiments, the workspace is configured to display a drug indication, a level of evidence, a prescription label, a treatment regimen, drug cost, and a percent of insurance coverage for the off-label drug.

According to another embodiment, a therapeutic mapping method for providing genomic alteration information is provided. The method may be stored on a computer-readable medium and may comprise logical instructions that are executed by a processor to perform operations. The operations can comprise retrieving aggregated and comprehensive electronic clinical data of a patient and at least one gene and genomic alteration for the patient's cancer from a medical database, retrieving patient specific and genomic alteration specific information from a genomic database, and displaying an interactive workspace on a display interface that provides patient specific information about the genomic alteration relevant to the patient's cancer. Non-limiting examples of the electronic medical data may include picture archiving and communication system (PACS) data, radiology information system (RIS) data, digital pathology, laboratory information system (LIS) data, and electronic medical records (EMR) comprising previous medical treatments and test results.

In some embodiments, the workspace can display summary information about the patient and genomic alteration. The workspace can incorporate hyperlinks to literature reports and established medical guidelines for the gene, genome interpretations for the genomic alteration, and matching therapies for the genomic alteration on the display interface. In some embodiments, the matching therapies may contain information for Food and Drug Administration (FDA) approved drugs, clinical trials, and off-label drugs. In other embodiments, the electronic medical data may be displayed on the workspace in chronological order.

In some embodiments, the method may further comprise displaying a level of evidence, a treatment regimen, drug resistance, drug cost, and a percent of insurance coverage for the FDA approved drug. In other embodiments, the method may further comprise displaying a plurality of tags. One of the tags may be selected and assigned to the FDA approved drug to indicate the patient's response to the drug. In further embodiments, the method may also comprise displaying a drug indication, a level of evidence, a prescription label, a treatment regimen, drug cost, and a percent of insurance coverage for the off-label drug. In still other embodiments, the method may further comprise displaying filters for the clinical trials. The filters may be selected and applied to narrow the number of clinical trials pertaining to the patient's cancer. The filters may include, but are not limited to, genetic mutation, patient condition, trial location, trial drug, drug class, drug resistance, institution performing the trial, drug phase, trial type, and trial status.

In some embodiments, volumes of genomic alterations and associated information (e.g., journal articles, clinical trial information, databases, etc.) are analyzed and synthesized into information items viewable on a therapeutic mapping system. The system can be configured to focus practitioners on discrete and relevant portions of any genomic alteration information. Curated information is provided on the system to enable practitioners to make informed decisions regarding the implications of the presence of specific genomic alterations. Curated information includes interpretations of available information (e.g., existing therapies, clinical trials, journals, and publications) for genomic alterations found in a patient's tumor.

According to one embodiment, the genomic interpretations present contextual information regarding the gene implicated in a patient's cancer. In some embodiments, the curated information can also include interpretive statements that summarize and/or apply current analysis of any available information associated with genomic alterations. The curated information can include references to an information source from which the curated information is derived. In some embodiments, the system can provide direct access to a source of the curated information. For example, the system can provide for direct navigation to a relevant clinical trial while in context of reviewing information on a specific genomic alteration. The curated information can also include direct links to the source information hosted at external information sites. The information sources can also be reviewed by the user to further describe or validate the curated information being provided.

An easy and navigable interface allows a user to locate the relevant treatment information in a timely manner. In some embodiments, the interface can be organized and navigated based on specific alterations found in a patient's cancer. In such settings, the user can navigate to information matching the patient's cancer (e.g., tumor type, gene, and alteration) to find directly relevant treatment information. Additionally, the user can navigate to related information matching one or more of a patient's tumor type, gene, and alteration to inform the user of potential off-label treatment options.

Publically available data (e.g., therapy data, clinical trial data, and journal publications) can be interpreted to provide the curated information. The curated information can be accessed on the system based on its relationship to one or more of the tumor, gene, and alteration for a patient. The publically available information can also be processed on the system to provide navigable data structures informing the user of available actionable information associated with a patient's cancer.

In one embodiment, an interactive workspace is provided to allow for easy navigation to genomic alteration results and associated information to reduce the amount of time necessary to determine an appropriate treatment for a user. The user may be presented with a collection of information to provide an informed treatment recommendation. For instance, with a view of identified genomic alterations, the user can to navigate to other information related to each genomic alteration, such as, therapy information, information on a clinical trial related to the genomic alteration, and any references that might be available to inform or support the application of such therapies. By having such information within an easily navigable interface, users may more quickly identify appropriate treatments.

In one embodiment, the information sources relevant to any one or more of a patient's tumor type, gene implicated by the tumor, and genomic alteration type is collected. In one embodiment, interpretations are generated or collected for the genomic alteration. The interpretations may include information of the role of the gene in health and disease, e.g., in cancer, e.g., the patient's type of cancer, or another cancer, including curated information e.g., one or more identifiers of sources of primary information, e.g., published journal articles, on the prevalence of the alteration in particular cancers or populations, therapies for the subject genomic alteration, or related genomic alterations, clinical studies of specific therapies for cancers within the current patient's tumor type or otherwise, and genomic alteration, e.g., a type of alteration, e.g., base substitution, insertion, deletion, amplification, homozygous deletion, rearrangement.

Figures 40, 41:
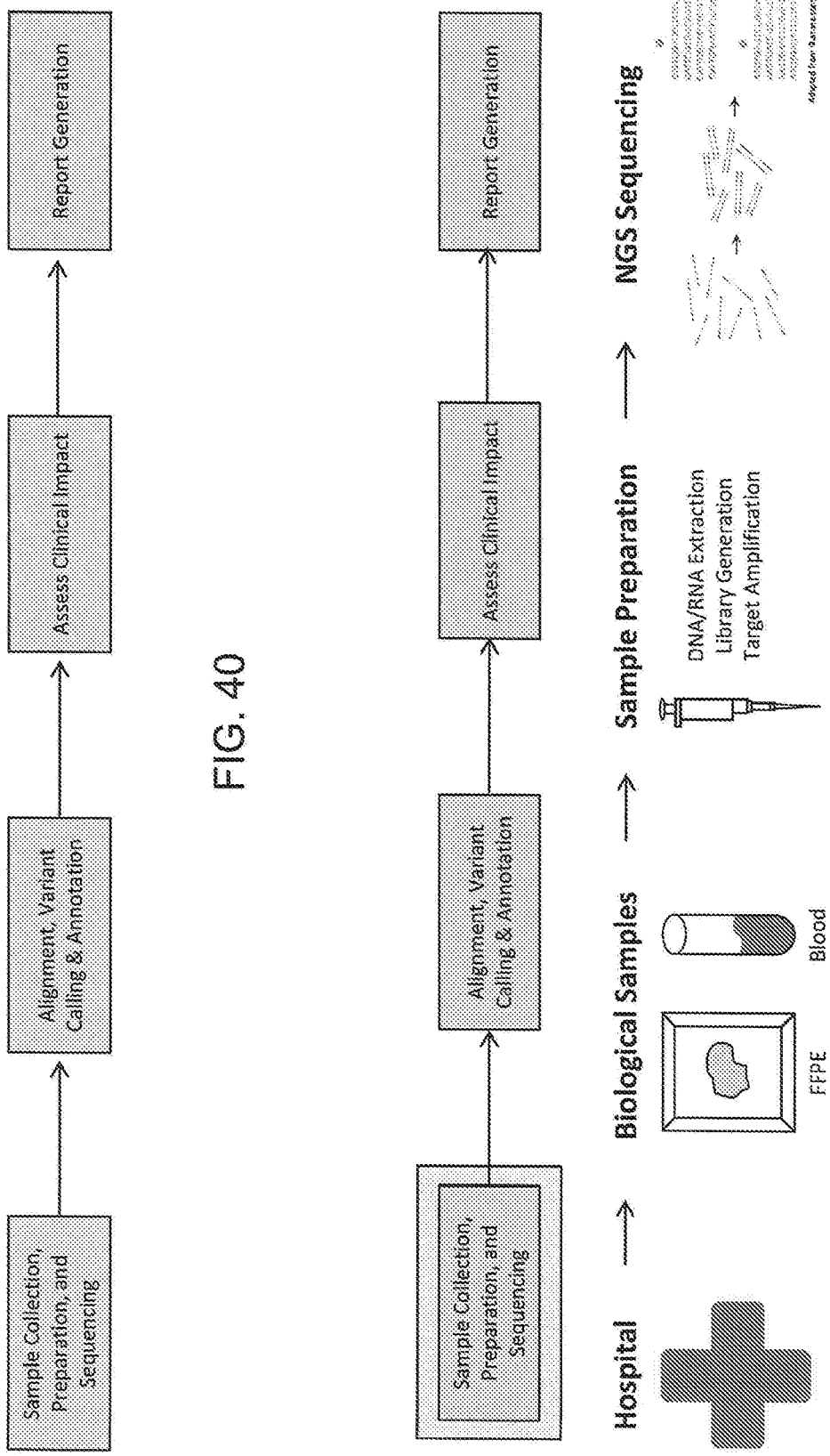
FIG. 40 shows an exemplary clinical sequencing schematic.
FIG. 41 shows an exemplary schematic of sample collection, preparation, and sequencing for clinical sequencing.

Referring to FIGS. 40 and 39, in the case of solid tumors, samples are extracted from patients and usually frozen or stored in formalin-fixed, paraffin-embedded (FFPE) blocks. Adjacent normal tissue or blood may also be taken. DNA or RNA is extracted from the cells, genomic targets are captured, libraries are prepared, and the targets of the sequencing test are amplified. The libraries are then sequenced using any one of a number of next-generation sequencing (NGS) platforms. Upon completion, millions of short reads are produced (usually 100-250 nucleotides in length) and are stored in .fastq files.

Figure 42:
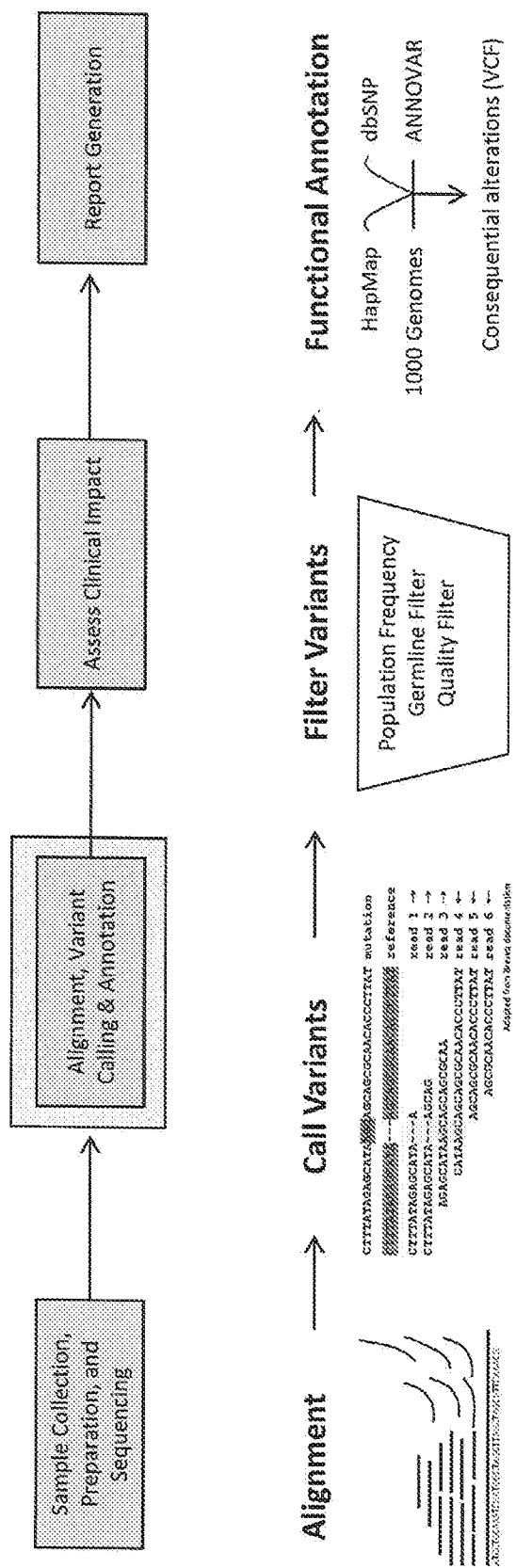
FIG. 42 shows an exemplary schematic of alignment, variant calling, and annotation for clinical sequencing.

Referring to FIG. 42, sequencing reads are first aligned to the human genome reference sequence. Depending on the sequencing technology, the number and diversity of variants could be immense, thus specific algorithms are used to identify variants in the data. These variants are then filtered based on several metrics including quality, frequency in the population, and germline/somatic classification. Variants are further filtered based on their functional classification so that only mutations with a proven or predicted consequence are retained.

Figure 43:
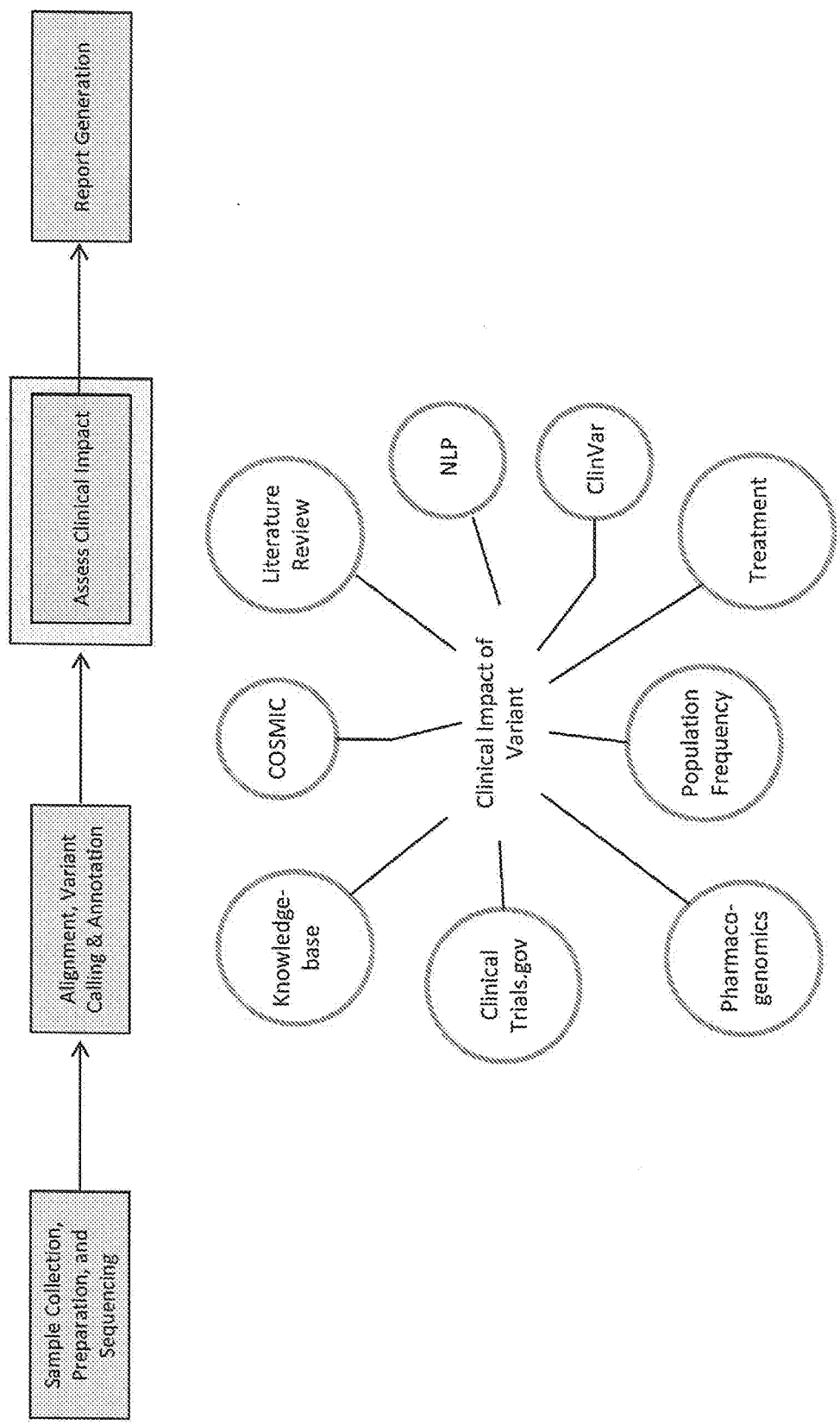
FIG. 43 shows exemplary databases for assessing a clinical impact of a variant.

Referring to FIG. 43, given a small list of variants called with high confidence, the next step is to determine their association with disease and treatment. Publically available databases are searched for known associations between variants and disease. Manual and NLP-based methods are used to gather the literature for studies linking variants to treatment and outcome. Curated data are stored in public or private knowledge databases.

Figure 44:
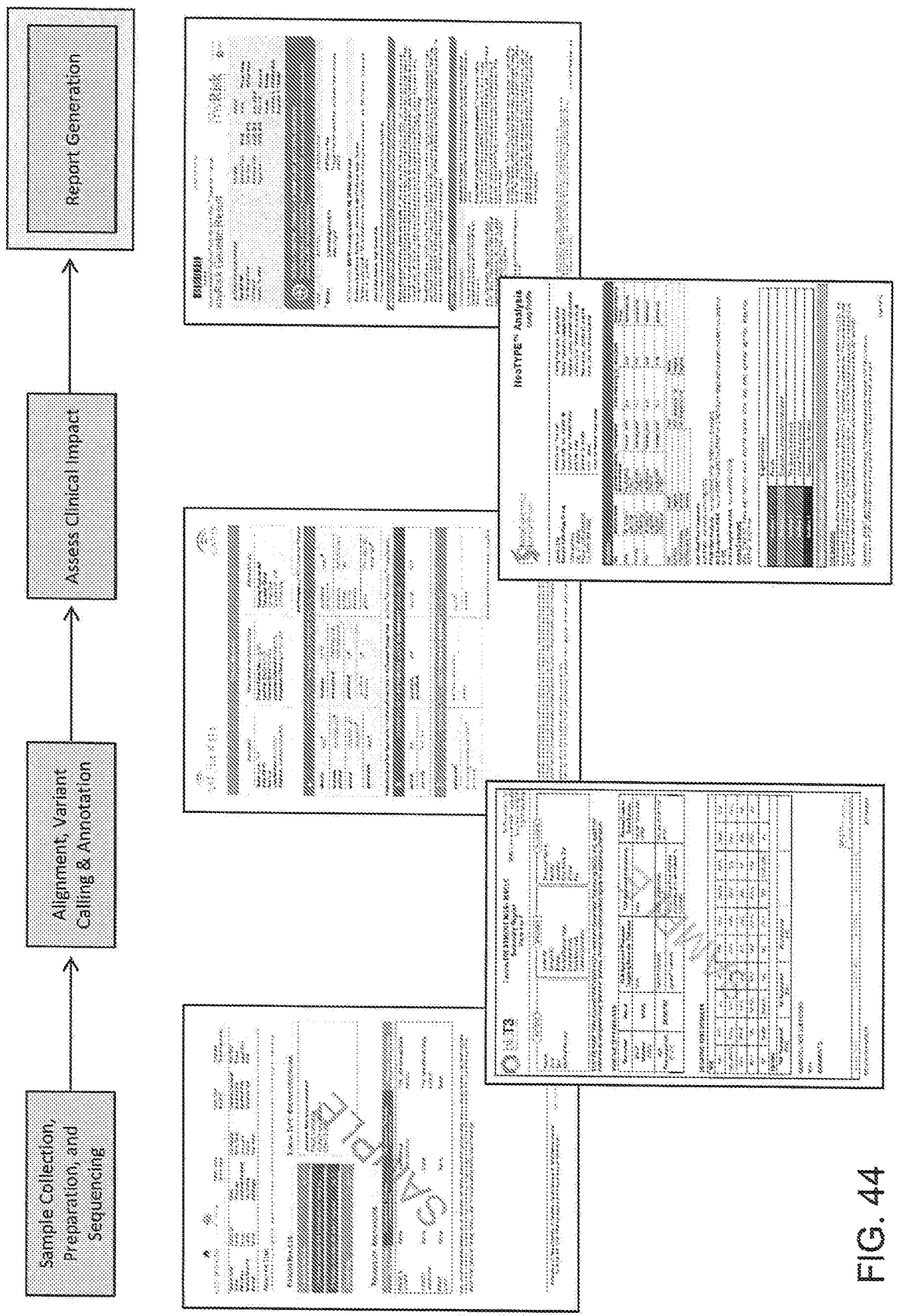
FIG. 44 shows exemplary generation of reports.

Referring to FIG. 44, after assessing the clinical impact of each variant, a report is generated, which is typically targeted to the treating physician. The content of each report varies, but in general, they typically include a summary of the variant, therapeutic susceptibilities and resistances, and open clinical trials. Reports are either manually or computationally generated. In either case, the reports are internally reviewed before being sent to the physician.

Figure 45:
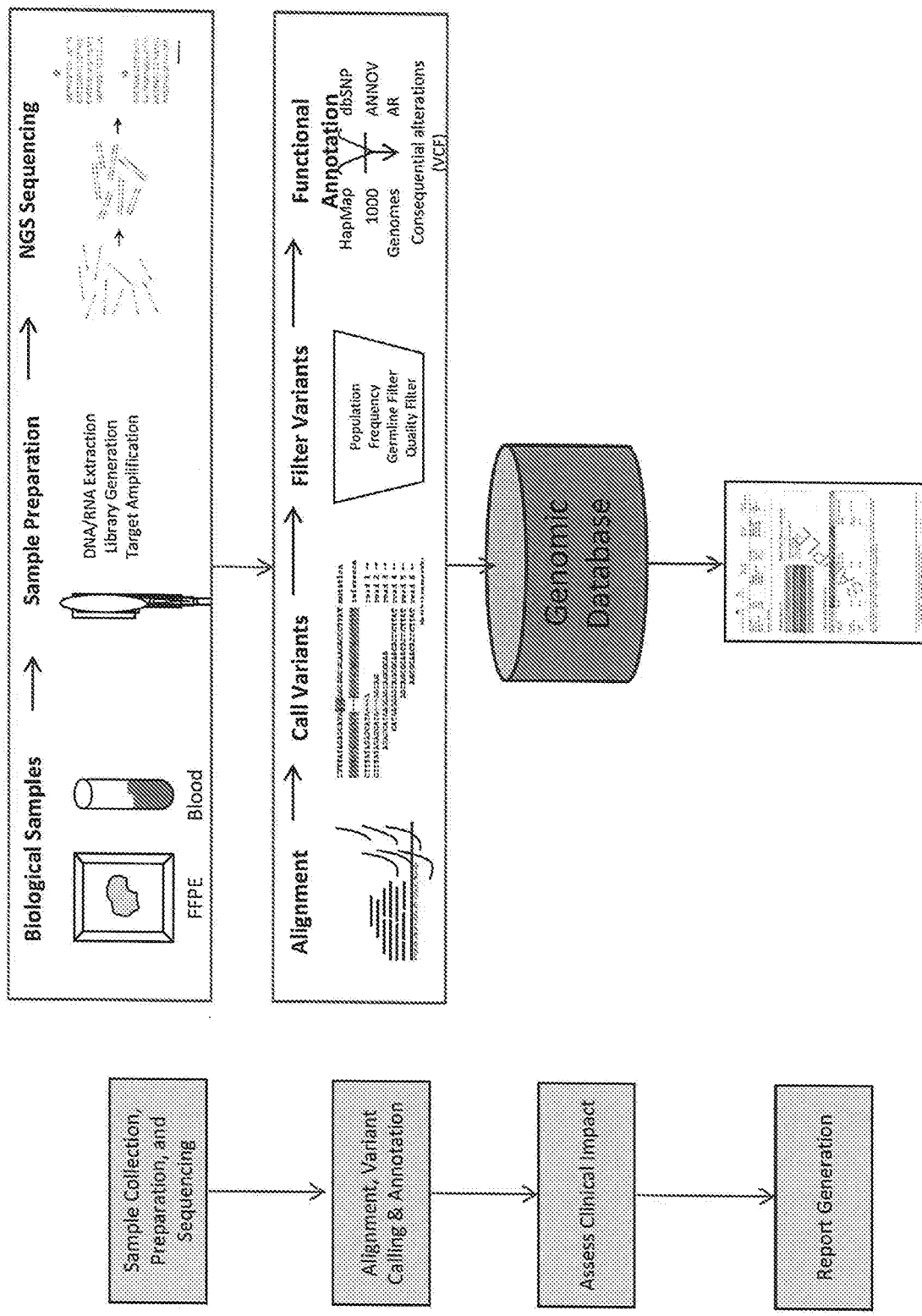
FIG. 45 shows an example of a current genomic sequencing workflow leveraging a single genomic reference database.

Referring to FIG. 45, genomics database provides details on gene variants, therapeutic susceptibilities/resistances and open clinical trials, but do not include other contextual patient information that could provide additional attributes necessary to optimize a treatment plan for a patient. Outputs of these services are limited to text based, .pdf documents that are difficult to read and understand. The contents of the report are geared to experts in the field and do not scale for novice users.

Figure 46:
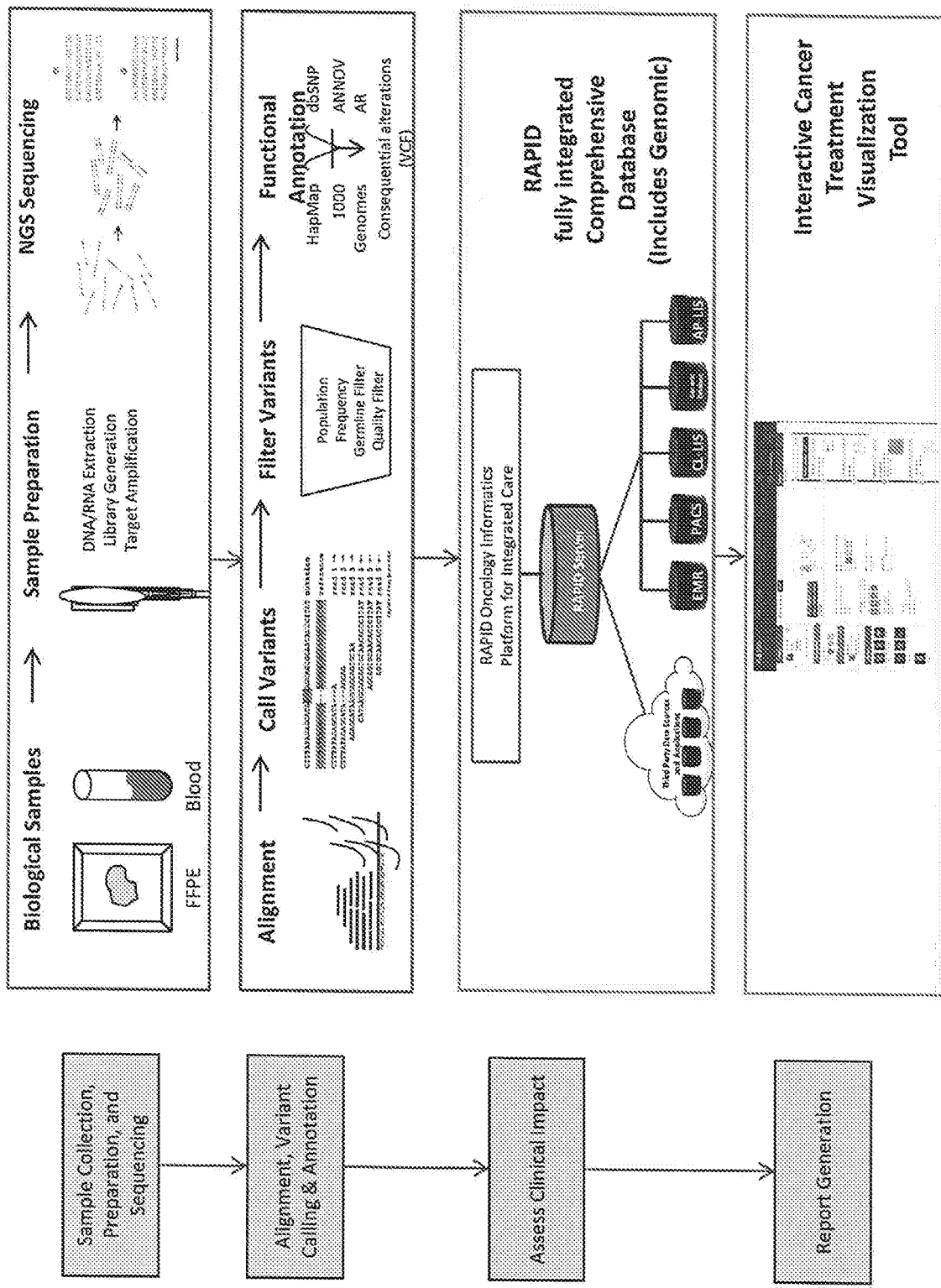
FIG. 46 shows a fully integrated, genomic sequencing workflow according to an embodiment of the present invention, hereinafter referred to as "RAPID".
Figure 47:
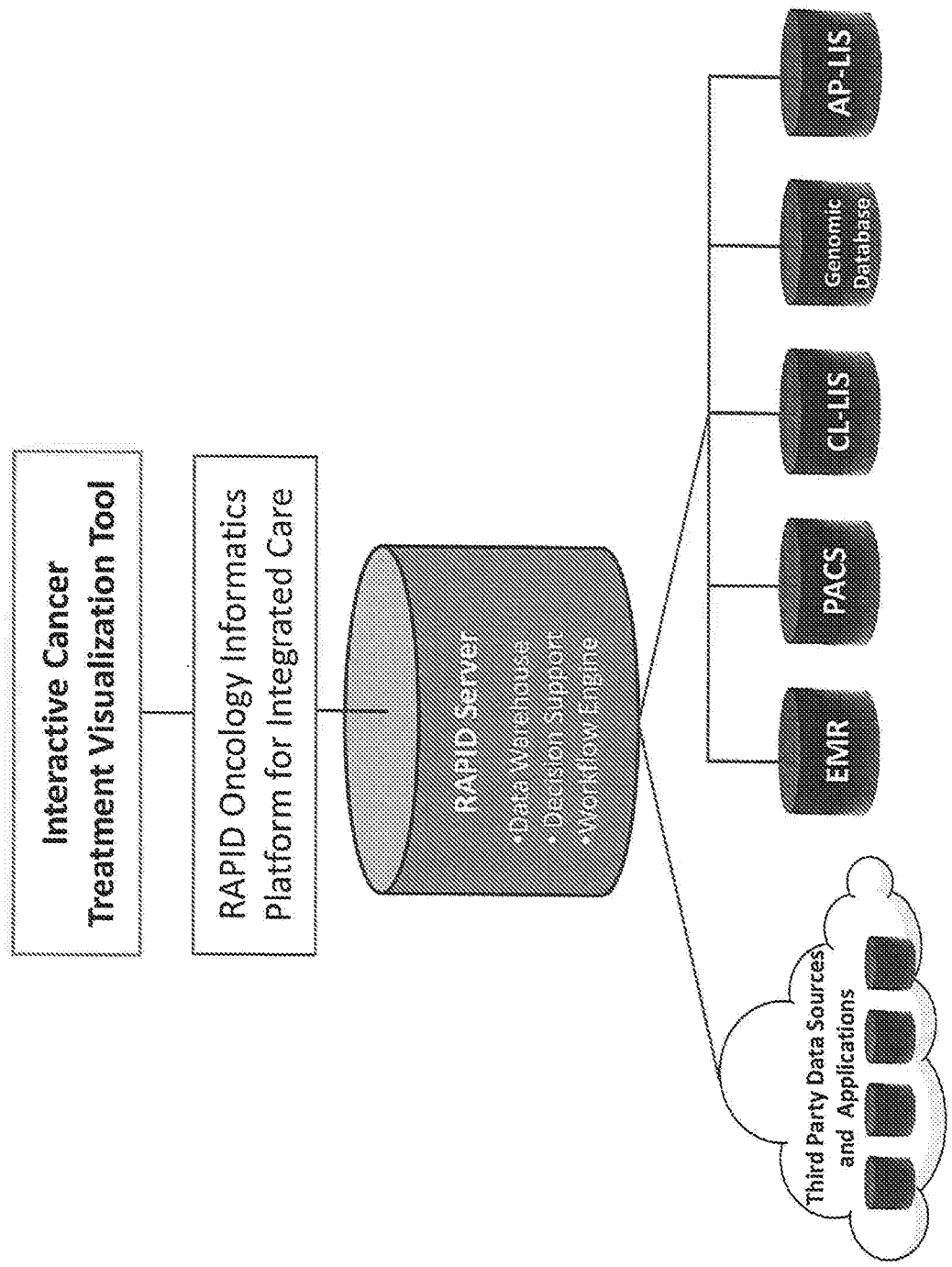
FIG. 47 shows a database integration architecture according to an embodiment of the present invention.

As shown in FIGS. 46 and 47, the RAPID, fully integrated, database made up of electronic medical records (EMR), picture archiving and communication system (PACS), CL-LIS, genomic data, AP-LIS, and other clinical content is leveraged to assess clinical impact of the variants. Rather than a static, genomic focused, .pdf report, RAPID provides a fully interactive interface that provides the user the ability to leverage the full, comprehensive medical record that includes all the disparate information systems, beyond genomic only, in its assessment of the gene variants. The RAPID interface provides a simplified means to access the information clinicians would like to review, but would have the ability to drill down to all the existing literature and information that exists on a gene variant, drug treatment, clinical trial, etc.

Figure 48:
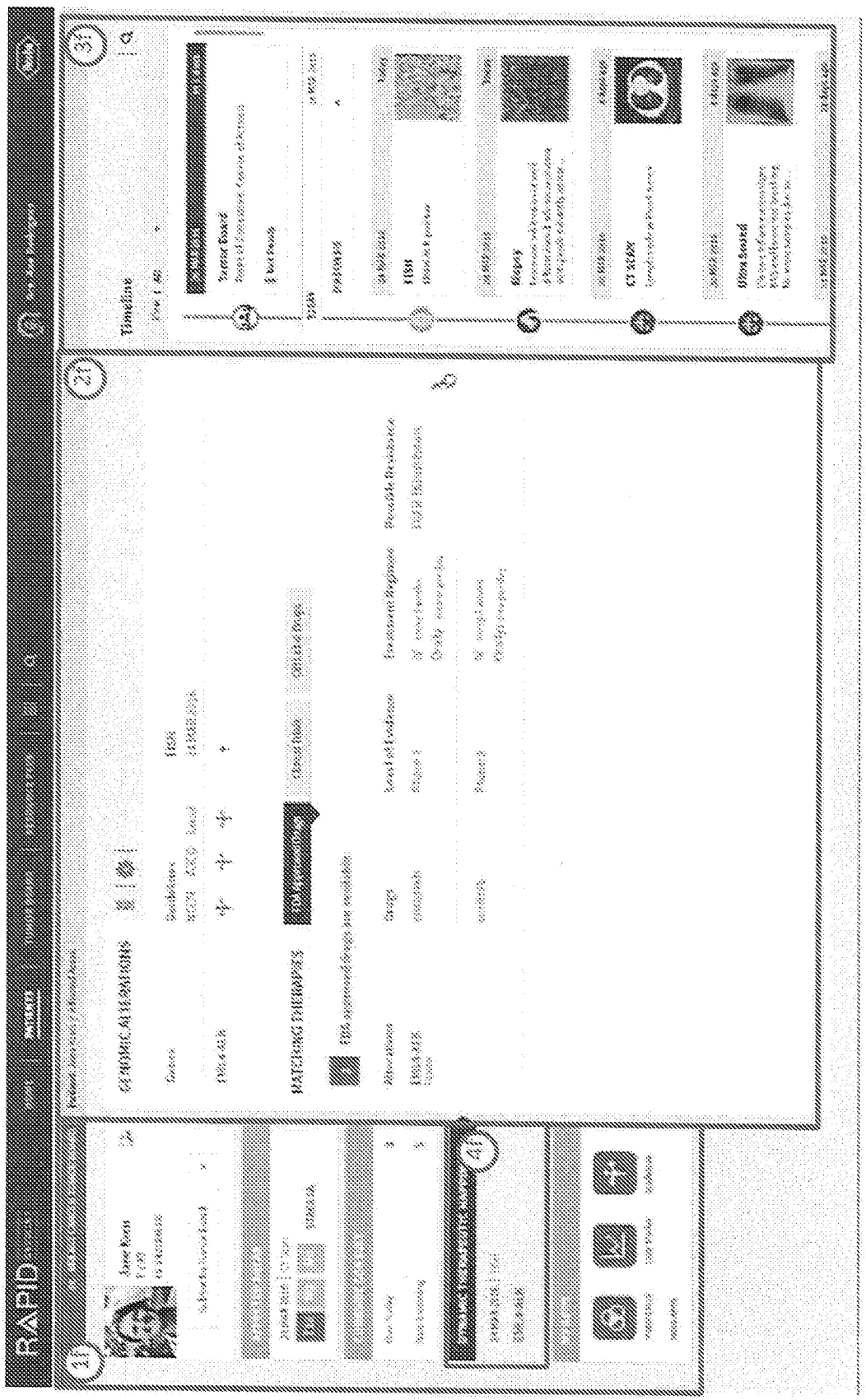
FIG. 48 shows an interactive cancer treatment visualization tool according to an embodiment of the present invention.
Figure 49:
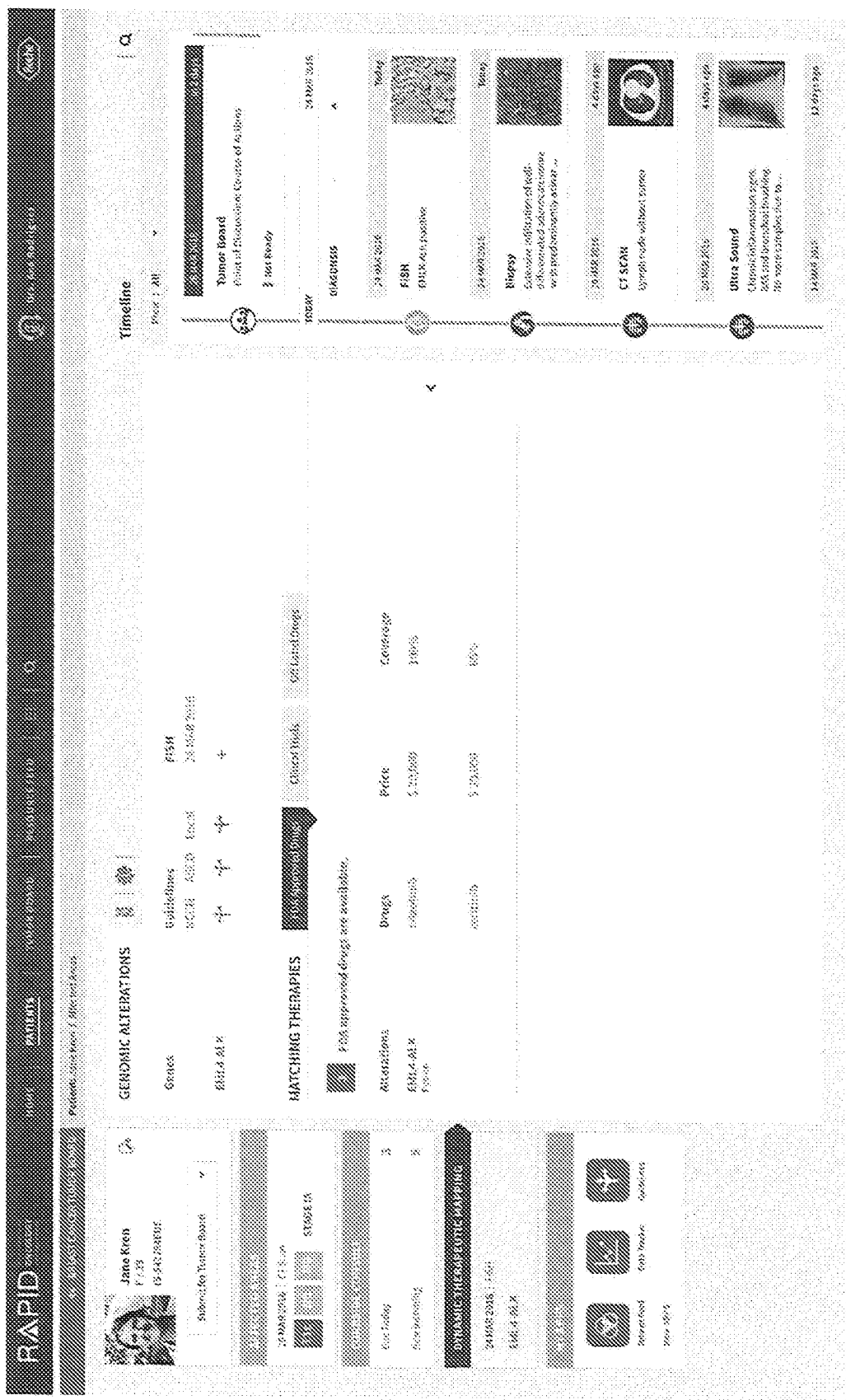
FIG. 49 shows additional drug information of an FDA approved drug for a specific genetic alteration.

Referring to FIG. 48, as indicated in section 1f, the RAPID contextual patient information can include patient overview, tumor details, collaboration, patient specific contextual apps, and dynamic therapeutic mapping. Section 2f is a workspace for the interactive cancer treatment visualization tool. In section 3f, a full, chronological patient timeline can pre-filter to display only relevant genomic tests while in workspace, however, a user would still have full interactive access to contextual patient information from any specialty. Section 4f is a dynamic therapeutic mapping display widget. Clicking on this widget launches the workspace in the center panel of the screen. Information previously found only on genomics reports can be displayed in the workspace. In FIG. 47, the genetic alteration, EML4-ALK, is displayed. RAPID can display the available guidelines for this genetic alteration from NCCN, ASCO and Local and can easily hyperlink to display the full guideline, which is a feature unavailable in pdf formats. A listing of available FDA approved drugs is also listed for this specific genetic alteration. As shown in FIG. 48, users can interactively review more detailed information on the drug, such as drug costs and percent of insurance coverage.

Figure 50:
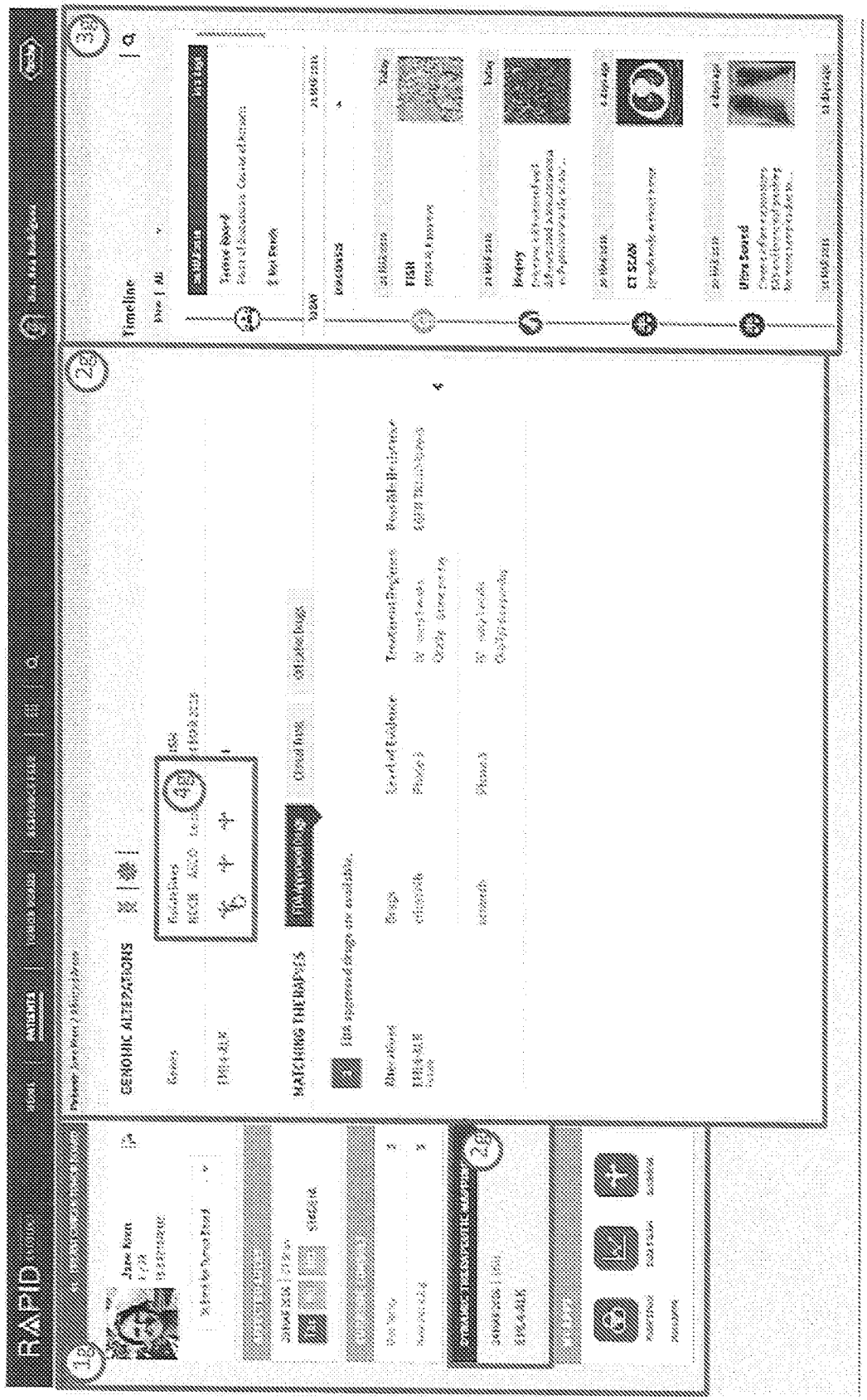
FIG. 50 shows available guidelines for a specific genetic alteration from NCCN, ASCO and Local for hyperlinking to display the full guideline.
Figure 51:
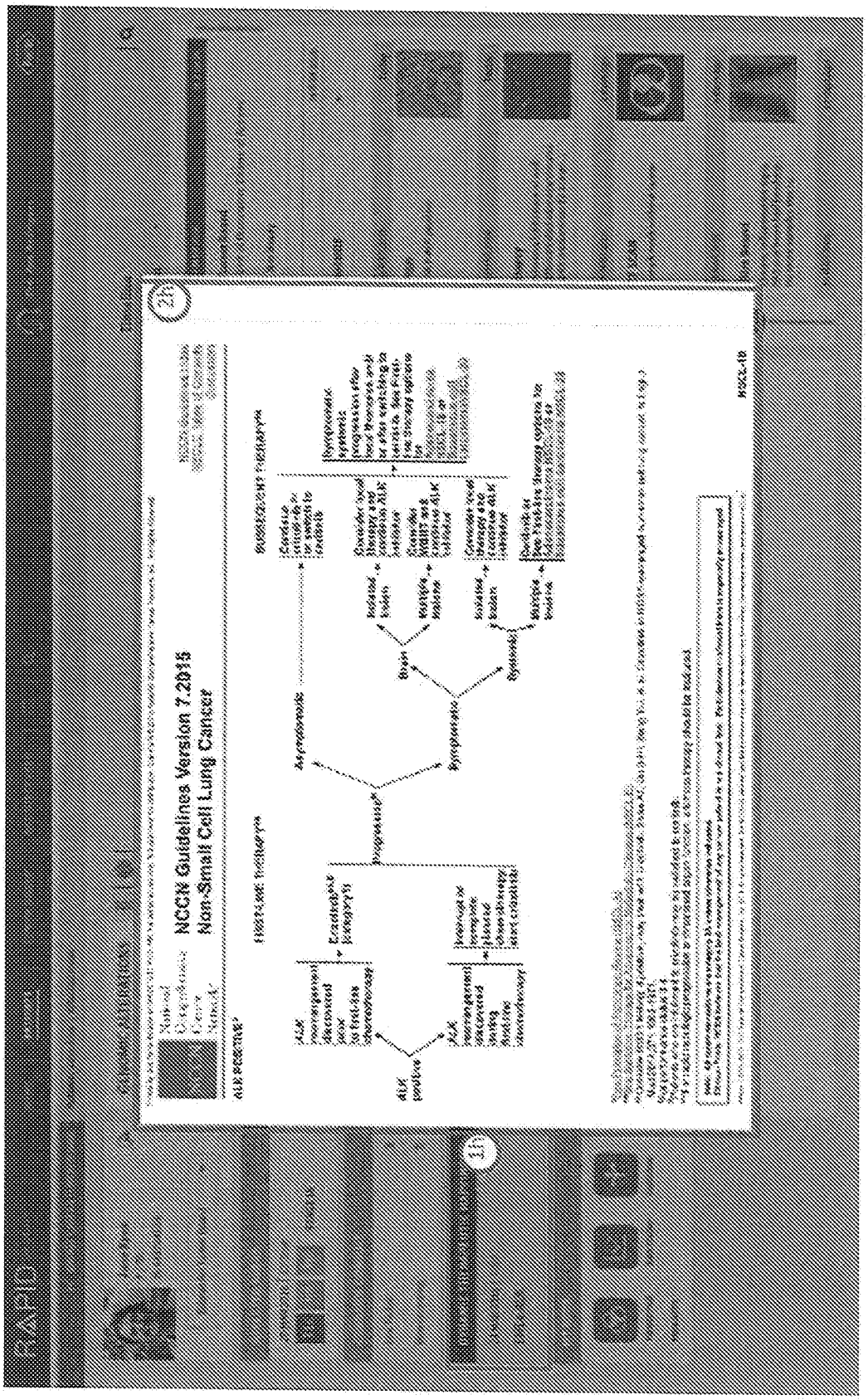
FIG. 51 shows an exemplary display of the full guideline for a specific genetic alteration.

Referring to FIGS. 50 and 51, the interface displays the available guidelines for the genetic alteration, EML4-ALK as a single example, from NCCN, ASCO and Local. Selection of a particular guideline can hyperlink to display full, available guidelines for this genetic alteration. When clicked, the hyperlink displays the full .pdf guideline from the institution of choice. Competitive genomic .pdf reports, today, do not provide access to available guidelines.

Figure 52:
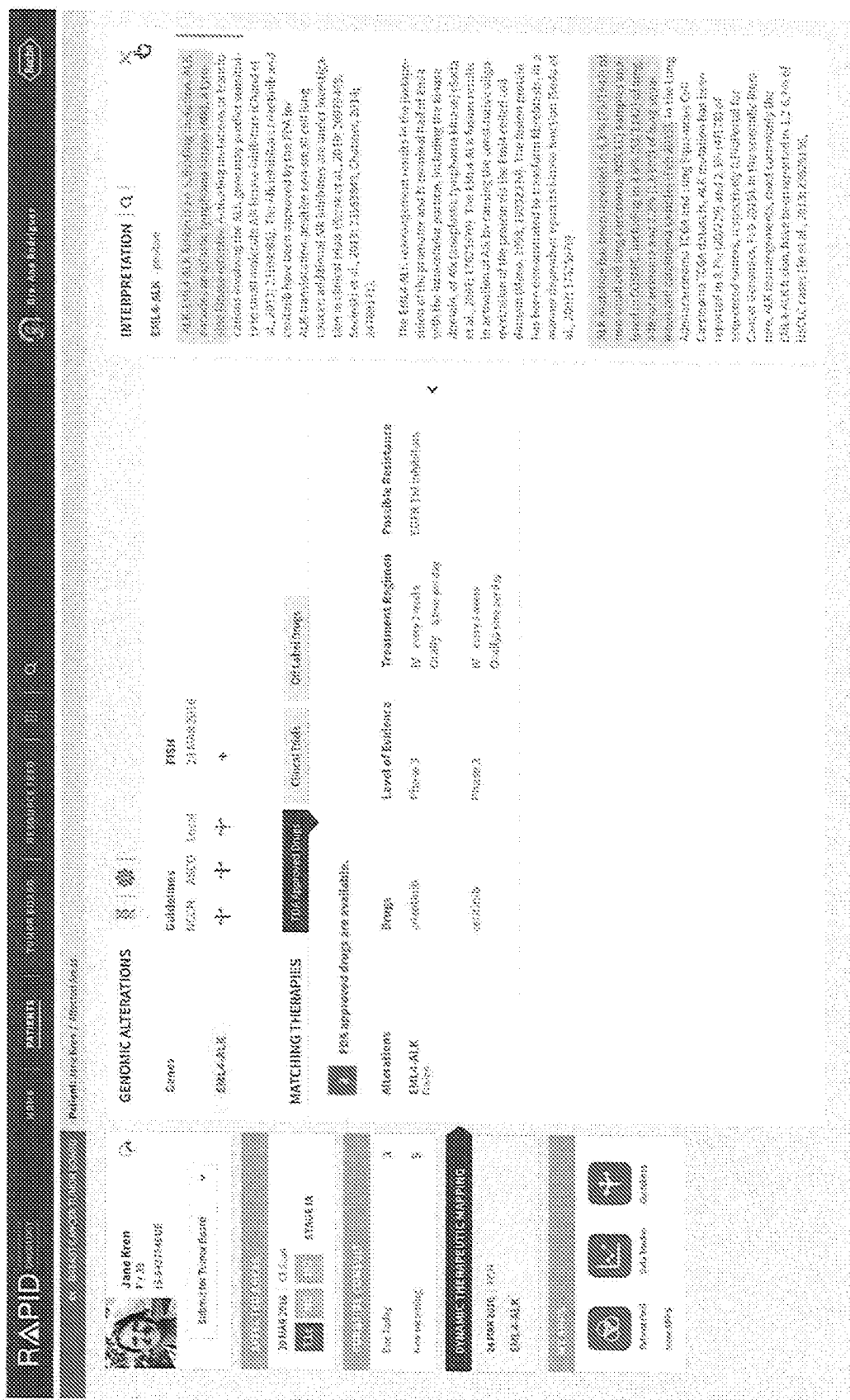
FIG. 52 shows a display of literary text relating to a specific genetic alteration. The relevant text may be highlighted.

As displayed in FIG. 52, by clicking on the genetic alteration, the interface displays existing literature text. Relevant information is highlighted in the text.

Figure 53:
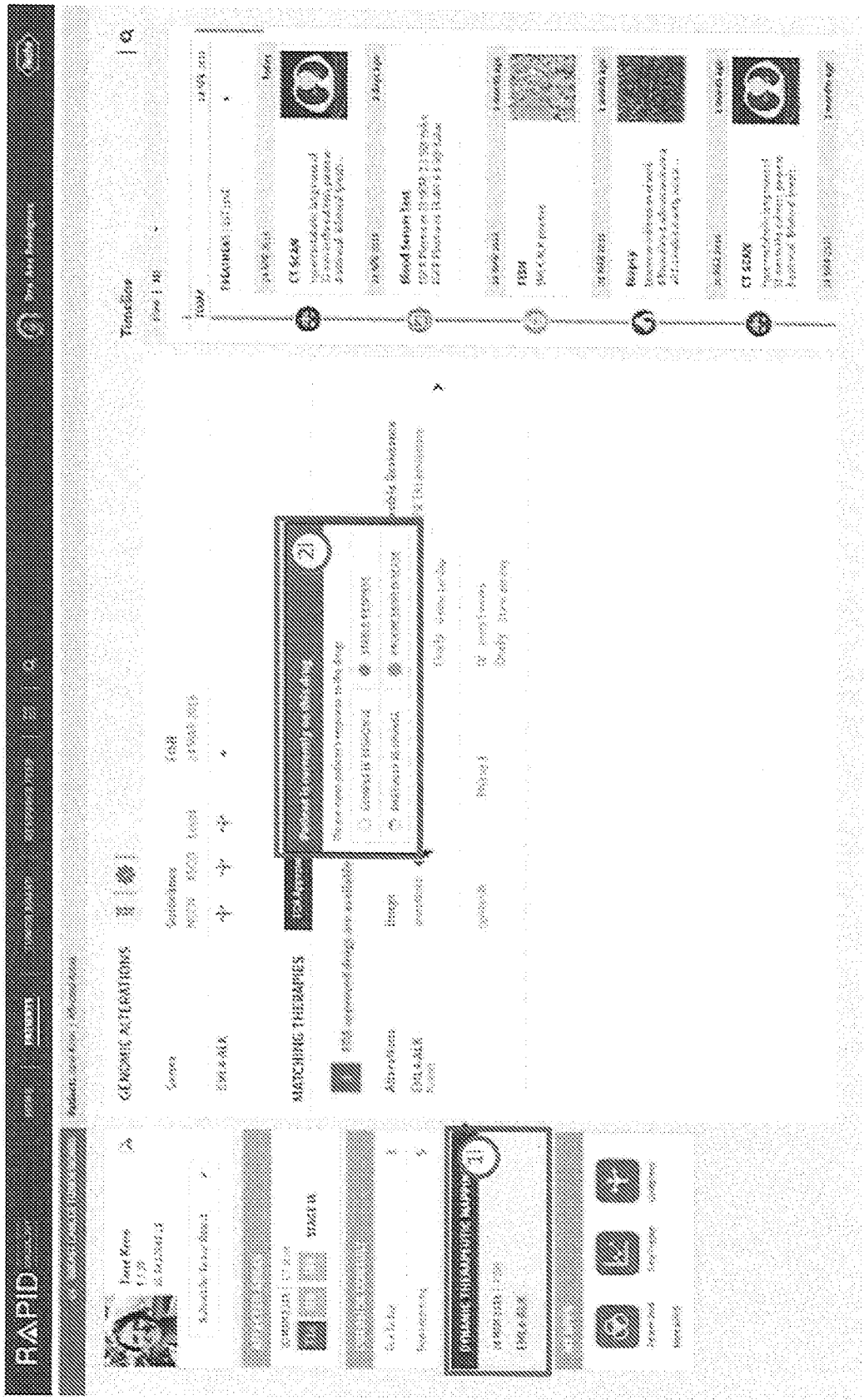
FIG. 53 shows exemplary option for a patient's response to a drug.
Figure 54:
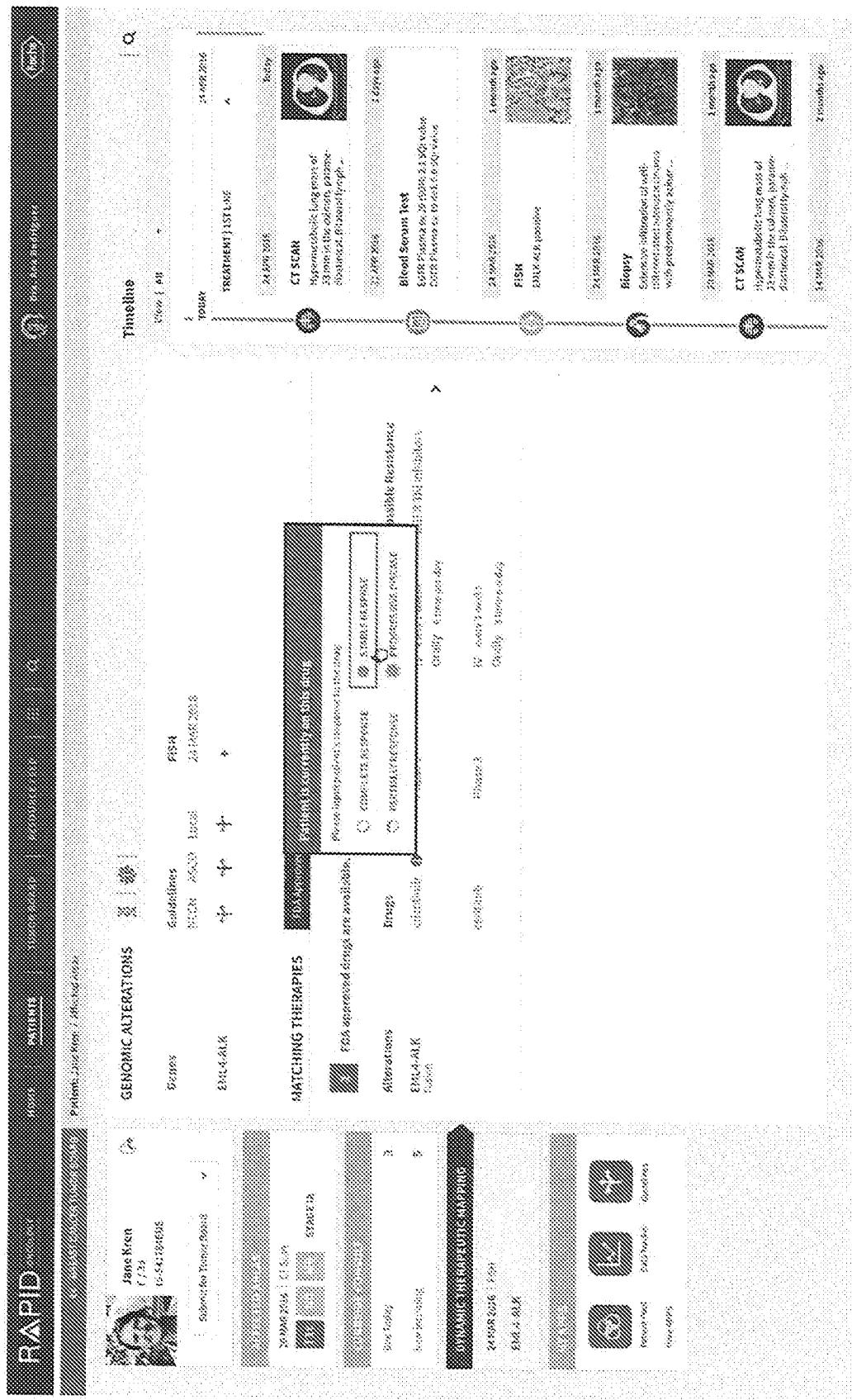
FIG. 54 shows a selection for a patient's response to a drug.
Figure 55:
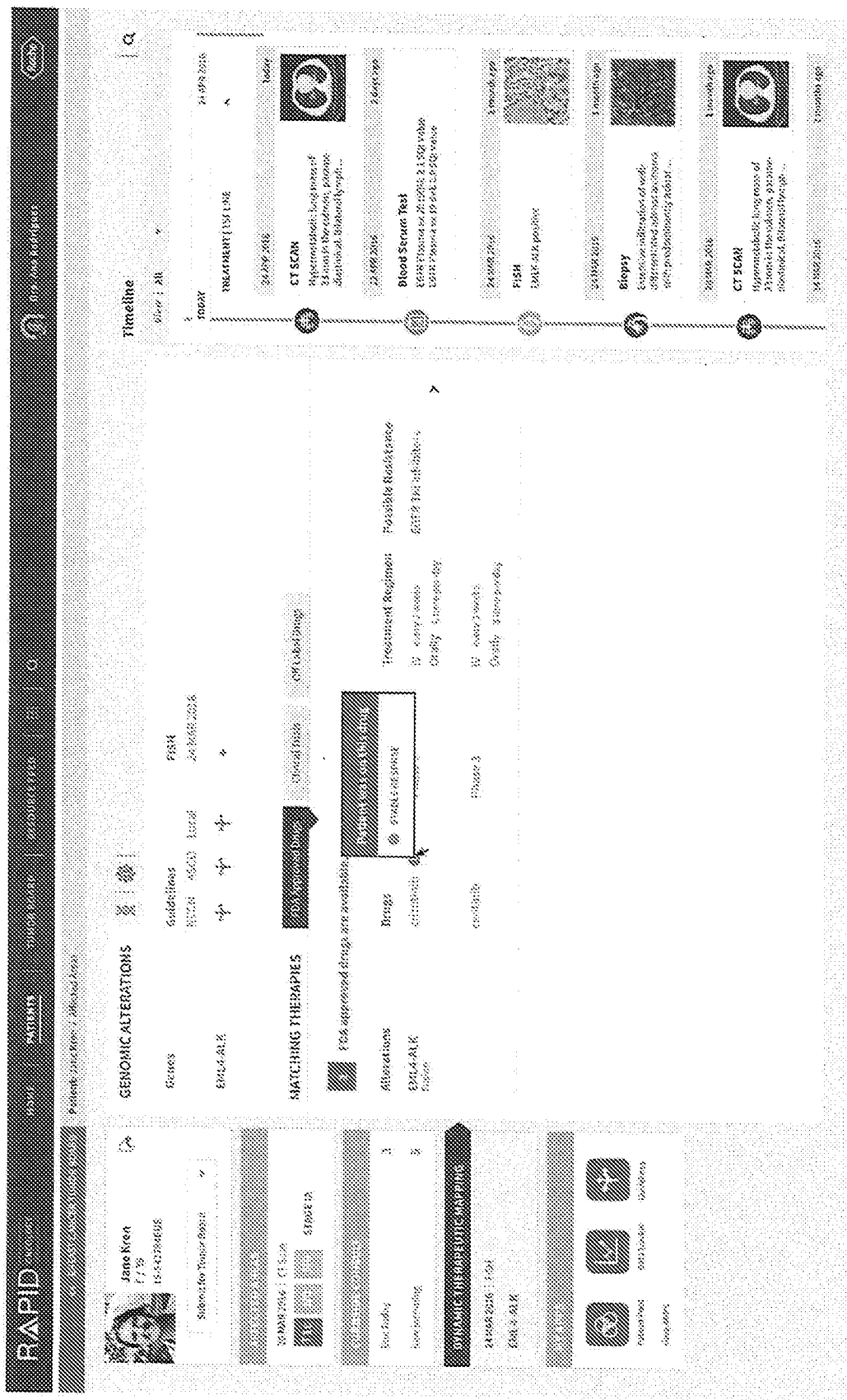
FIG. 55 shows a specific response of a patient to a drug.

As shown in FIGS. 53-55, the specific drug therapies available for gene alteration may be provided, and in addition, the patient's comprehensive medical records from a number of disparate hospital systems may be mapped to display drugs that have been previously prescribed to the patient and graphical display of how the patient has responded to the drug therapy. This is not possible from a static report.

Figure 56:
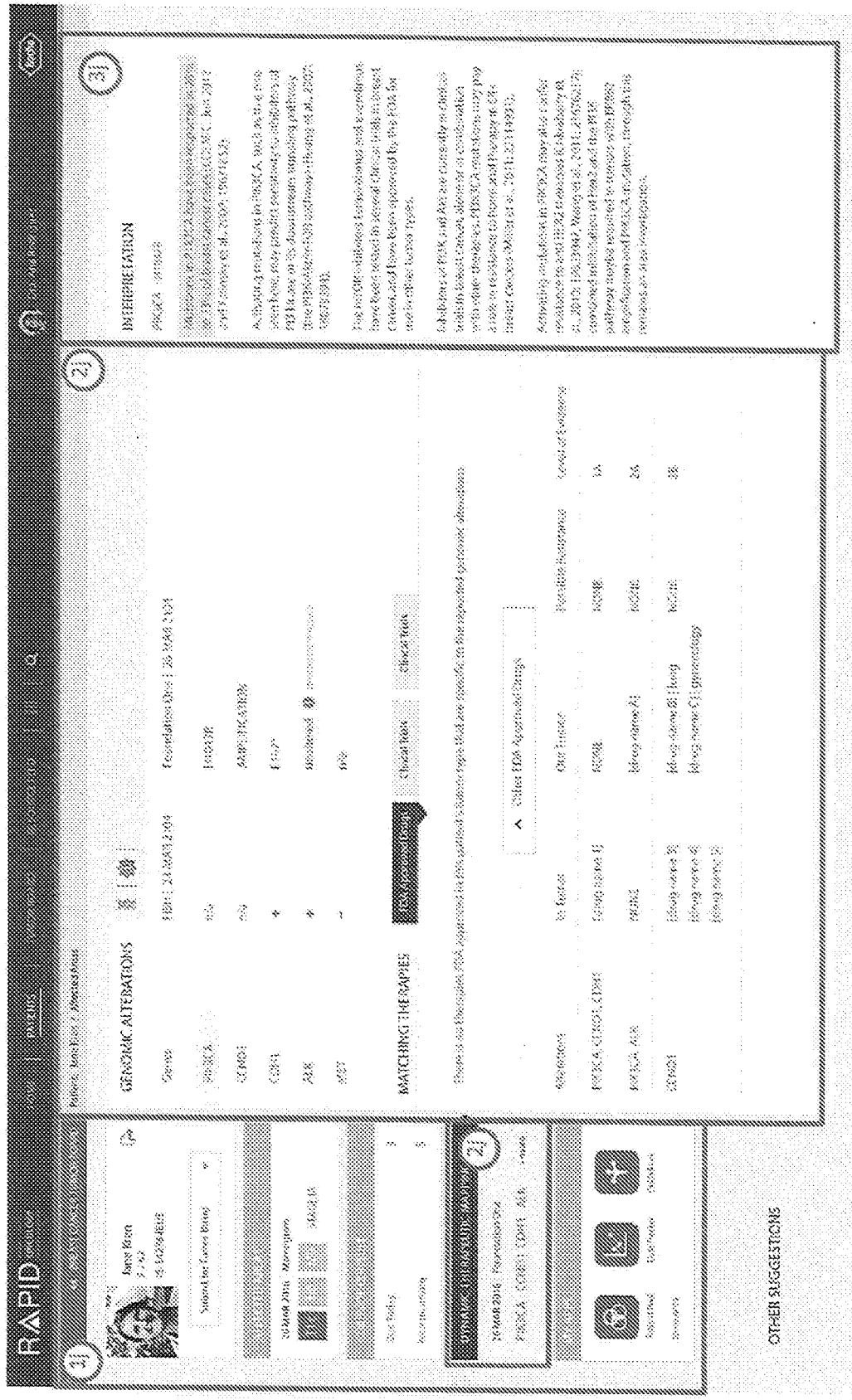
FIG. 56 shows multiple genetic alterations and interactive interface to visualize FDA approved drugs for each of the various genetic alterations that exist for each specific patient.

Referring to FIG. 56, multiple genetic, clinical trials, interactive interface to visualize FDA approved drugs for each of the various genetic alterations that exist for each specific patient can also be displayed. A knowledge-base details window pops over the chronological timeline to provide more detailed information on the genetic alteration. Rather than navigate a long .pdf document and search for specific information and lose patient context, RAPID provides a means to easily access detailed information on demand and within the patient context to maintain orientation.

Figure 57:
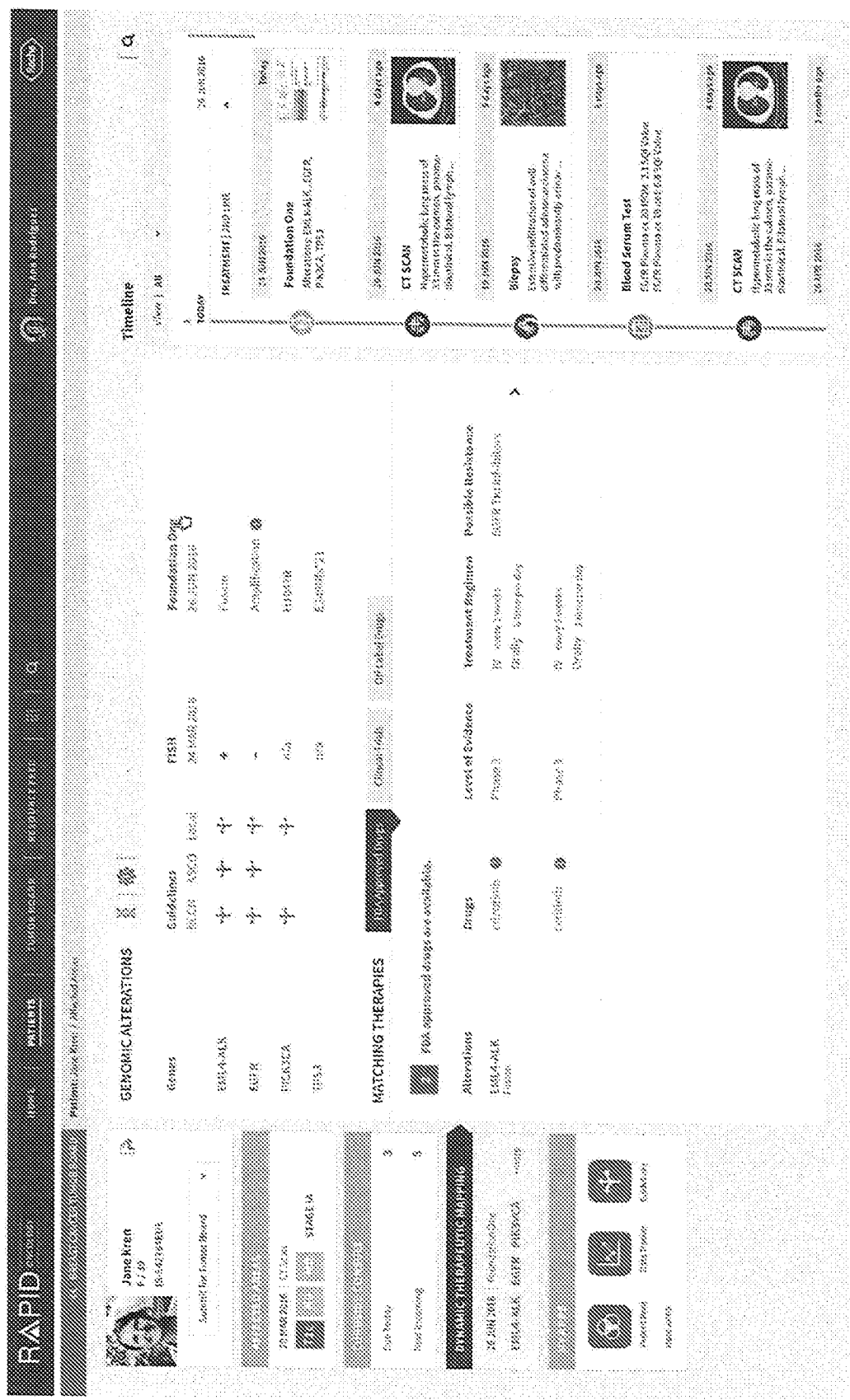
FIG. 57 shows a selection for accessing genomic reports from a source system.
Figure 58:
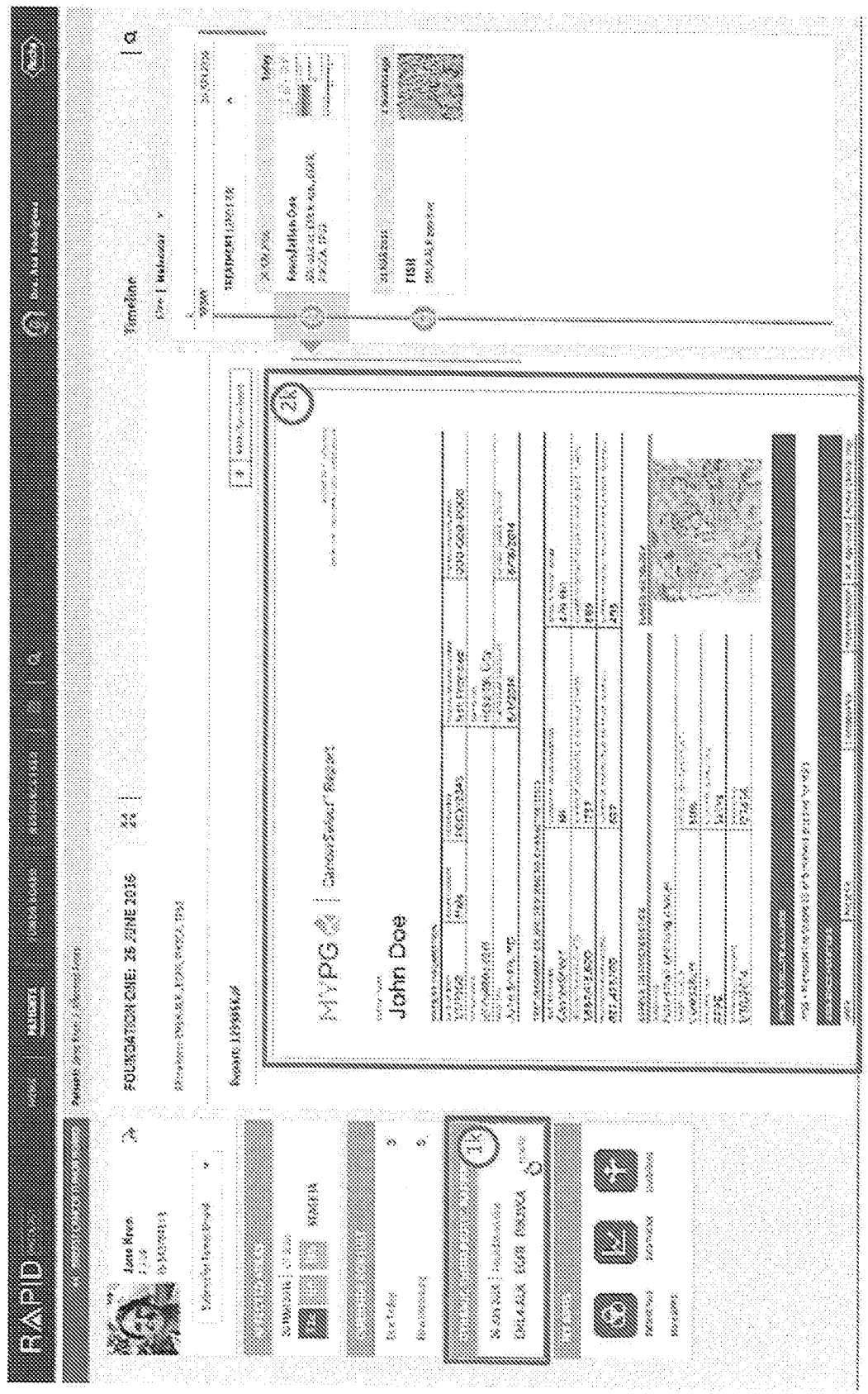
FIG. 58 shows an exemplary full, genomic report from a source system.
Figure 59:
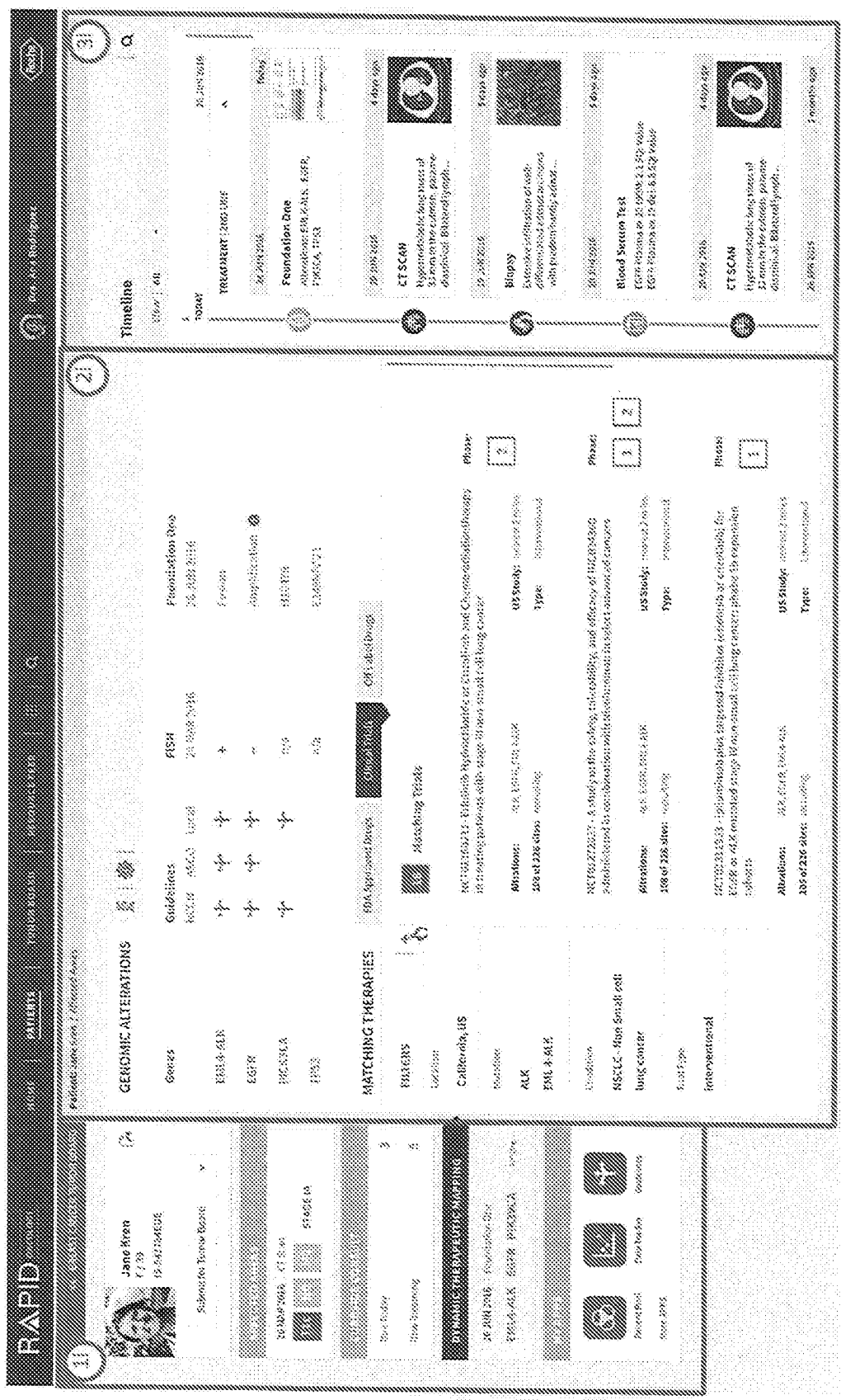
FIG. 59 shows multiple genetic alterations and interactive interface to select open clinical trials specific to these genetic alterations with filters that clinicians can further update to refine the query results.
Figure 60:
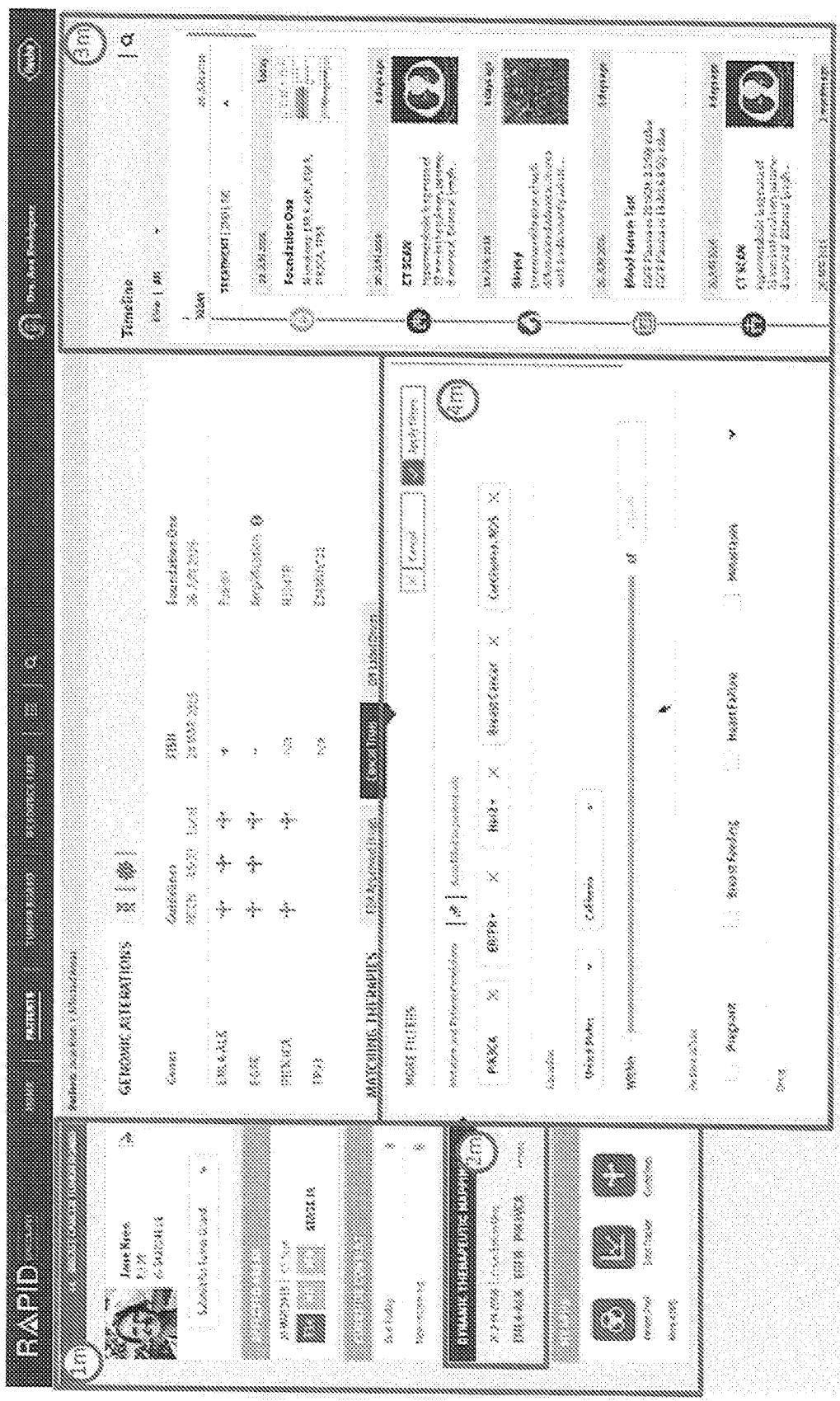
FIG. 60 shows exemplary interactive filters to refine clinical trials search
Figure 61:
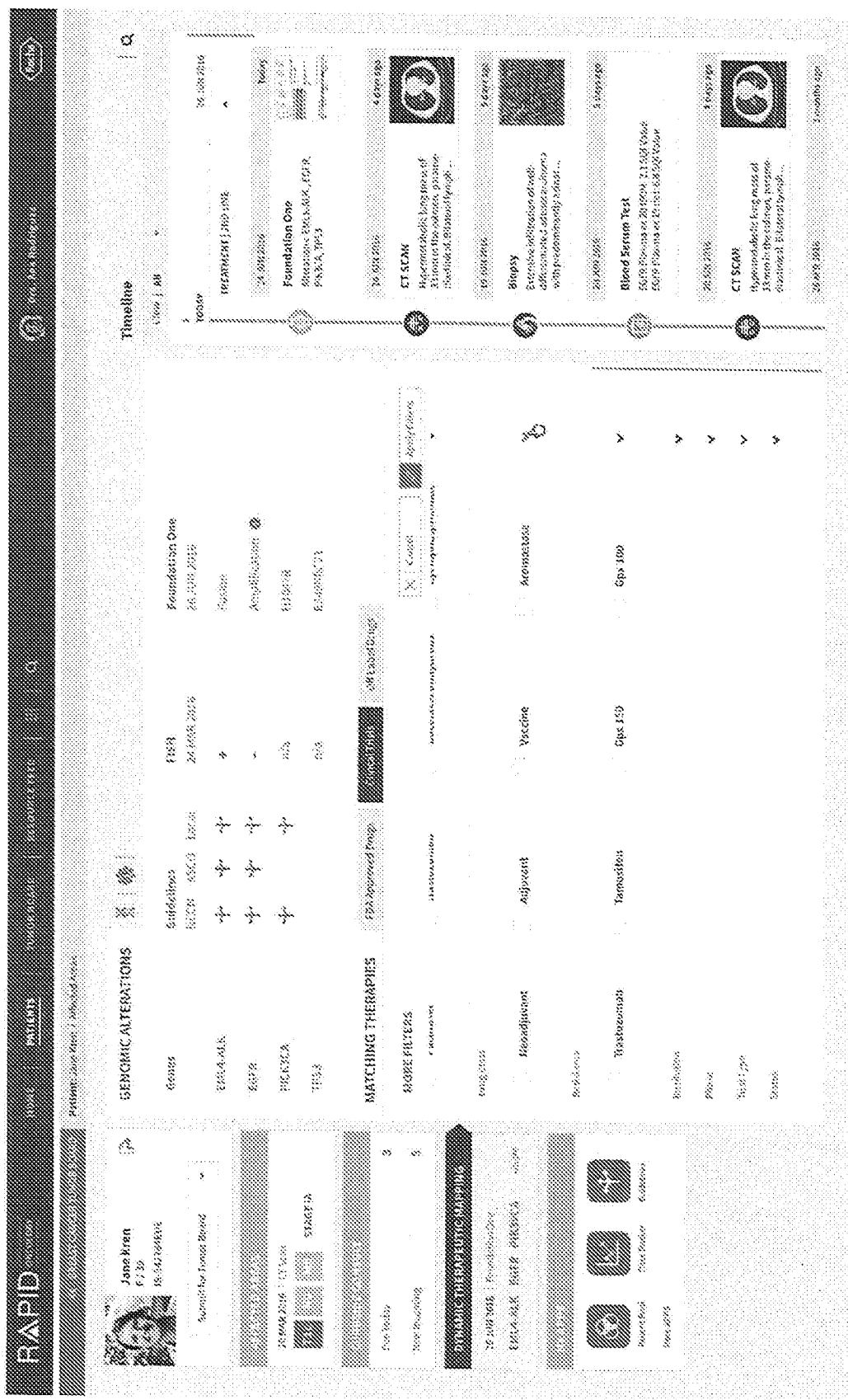
FIG. 61 shows exemplary parameters for interactive filtering.
Figure 62:
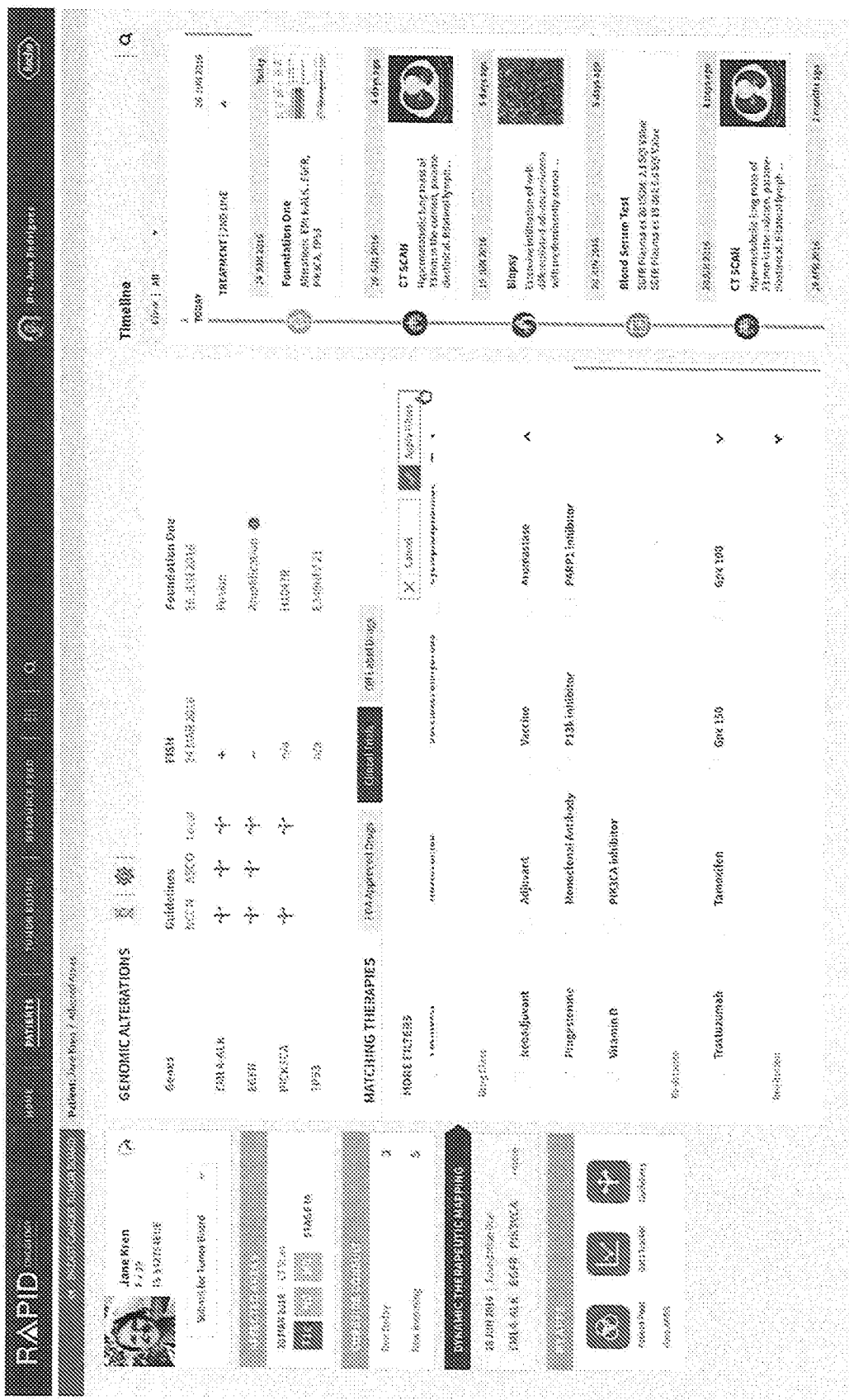
FIG. 62 shows exemplary parameters for interactive filtering.
Figure 63:
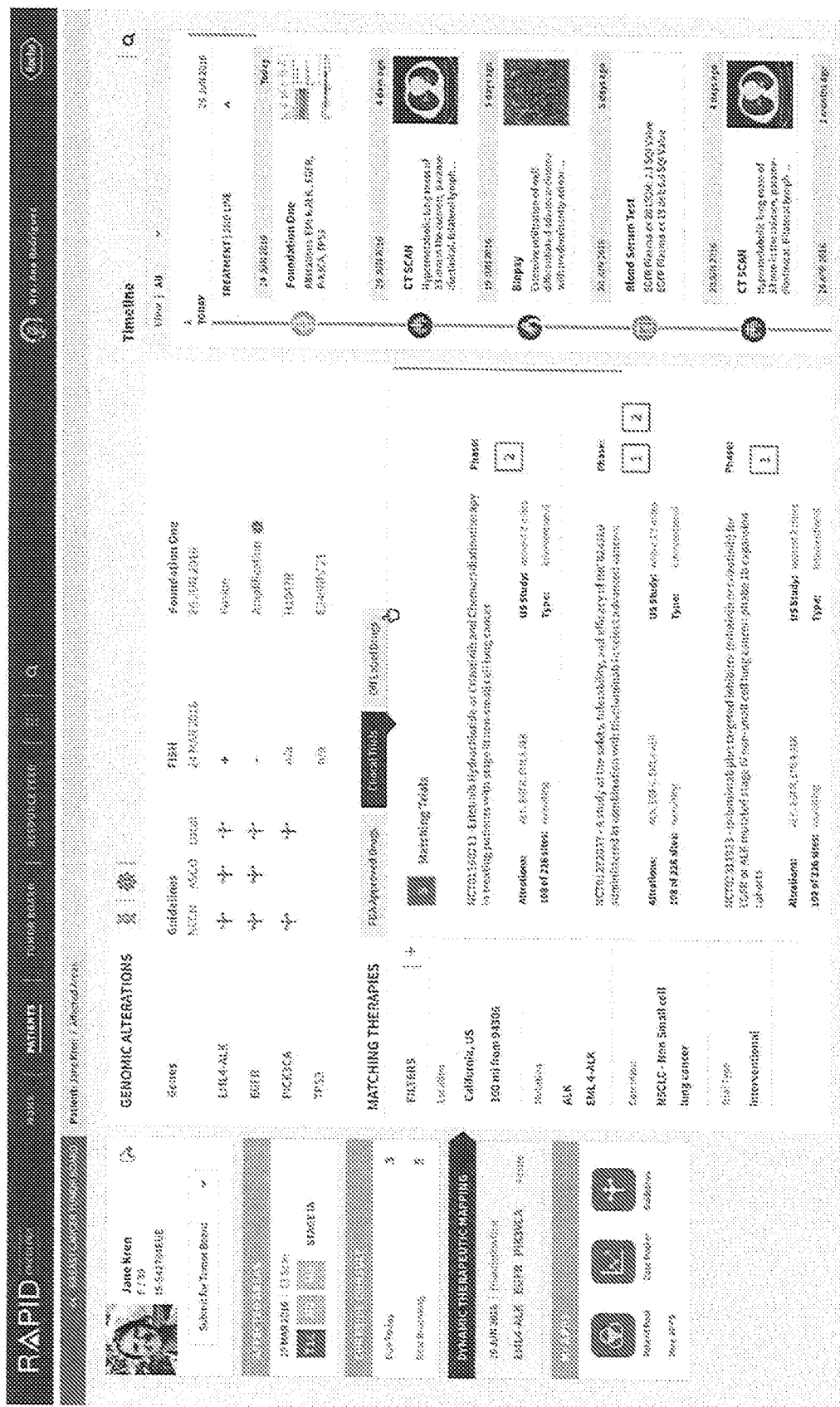
FIG. 63 shows exemplary matching trials that meet the parameters from refinement in the clinical trials search.

As shown in FIGS. 57-58, clicking on a "Foundation One" link provides access to full, genomic .pdf report from the Foundation Medicine source system as an example of 3rd party genomic report.

Referring to FIGS. 59-63, provided are multiple genetic alterations and interactive interface to select open clinical trials specific to these genetic alterations with filters that clinicians can further update to refine the query results. Full, chronological patient timeline can pre-filter to display only relevant genomic tests while in workspace; however, a user would have full interactive access to contextual patient information from any specialty. Interactive filters to refine clinical trials search provides a clinician with the ability to refine parameters that may include, but are not limited to, mutations, patient condition, location distance, other patient problems, drug class, resistance, institution, phase, trial type, status, etc. The ability to interactively adjust clinical attributes to refine search results is unique to RAPID and healthcare applications.

Figure 64:
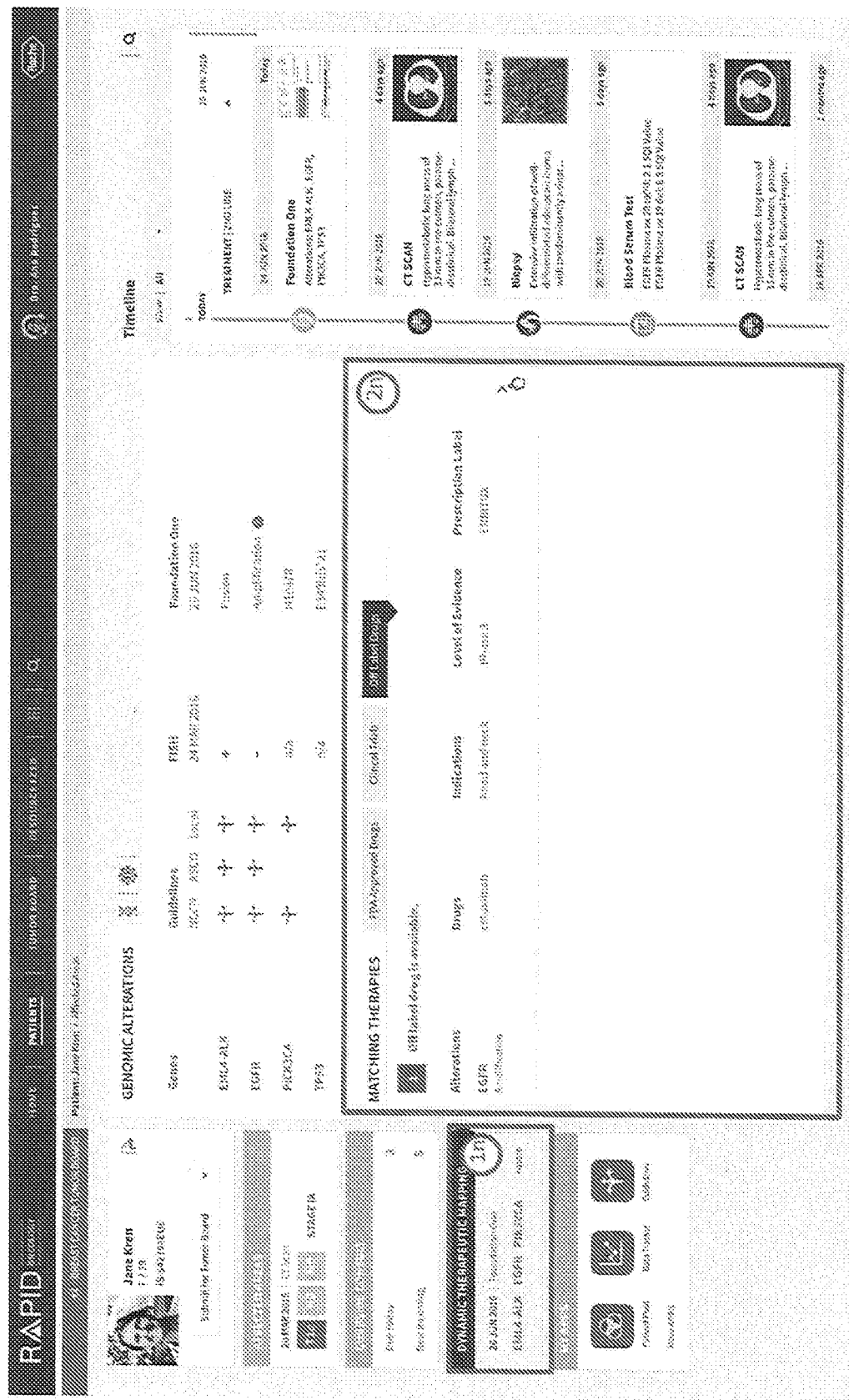
FIG. 64 shows exemplary off-label drugs for a specific genetic alteration
Figure 65:
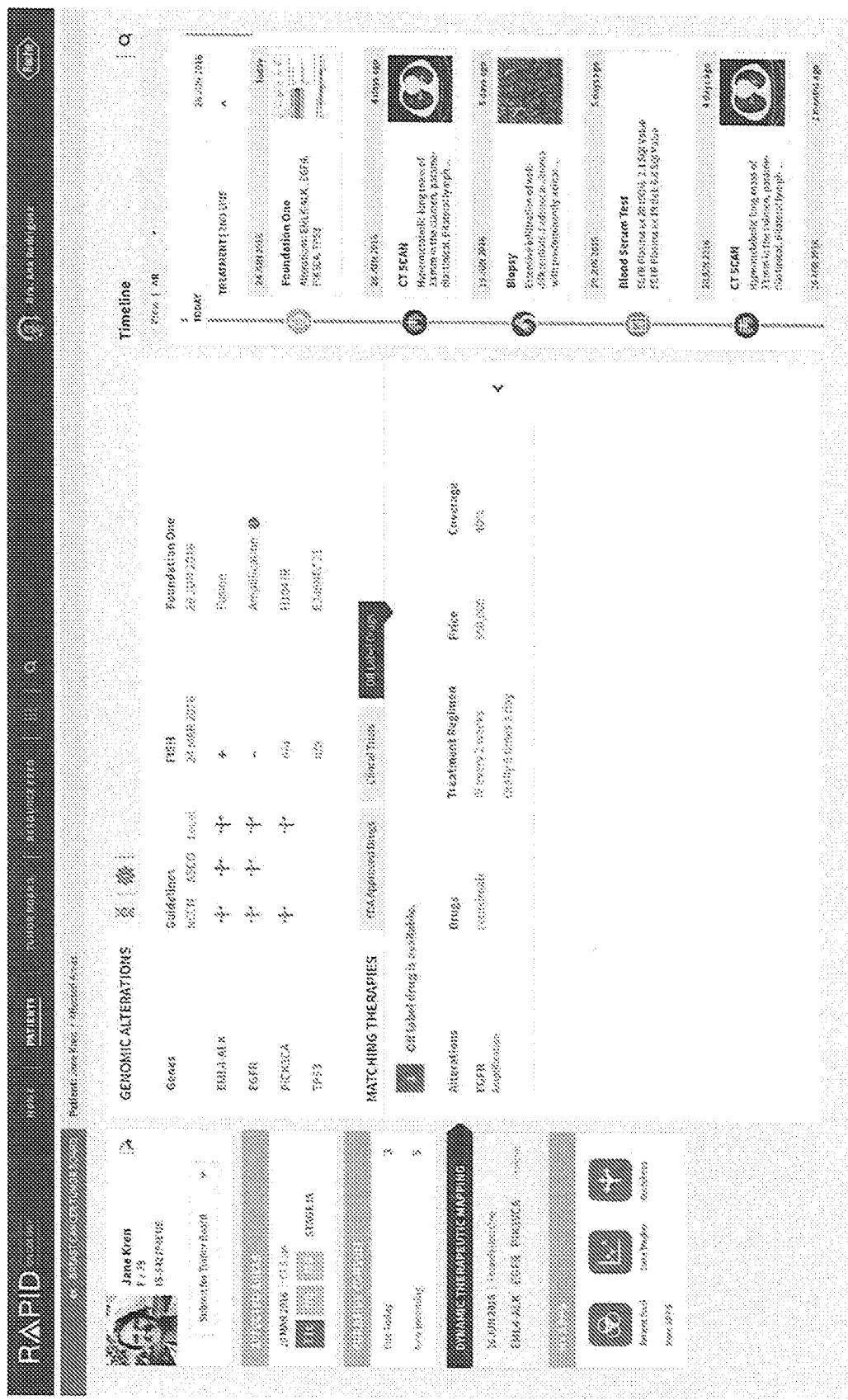
FIG. 65 shows additional information for an off-label drug.

As displayed in FIGS. 64-65, RAPID provides access to off-label drugs which are drugs that are available but not approved for FDA use for this specific gene variant. If a patient has exhausted every FDA approved drug therapy and has no available clinical trials, the use of off-label drugs may be a potential therapy option. For example, if a patient has lung cancer and no FDA approved drug or clinical trial has been successful, an off-label drug for the same genetic alteration may be provided, where the drug may be targeted to another cancer, such as that of the head and neck. Other embodiments may present additional information on the off-label drug that a clinician may take into consideration before prescribing the off-label drug as a possible treatment option. For example, FIG. 65 displays drug costs and the percentage that an insurer will cover.

Computers or computing systems described herein may include various components, such as a processor, an operating system, system memory, memory storage devices, input-output controllers, input-output devices, and display devices. It will also be understood by those of ordinary skill in the relevant art that there are many possible configurations and components of a computer and may also include cache memory, a data backup unit, and many other devices. Examples of input devices include a keyboard, a cursor control devices (e.g., a mouse), a microphone, a scanner, and so forth. Examples of output devices include a display device (e.g., a monitor or projector), speakers, a printer, a network card, and so forth. Display devices may include display devices that provide visual information, this information typically may be logically and/or physically organized as an array of pixels. An interface controller may also be included that may comprise any of a variety of known or future software programs for providing input and output interfaces. For example, interfaces may include what are generally referred to as "Graphical User Interfaces" (often referred to as GUI's) that provides one or more graphical representations to a user. Interfaces are typically enabled to accept user inputs using means of selection or input known to those of ordinary skill in the related art. The interface may also be a touch screen device. In the same or alternative embodiments, applications on a computer may employ an interface that includes what are referred to as "command line interfaces" (often referred to as CLI's). CLI's typically provide a text based interaction between an application and a user. Typically, command line interfaces present output and receive input as lines of text through display devices. For example, some implementations may include what are referred to as a "shell" such as Unix Shells known to those of ordinary skill in the related art, or Microsoft Windows Powershell that employs object-oriented type programming architectures such as the Microsoft .NET framework.

Those of ordinary skill in the related art will appreciate that interfaces may include one or more GUI's, CLI's or a combination thereof. A processor may include a commercially available processor such as a Celeron, Core, or Pentium processor made by Intel Corporation, a SPARC processor made by Sun Microsystems, an Athlon, Sempron, Phenom, or Opteron processor made by AMD Corporation, or it may be one of other processors that are or will become available. Some embodiments of a processor may include what is referred to as multi-core processor and/or be enabled to employ parallel processing technology in a single or multi-core configuration. For example, a multi-core architecture typically comprises two or more processor "execution cores". In the present example, each execution core may perform as an independent processor that enables parallel execution of multiple threads. In addition, those of ordinary skill in the related will appreciate that a processor may be configured in what is generally referred to as 32 or 64 bit architectures, or other architectural configurations now known or that may be developed in the future.

A processor typically executes an operating system, which may be, for example, a Windows type operating system from the Microsoft Corporation; the Mac OS X operating system from Apple Computer Corp.; a Unix or Linux-type operating system available from many vendors or what is referred to as an open source; another or a future operating system; or some combination thereof. An operating system interfaces with firmware and hardware in a well-known manner, and facilitates the processor in coordinating and executing the functions of various computer programs that may be written in a variety of programming languages. An operating system, typically in cooperation with a processor, coordinates and executes functions of the other components of a computer. An operating system also provides scheduling, input-output control, file and data management, memory management, and communication control and related services, all in accordance with known techniques.

System memory may include any of a variety of known or future memory storage devices that can be used to store the desired information and that can be accessed by a computer. Computer readable storage media may include volatile and non-volatile, removable and non-removable media implemented in any method or technology for storage of information such as computer readable instructions, data structures, program modules, or other data. Examples include any commonly available random access memory (RAM), read-only memory (ROM), electronically erasable programmable read-only memory (EEPROM), digital versatile disks (DVD), magnetic medium, such as a resident hard disk or tape, an optical medium such as a read and write compact disc, or other memory storage device. Memory storage devices may include any of a variety of known or future devices, including a compact disk drive, a tape drive, a removable hard disk drive, USB or flash drive, or a diskette drive. Such types of memory storage devices typically read from, and/or write to, a program storage medium such as, respectively, a compact disk, magnetic tape, removable hard disk, USB or flash drive, or floppy diskette. Any of these program storage media, or others now in use or that may later be developed, may be considered a computer program product. As will be appreciated, these program storage media typically store a computer software program and/or data. Computer software programs, also called computer control logic, typically are stored in system memory and/or the program storage device used in conjunction with memory storage device. In some embodiments, a computer program product is described comprising a computer usable medium having control logic (computer software program, including program code) stored therein. The control logic, when executed by a processor, causes the processor to perform functions described herein. In other embodiments, some functions are implemented primarily in hardware using, for example, a hardware state machine. Implementation of the hardware state machine so as to perform the functions described herein will be apparent to those skilled in the relevant arts. Input-output controllers could include any of a variety of known devices for accepting and processing information from a user, whether a human or a machine, whether local or remote. Such devices include, for example, modem cards, wireless cards, network interface cards, sound cards, or other types of controllers for any of a variety of known input devices. Output controllers could include controllers for any of a variety of known display devices for presenting information to a user, whether a human or a machine, whether local or remote. In the presently described embodiment, the functional elements of a computer communicate with each other via a system bus. Some embodiments of a computer may communicate with some functional elements using network or other types of remote communications. As will be evident to those skilled in the relevant art, an instrument control and/or a data processing application, if implemented in software, may be loaded into and executed from system memory and/or a memory storage device. All or portions of the instrument control and/or data processing applications may also reside in a read-only memory or similar device of the memory storage device, such devices not requiring that the instrument control and/or data processing applications first be loaded through input-output controllers. It will be understood by those skilled in the relevant art that the instrument control and/or data processing applications, or portions of it, may be loaded by a processor, in a known manner into system memory, or cache memory, or both, as advantageous for execution. Also, a computer may include one or more library files, experiment data files, and an internet client stored in system memory. For example, experiment data could include data related to one or more experiments or assays, such as detected signal values, or other values associated with one or more sequencing by synthesis (SBS) experiments or processes. Additionally, an internet client may include an application enabled to access a remote service on another computer using a network and may for instance comprise what are generally referred to as "Web Browsers". In the present example, some commonly employed web browsers include Microsoft Internet Explorer available from Microsoft Corporation, Mozilla Firefox from the Mozilla Corporation, Safari from Apple Computer Corp., Google Chrome from the Google Corporation, or other type of web browser currently known in the art or to be developed in the future. Also, in the same or other embodiments an Internet client may include, or could be an element of, specialized software applications enabled to access remote information via a network such as a data processing application for biological applications.

A network may include one or more of the many various types of networks well known to those of ordinary skill in the art. For example, a network may include a local or wide area network that may employ what is commonly referred to as a TCP/IP protocol suite to communicate. A network may include a network comprising a worldwide system of interconnected computer networks that is commonly referred to as the Internet, or could also include various intranet architectures. Those of ordinary skill in the related arts will also appreciate that some users in networked environments may prefer to employ what are generally referred to as "firewalls" (also sometimes referred to as Packet Filters, or Border Protection Devices) to control information traffic to and from hardware and/or software systems. For example, firewalls may comprise hardware or software elements or some combination thereof and are typically designed to enforce security policies put in place by users, such as for instance network administrators, etc.

Although the figures herein may show a specific order of method steps, the order of the steps may differ from what is depicted. Also, two or more steps may be performed concurrently or with partial concurrence. Variations in step performance can depend on the software and hardware systems chosen and on designer choice. All such variations are within the scope of the application. Software implementations could be accomplished with standard programming techniques, with rule based logic and other logic to accomplish the various connection steps, processing steps, comparison steps and decision steps.

It should be understood that the identified embodiments are offered by way of example only. Other substitutions, modifications, changes and omissions may be made in the design, operating conditions and arrangement of the embodiments without departing from the scope of the present application. Accordingly, the present application is not limited to a particular embodiment, but extends to various modifications that nevertheless fall within the scope of the application. It should also be understood that the phraseology and terminology employed herein is for the purpose of description only and should not be regarded as limiting.

What is claimed is:

1. A system communicatively coupled to a plurality of information systems, the system comprising an informatics platform and a database, wherein:
   the database is configured to aggregate and store medical data obtained by the system from the plurality of information systems; and
   the informatics platform comprises:
      a first tool configured to retrieve first medical data of a patient from the database;
      a second tool linked to an application; and
      a third tool configured to:
         display, in a graphical user interface, concurrently with the first medical data, an area from which third party applications external to the system can be selected;
         responsive to receiving a selection of the third party application, enable the third party application to obtain one or more clinical items pertaining to the patient from the first medical data to process the one or more clinical items to generate second medical data related to the patient;
         receive, from the third party application, the second medical data;
         display, in the graphical user interface, at least some of the first medical data concurrently with the second medical data; and
         provide, via the graphical user interface, a virtual meeting interface, wherein the virtual meeting interface enables a user to flag one or more items of the at least some of the first medical data and the second medical data for discussion in a meeting.

2. The system of claim 1, wherein the plurality of information systems comprises two or more of an electronic medical record (EMR) system, a picture archiving and communication system (PACS), a laboratory information system (LIS), a radiology information system (RIS), a next generation sequencing (NGS) system, and a digital pathology (DP) system.

3. The system of claim 1, wherein the third tool is configured to provide, via the graphical user interface, an interactive workspace comprising an information section, a tool section, and a collaboration section;
   wherein the information section concurrently displays the at least some of the first medical data and the second medical data;
   wherein the tool section displays the area from which third party applications external to the system can be selected; and
   wherein the collaboration section enables at least one of synchronous collaboration or asynchronous collaboration among medical personnel.

4. The system of claim 3, wherein the information section includes demographic information of the patient and a summary of medical information of the patient.

5. The system of claim 4, wherein the information section includes an interactive visual timeline of a medical history of the patient, the medical history including a history of treatments, a history of diagnostic procedures, and results of the diagnostic procedures.

6. The system of claim 5, wherein the information section includes an image viewer to view one or more medical images of the patient, the one or more medical images being part of the first medical data of the patient.

7. The system of claim 6, wherein the image viewer is activatable from the interactive visual timeline.

8. The system of claim 3, wherein the collaboration section includes at least one of: a messaging interface or the virtual meeting interface.

9. The system of claim 8, wherein the messaging interface allows medical personnel to exchange messages about the patient via real-time or offline messages.

10. The system of claim 9, wherein the messages include at least some of the first medical data of the patient.

11. The system of claim 8, wherein the interactive workspace further includes a notification section; and
    wherein the third tool is configured to display, in the notification section, a first notification based on detecting that new clinical data for the patient is available at the database.

12. The system of claim 11, wherein the third tool is further configured to display, in the notification section, a second notification based on receiving an offline message for a user.

13. The system of claim 1, wherein the third tool is configured to generate a presentation to include the flagged one or more items for presenting in the meeting via the virtual meeting interface.

14. The system of claim 1, wherein the third tool is configured to track a number of the one or more items flagged by each participant of the meeting.

15. The system of claim 1, wherein the flagging of the one or more items includes associating one or more comments with the one or more items; and
    wherein the third tool is configured to track responses to the one or more comments by participants of the meeting received via a collaboration section.

16. The system of claim 1, wherein the first tool is configured to extract a plurality of information items from the at least some of the first medical data to generate structured data; and
    wherein the third tool is configured to display the structured data via the graphical user interface.

17. The system of claim 16, wherein the first tool is configured to extract the plurality of information items based on performing a natural language processing (NLP) operation on the at least some of the first medical data.

18. The system of claim 1, wherein the second tool is further configured to:

obtain a plurality of search criteria, wherein the search criteria are either determined automatically based on clinical characteristics associated with the first medical data of the patient or manually selected by a user from a list of clinical characteristics;

generate a search query from the search criteria;

transmit the search query to the application to generate a search result; and provide the search result to the third tool as the second medical data to be displayed in the graphical user interface.

19. The system of claim 18, wherein the search result comprises at least one of: one or more publications, one or more portions of a medical guideline, one or more clinical trials, or one or more patients having similar attributes as the patients.

\* \* \* \* \*